United States Patent
Friedrich et al.

(10) Patent No.: US 10,105,414 B2
(45) Date of Patent: Oct. 23, 2018

(54) PEPTIDES DERIVED FROM RS1 WHICH DOWN-REGULATE GLUCOSE ABSORPTION AFTER A GLUCOSE RICH MEAL AND INCREASE INSULIN SENSITIVITY

(71) Applicant: Julius-Maximilians-Universität Würzburg, Würzburg (DE)

(72) Inventors: Alexandra Friedrich, Würzburg (DE); Jürgen Groll, Würzburg (DE); Hermann Koepsell, Höchberg (DE); Maike Veyhl-Wichmann, Würzburg (DE)

(73) Assignee: Julius-Maximilians-Universität Würzburg, Würzburg (DE)

( * ) Notice: Subject to any disclaimer, the term of this patent is extended or adjusted under 35 U.S.C. 154(b) by 0 days.

(21) Appl. No.: 15/305,646

(22) PCT Filed: Apr. 23, 2015

(86) PCT No.: PCT/EP2015/058826
§ 371 (c)(1),
(2) Date: Oct. 20, 2016

(87) PCT Pub. No.: WO2015/162214
PCT Pub. Date: Oct. 29, 2015

(65) Prior Publication Data
US 2017/0042969 A1    Feb. 16, 2017

(30) Foreign Application Priority Data
Apr. 23, 2014  (EP) .................................... 14165597

(51) Int. Cl.
| | |
|---|---|
| A61K 38/17 | (2006.01) |
| A61K 9/00 | (2006.01) |
| A61P 3/00 | (2006.01) |
| A23L 33/18 | (2016.01) |
| A61K 38/06 | (2006.01) |

(52) U.S. Cl.
CPC .......... *A61K 38/1709* (2013.01); *A23L 33/18* (2016.08); *A61K 9/0053* (2013.01); *A61K 38/06* (2013.01); *A23V 2002/00* (2013.01)

(58) Field of Classification Search
CPC .. A61K 38/06; A61K 9/0053; A61K 38/1709; A23L 33/18; A23V 2002/00
See application file for complete search history.

(56) References Cited

U.S. PATENT DOCUMENTS

2009/0203621 A1*  8/2009  Koepsell ................ A61K 38/06
                                                              514/2.9

FOREIGN PATENT DOCUMENTS

| EP | 1 637 539 | 3/2006 |
|---|---|---|
| WO | WO 2006/105912 | 10/2006 |
| WO | WO 2006/105913 | 10/2006 |

OTHER PUBLICATIONS

Rudinger, Peptide Hormones, JA Parsons, Ed., 1976, pp. 1-7.*
Sigma, 2004, pp. 1-2.*
Berendsen, A Glimpse of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BloL (2002) 324, 373-386.*
Yampolsky et al, The Exchangeability of Amino Acids in Proteins, Genetics, 2005, 170, pp. 1459-1472.*

(Continued)

*Primary Examiner* — Julie Ha
*Assistant Examiner* — Li N Komatsu
(74) *Attorney, Agent, or Firm* — Parker Highlander PLLC

(57) ABSTRACT

The present invention relates to a pharmaceutical composition comprising a (poly)peptide which comprises or consists of QEP or a QEP derivative thereof a nucleic acid molecule encoding said (poly)peptide or a vector comprising said nucleic acid molecule, for use in the prevention or in the treatment of a disease or disorder caused by, physiologically linked to or associated with glucose and/or galactose uptake, wherein said pharmaceutical composition is to be administered under a high-sugar condition. Furthermore, the pharmaceutical composition of the invention is for use in increasing insulin sensitivity. The invention further relates to a food composition comprising said (poly)peptide. The invention further relates to a method of screening for and/or identifying a compound suitable to prevent or treat said disease or disorder under a high-sugar condition. The invention further relates to a method of screening for and/or identifying a compound which modulates ornithine decarboxylase (ODC), which is capable of inhibiting (SGLT1-mediated) glucose and/or galactose uptake into a cell expressing ODC and/or which is capable of increasing the inhibitory effect of an inhibitor of glucose and/or galactose uptake into a cell expressing ODC. The invention further relates to a method for predicting a patients non-response or response to said (poly)peptide, to a method for stratifying a patient for prevention or treatment with said (poly)peptide and to a kit for determining whether a patient suffering from said disease or disorder is a non-responder or responder to said polypeptide. The invention further relates to a method of developing and/or designing a compound/drug suitable to prevent or treat said disease or disorder.

Figure 1:
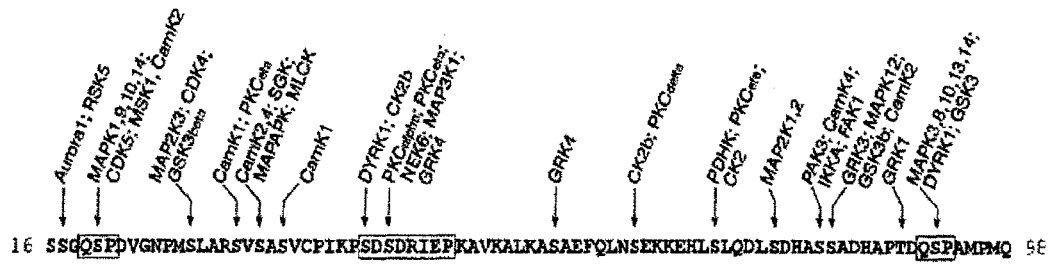

7 Claims, 15 Drawing Sheets
Specification includes a Sequence Listing.

(56) References Cited

OTHER PUBLICATIONS

PCT International Search Report and Written Opinion issued in International Application No. PCT/EP2015/058826, dated Jun. 29, 2015. 15 pages.
Vernaleken et al., "Tripeptides of RS1 (*RSC1A1*) inhibit a monosaccharide-dependent exocytotic pathway of $Na^+_{-D}$-glucose cotransporter SGLT1 with high affinity," *Journal of Biological Chemistry*, 282(39):28501-28513, 2007.

* cited by examiner

PEPTIDES DERIVED FROM RS1 WHICH DOWN-REGULATE GLUCOSE ABSORPTION AFTER A GLUCOSE RICH MEAL AND INCREASE INSULIN SENSITIVITY

This application is a national phase application under 35 U.S.C. § 371 of International Application No. PCT/EP2015/058826, filed Apr. 23, 2015, which claims benefit of European Application No. 14165597.7, filed Apr. 23, 2014, the entire contents of each of which are hereby incorporated by reference.

The present invention relates to a pharmaceutical composition comprising a (poly)peptide which comprises or consists of QEP or a QEP derivative thereof, a nucleic acid molecule encoding said (poly)peptide or a vector comprising said nucleic acid molecule, for use in the prevention or in the treatment of a disease or disorder caused by, physiologically linked to or associated with glucose and/or galactose uptake, wherein said pharmaceutical composition is to be administered under a high-sugar condition. Furthermore, the pharmaceutical composition of the invention is for use in increasing insulin sensitivity. The invention further relates to a food composition comprising said (poly)peptide. The invention further relates to a method of screening for and/or identifying a compound suitable to prevent or treat said disease or disorder under a high-sugar condition. The invention further relates to a method of screening for and/or identifying a compound which modulates ornithine decarboxylase (ODC), which is capable of inhibiting (SGLT1-mediated) glucose and/or galactose uptake into a cell expressing ODC and/or which is capable of increasing the inhibitory effect of an inhibitor of glucose and/or galactose uptake into a cell expressing ODC. The invention further relates to a method for predicting a patient's non-response or response to said (poly)peptide, to a method for stratifying a patient for prevention or treatment with said (poly)peptide and to a kit for determining whether a patient suffering from said disease or disorder is a non-responder or responder to said polypeptide. The invention further relates to a method of developing and/or designing a compound/drug suitable to prevent or treat said disease or disorder.

In the affluent industrial nations, the increased occurrence of nutrition-dependent diseases (e. g. obesitas/adipositas, hypercholesterolemla, diabetes and hyperglycaemia) is a serious problem. For example, obesity has risen to alarming levels world-wide (McLellan (2002), Lancet 359, 1412). For instance, the average weight of German conscripts now increases by almost 400 g/year. Similar data were obtained in Austria, Norway and the UK.

Known therapies for obese patients comprise physical activity, special diets as well as drug therapies. One particular drug therapy approach is based on Orlistat (Xenical) which prevents the absorption of some fat in the intestine. Also appetite depressants and/or appetite suppressants have been proposed. Many drugs which have been tested as appetite suppressants interfere with monoamine-neurotransmitters (serotonin, noradrenalin, dopamine, histamine). 5-HT (5-hydroxytryptamine) is released in various sites of the hypothalamus, a brain region believed to be involved in the regulation of food intake. D-fenfluramine is a 5-HT releaser and reuptake inhibitor mostly used in combination with Phentermine (Fen-Phen) to treat obesity. Fen-Phen, however, was withdrawn from the market due to potential heart valve defects (Wadden (1999), Obes. Res. 7, 309-310). Also the popular appetite suppressant drug fenfluramine and dexfenfluramine have been withdrawn from the market. The FDA stated that these two drugs are linked to heart valve disease and Primary Pulmonary Hypertension (PPH). Also topiramate has been proposed in the treatment of obesity (The Pharmaceutical Journal (1999), Vol. 263, No 7064, page 475). However, topiramate is known to provide for side effects in brain regions. Kaminski (2004 Neuropharmacology 46(8):1097-104) showed that topiramate selectively inhibits postsynaptic responses mediated by GluR5 kinate receptors. Also, various special diets (having extreme ratios of nutritients), psychopharmacological drugs and an α-glucosidase inhibitor (acarbose, Glucobay®), Bayer-Vital, Leverkusen) that inhibits the degradation of disaccharides in small intestine, have been proposed in the treatment of obesity, diabetes and/or the corresponding secondary disorders. However, all known therapeutical forms have the major disadvantage to have substantial side effects.

As further means for the treatment of nutrition-related diseases, the development of inhibitors of the sodium-D-glucose/galactose cotransporters SGLT1 and SGLT2 have been proposed. SGLT1 mediates the absorption of D-glucose (and/or D-galactose) in the small intestine whereas SGLT2 mediates the first step in reabsorption of D-glucose (and/or D-galactose) in renal proximal tubules. These attempts for the treatment of nutrition related diseases are based on the development of non-transported substrate analogues that act as competitive inhibitors (Oku (1999), Diabetes 48, 1794-1800; Dudash (2004), Bioorg. Med. Chem. Lett. 14, 5121-5125). The inhibition of glucose transport by such compounds requires their continuous presence at the binding site at high concentrations. This permanent presence can cause side effects in organs which are not desired to be affected (e.g. severe detrimental effects heart where SGLT1 is expressed (Zhou (2003) Journal Cell Biochem 90, 339-346).

Beside the problem of side effects of pharmacological options for the treatment of nutrition related diseases, also diets comprising a sharp reduction of food uptake over a long period of time are often not accepted by the patients and a change in nutrient habits is often refused.

Attempts were also made to provide therapies for the treatment of nutrition-related diseases, like diabetes and hyperglycemia, by the provision of antagonists (for example antibodies, anti-sense molecules, ribozymes) of the regulatory protein RS1 which is encoded by the RSC1A1 gene (DE-A1 10006887).

It has also been shown that the removal of the regulatory protein RS1 (gene RSC1A1) in an animal model leads to a post-transcriptional upregulation of SGLT1, to an increase of serum cholesterol and to obesity (Osswald (2005) Mol Cell Biol. 25, 78-87). RS1, as a molecule or in form of an RS1 encoding gene, was proposed to be used in the treatment of adipositas or hypercholesterolemia; see EP-A1 1 444 890. An RS1-knock-out animal model, the alternation of the activity of RS1 in influencing body weight and the possibility to diagnose obesity via testing the expression or activity of RS1 was described in EP-A1 1 444 890 and in U.S. Ser. No. 10/771,151.

Peptides corresponding to motifs of hRS1 (QCP, QSP, QPP, QTP) were identified as being able to induce posttranscriptional inhibition of SGLT1 expression in the absence of considerable glucose concentrations in the physiological range (WO 2006/105913). In the presence of such glucose concentrations, this inhibition was abrogated. This glucose dependent blunting of the SGLT1-inhibitory effect of these peptides was considered as being of particular value for the in vivo use of these peptides to down-regulate small intestinal glucose absorption at low glucose concentrations. Hence, the use of these peptides to treat diabetes, obesity etc.

has been proposed in particular in combination with carbohydrate-low diets and diets having a low glycamic index, respectively. The disclosure of Vemaleken confirmed these findings (J. Biol. Chem. (2007) 282, 28501-13; "Dissertation zur Erlangung des naturwissenschaftlichen Doktorgrades der Bayerischen Julius-Maximilians-Universität Würzburg" (2007), "Identification and Characterisation of the Domains of RS1 (RSC1A1) Inhibiting the Monosaccharide Dependent Exocytotic Pathway of Na+-D-Glucose Cotransporter SGLT1 with High Affinity"). Similarly, an octapeptide corresponding to a particular motif of human RS1 (SDSDRIEP) has also been proposed to downregulate SGLT1 (WO 2006/105912).

It is further known that the RS1 protein does not only inhibit the expression of hSGLT1 but also inhibits the expression of other transporters that are expressed in the small intestine, for example the organic cation transporter hOCT2 (SLC22A2) (Koepsell, Pflügers Arch-Eur J Physiol (2004), 447:666-76; Reinhardt, Biochim Biophys Acta (1999), 1417:131-43; Veyhl, Am J. Physiol Renal Physiol (2006), 291:F1213-F1223).

It is further known that glucose absorption in the small intestine is critically dependent on glucose transport across the luminal brush-border membrane of enterocytes which is mediated by the Na+-D-glucose cotransporter SGLT1 (Gorboulev, Diabetes 61 (2012), 187-196). After glucose-rich meals, SGLT1 is upregulated posttranscriptionally due to glucose dependent release of SGLT1 containing vesicles from the Golgi apparatus which are incorporated into the brush-border membrane (Veyhl, Am J. Physiol Renal Physiol (2006), 291:F1213-F1223).

The role of RS1 for posttranslational downregulation of transporters has primarily been studied using oocytes of *Xenopus laevis* in which SGLT1 and other transporters were expressed by mRNA injections and RS1 protein was injected. Using the oocyte expression system it was observed that hRS1 protein posttranslationally downregulates hSGLT1, the human Na+-nucldeosidecotransporter hCNT1 and some other transporters (Errasti-Murugarren, Mol Pharmacol 82 (2012), 59-87). Enteroendocrine L-cell which secrete the antidiabetic hormone glucagon like peptide 1 (GLP-1) in response to glucose and short chain fatty acids are located in the distal part of small intestine. During a glucose-rich meal, GLP-1 potentiates glucose dependent insulin secretion of the pancreatic islands. It has been shown that the L-cells express SGLT1 and the role of SGLT1 for glucose-dependent stimulation of GLP-1 by L-cells has been discussed (Gorboulev loc. cit.). Moreover, it has been reported that inhibition of SGLT1 in the small intestine or genetic removal of SGLT1 lead to an increase of GLP-1 secretion 30 min—2 h after gavage with glucose (Powell, J Pharmacol Exp Ther 34 (2013), 250-259).

Thus, the technical problem underlying the present invention is the provision of means and methods for an improved, broad medical intervention against diabetes and other diseases/disorders caused by, physiologically linked to or associated with glucose and/or galactose uptake.

The technical problem is solved by the provision of the embodiments characterized in the claims.

Accordingly, the present invention relates to a pharmaceutical composition comprising
(a) a (poly)peptide which comprises or consists of
  (A) the amino add sequence glutamine-glutamic acid-proline (QEP); or
  (B) a derivative of the amino acid sequence QEP (wherein said derivative is capable of reducing inhibiting SGLT1-mediated glucose and/or galactose uptake into a cell in the presence of an increased concentration of glucose and/or galactose),
(b) a nucleic acid molecule encoding the (poly)peptide of (a); or
(c) a vector comprising the nucleic acid molecule of (b)
for use in the prevention or in the treatment of a disease or disorder caused by, physiologically linked to or associated with glucose and/or galactose uptake or of a nutrition-related or nutrition-dependent disease or disorder,
wherein (in the context of said prevention or treatment) said pharmaceutical composition is (is to be or is prepared to be) administered to a patient (suffering or being expected to suffer from said disease or disorder), said patient having, going to have or being expected to have an increased concentration of glucose and/or galactose in the lumen and/or in the epithelial cells of at least one part of its gastrointestinal tract (and/or its blood and/or in its urine).

The gist of the invention lays in the surprising finding that particular RS1-derived (poly)peptide variants, in particular the tripeptide QEP and its derivatives, are capable to reduce SGLT1-mediated glucose uptake under high-sugar conditions. Such high-sugar conditions occur, for example, after an energy-rich meal. It is an outstanding advantage of the invention that these (poly)peptide variants can be very short and that, hence, very simple means and methods for the medical intervention against diabetes and other diseases/disorders caused by, physiologically linked to or associated with glucose and/or galactose uptake can be provided. Since native/endogenous RS1 inhibits the uptake of glucose/mannose within the small intestine only in the presence of low glucose/mannose concentrations in the small intestine, for example between (carbohydrate-rich) meals but not during or (directly) after (carbohydrate-rich) meals, native/endogenous RS1 or non-modified RS1 derived polypeptides are not efficient to inhibit small intestinal glucose/galactose uptake during or (directly) after (carbohydrate-rich) meals (Vemaleken (2007) loc. cit.).

The invention further relates to a pharmaceutical composition as defined in (a) to (c), supra, for use in the prevention or treatment of such a disease or disorder, wherein said pharmaceutical composition is, is to be, or is prepared to be administered to a respective patient under (a) high-sugar condition(s)/situation(s) (for example under (a) high-glucose and/or (a) high-galactose condition(s)/situation(s)).

The invention further relates to a pharmaceutical composition as defined above, wherein
(i) the patient to which it is, or is to be, administered is taking, is going to take or is being expected to take an energy-rich meal;
(ii) said pharmaceutical composition is, is to be or is prepared to be administered in combination with such a meal or in combination with an energy-rich diet/food/food intake;
(ii) the patient to which said pharmaceutical composition is, or is to be, administered has, is going to have or is being expected to have an increased level of sugar (e.g. glucose and/or galactose) in the lumen and/or in the epithelial cells of at least one part of its gastrointestinal tract, in its blood and/or in its urine; and/or
(iv) said pharmaceutical composition is, is to be or is prepared to be administered under (a) high-sugar condition(s)/situation(s) (for example under (a) high-glucose and/or (a) high-galactose condition(s)/situation(s).

The invention further relates to a method of treating or preventing the above-described disease or disorder, said method comprising the step of administering to a patient in need thereof a pharmaceutically effective amount of the above-described pharmaceutical composition under the above-described high-sugar condition(s)/situation(s).

The present invention solves the above identified technical problem since, as documented herein below and in the appended examples, it was surprisingly found that particular RS1-derived (poly)peptide variants like the tripeptide QEP, QEP derivatives (like the modified tripeptide QS$_{thiophosphate}$P), a modified fragment of RS1 (like the modified human RS1 regulatory domain hRS1-Reg(S20E) or the modified mouse RS1 regulatory domain mRS1(S19E) are capable to reduce SGLT1-mediated uptake of, for example, glucose and/or galactose into SGLT1-expressing cells (for example epithelial cells of the small intestine) under a high-sugar condition, like, for example, a condition characterized by the presence of high intracellular glucose and/or galactose concentrations similar to those observed during or after an energy-rich meal. In particular, it was documented herein and in the appended examples that the RS1-derived (poly)peptide variants are capable to down-regulate hSGLT1 in human small intestine after an energy-rich meal by up to 75%.

The RS1-derived (poly)peptide variants, and the other active compounds/ingredients described herein, share the structural characteristics that they represent a modified endogenous peptide motif of the regulatory domain of RS1 (RS1-Reg), namely, they comprise or consist of the peptide motif QEP or a QEP derivative. Without being bound by theory, the respective modification mimicks phosphorylation of the serine residue within the N-terminal QSP motif in RS1-Reg (e.g. hRS1-Reg or mRS1-Reg). The herein described compounds are capable to down-regulate SGLT1 under a high-sugar condition as, for example, occurring during or after an energy-rich meal when intracellular glucose and/or galactose in the enterocytes of the small intestine is high. The endogenous RS1-Reg or RS1-Reg-derived non-modified motifs like QSP and SDSDRIEP in hRS1-Reg are not effective under such a condition.

In particular, the compounds described herein are capable to decrease SGLT1-mediated glucose and/or galactose uptake under high-sugar conditions. Without being bound by theory, the underlying mechanism is a down-regulation of the SGLT1 protein in the luminal membrane of the enterocytes. Since SGLT1-mediated glucose/galactose uptake determines the rate of small intestinal glucose/galactose absorption, the herein described compounds are able to reduce small intestinal glucose/galactose absorption during or after energy-rich meals. Hence, these compounds can be used to reduce glucose/galactose absorption during prevention or treatment of diseases or disorders like obesity and diabetes, even though (an) energy-rich meal(s) is (are) taken. Without being bound by theory, the reduction of glucose/galactose absorption in proximal small intestine leads to an increased secretion of the antidiabetic enterohormone glucagone like peptide 1 (GLP-1). Hence, it is expected that an administration of compounds which decrease SGLT1 activity or down-regulate SGLT1 expression increase GLP-1 secretion. The GLP-1 induced increase of insulin secretion will (further) improve the disturbed homeostasis of blood glucose during diseases or disorders like diabetes type 2.

In the context of the present invention it was further surprisingly found that the herein described active compounds (for example the compounds as defined in (a) to (c), supra) are also capable to increase the sensitivity to insulin, in particular at a low dose applied on a medium- or long-term basis (for example over 3 days). Since one of the relevant characteristics of the herein described diseases or disorders like obesity and diabetes type 2 is an increased insulin resistance, the decrease of insulin resistance by the herein described compounds provides for a preventive and therapeutic improvement of the intervention against such diseases or disorders.

It was further surprisingly found that the herein described active compounds are effective even if endogenous RS1 is present in the small intestine and even in the presence of high glucose/galactose concentrations in the small intestine when the function of endogeneous RS1 is supposed to be blocked.

In principle, the herein described tripeptides (for example QEP and QS$_{thiophosphate}$P) may be applied as such. Without being bound by theory, after oral administration, they enter the enterocytes via the peptide transporter PEPT1. The RS1-Reg variants and other longer (poly)peptides may not enter the enterocytes as such. However, in the context of the invention, also means and methods are provided which even allow for an oral application of these (longer) compounds. In particular, longer (poly)peptides, like the RS1-Reg variants, are shown herein to be able to enter the enterocytes when they are coupled to nanoparticles. Surprisingly, it was even found in the context of the invention that the so administered (poly)peptides can be administered more efficiently and exhibit their efficacy (SGLT1-inhibitory effect) at lower dosages, respectively.

Moreover, the receptor of the herein described (poly)peptides (RS1-Reg variants, QEP, QS$_{thiophosphate}$P and the like) for down-regulation of SGLT1 has been identified and offers the opportunity to develop second generation compounds for an improved medical intervention of the herein described diseases and disorders.

In particular, it was found in the context of this invention that RS1-Reg binds to ornithrine decarboxylase (ODC) which s supposed to contain a glucose binding site that modifies the affinity of the RS1-Reg binding site after binding of glucose. Without being bound by theory, the binding site of ODC for RS1-Reg is large including binding domains for QSP/QEP and SDSDRIEP. It was also observed in the context of the invention that the phosphorylation pattern of (human) RS1-Reg determines whether (human) RS1-Reg binds to ODC and down-regulates SGLT1; or to other receptor proteins regulating other transporters.

In the context of the invention also hints are provided that a combination of the herein described active compounds (e.g. QEP or QS$_{thiophosphate}$P) with SDSDRIEP, or with (an)other regulatory protein RS1 fragment(s) as described in WO 2006/105912, is even more effective for down-regulation of SGLT1 in the presence of high intracellular glucose/galactose as compared to said described compounds alone. Furthermore, hints are provided that a combination of the herein described compounds (e.g. QEP or QS$_{thiophosphate}$P) with QCP, QSP, QPP and/or QTP, or with (an)other regulatory RS1 fragment(s) as described in WO 2006/105913, is even more effective as compared to said described compounds alone.

Without being bound by theory, this is because hRS1-Reg contains an SDSDRIEP motif which is able to mediate downregulation of hSGLT1 in oocytes and hRS1-Reg also contains two QSP motifs, i.e. the N-terminal one which has been shown to be relevant for down-regulation of SGLT1 in the presence of high intracellular glucose/galactose, and a C-terminal one.

The herein provided/improved understanding of the post-translational regulation of transporters by hRS1 implicates that different peptides in the "QXP"-format ("X" is any amino acid) may have different affinities for down-regulation of SGLT1 and/or for binding to ODC. It also implicates that different peptides in the "QXP"-format may exhibit different glucose-induced affinity changes for down-regulation of hSGLT1 and/or for binding to ODC without bound glucose versus binding to ODC with bound glucose. In contrast, it was thought in the art that "QXP"-type peptides are not capable to down-regulate the hSGLT1 expression in the presence of high intracellular glucose concentrations (in physiological ranges) and have a very low affinity for down-regulation of hSGLT1, as has been observed for hRS1-Reg wildtype (see, for example, Vemaleken, loc. cit.). Since the presence of high glucose concentrations are expected in enterocytes after ingestion of energy-rich food, it appeared that "QXP"-type peptides are not able to down regulate SGLT1 in the luminal membrane of the enterocytes during or after such ingestion. When the carbohydrate content in the small intestine between meals or overnight is low, the "QXP"-type peptides were supposed to be active.

However, the data underlying the present invention demonstrate that a (poly)peptide which comprises or consists of QEP or a QEP derivative is a hSGLT1-specific posttranslational inhibitor that down-regulates the expression of hSGLT1 with very high affinity under (a) high-sugar situation(s), for example in the presence of (a) high intracellular concentration(s) of glucose/galactose. Hence, in contrast to the "QXP"-type peptide QSP, and the other regulatory protein RS1 fragments known in the art (e.g. WO 2006/105912, WO 2006/105913, Vemaleken, loc. cit.), the particular "QXP"-type peptide QEP and its derivative(s) is/are capable to inhibit small intestinal glucose/galactose absorption, for example as occurring during or after an energy-rich meal.

One advantage of the pharmaceutical composition of the invention is the low toxicity of the compounds to be administered and the less/reduced side effects, respectively. A further advantage of the pharmaceutical composition of the invention is the simplicity of the compounds to be administered and the opportunity of their easy and cost-efficient production, respectively. Yet other advantages of the pharmaceutical composition of the invention are that the amount/dosage of other pharmaceutical compositions (e.g. insulin, Metformin, Sitagliptin) for the prevention or treatment of any of the diseases or disorders as described herein can be reduced and that even a patient suffering from any of such diseases or disorders can take an energy-rich meal/food/food intake and/or undergo an energy-rich diet (without (an) adverse effect(s)).

The disease or disorder to be prevented or treated according to the invention is caused by, physiologically linked to or associated with glucose and/or galactose uptake, for example into cells, tissues and/or organs. In particular, the disease or disorder to be prevented or treated is associated with the function of SGLT (or a homologue thereof) and, more particular, of SGLT1 (or a homologue thereof). The disease or disorder to be prevented or treated may be a metabolic disease or disorder of the carbohydrate metabolism, in particular of the glucose and/or galactose metabolism. Moreover, the disease or disorder to be prevented or treated may be a nutrition-dependent or nutrition-related disease/disorder. In particular, the disease or disorder to be prevented or treated according to the invention is, at least in part, caused by, physiologically linked to or associated with (aberrant) glucose and/or galactose uptake by SGLT (or a homologue thereof) and, more particular, SGLT1 (or a homologue thereof). More particular, the disease or disorder to be treated/prevented is associated with (aberrant) (D-)glucose and/or (D-)galactose uptake into cells, in particular into cells expressing an SGLT (SGLT1 and/or 2) or a homologue thereof. A non-limiting example of such cells is the enterocytes of the small intestine. Likewise, the disease or disorder to be treated/prevented is associated with (aberrant) (D-)glucose and/or (D-) galactose uptake by an organ, for example by an organ expressing an SGLT (SGLT1 and/or 2) or a homologue thereof. A non-limiting example of such an organ is the small intestine.

SGLT is a Na+-D-glucose and/or D-galactose transporter known in the art (e.g. SGLT1; SLC5A1 acc. no. NM_000343; Wright (2004) Plfügers Arch. Eur. J. Physiol. 447, 510; RSC1A1; DE-A1 100 06 887). SGLTs are known to catalyze the transport, i.e. uptake, of D-glucose and/or D-galactose into the cytosol of cells via the cellular membrane. In humans, SGLT1 is, for example, strongly expressed in the small intestine, where it plays a major role in the uptake of ingested D-glucose and/or D-galactose or D-glucose and/or D-galactose which is released from ingested food as a result of digestion in the gastrointestinal tract.

An "SGLT homologue" is any protein which acts/functions like an SGLT, in particular any protein which shows at least one of the herein-mentioned features of SGLTs. The term "SGLT homologue" also refers to any protein which shows substantial sequence similarity to SGLTs like SGLT1 or 2. Such sequence similarity may be more than 60%, 70%, 80%, 90%, 95%, 98% or 99% sequence identity with SGLTs like SGLT2 or SGLT1 (SLC5A1 acc. no. NM_0003443) on amino acid level. In a specific embodiment, "SGLT homologue" refers to the orthologue of a human SGLT as present in a non-human species.

Accordingly, the term "disease or disorder associated with the function of an SGLT or a homologue thereof" refers to any disease or disorder which, at least partially, results from or is due to one of the activities/functions/features of an SGLT or one of its homologues. For example, such activities/functions/features are those mentioned above and, in particular, Na+-D-glucose and/or D-galactose transport. In the context of this invention, "associated with" means "due to", "resulting from", "based on" etc. glucose and/or galactose uptake and/or the function of an SGLT or a homologue thereof like, for example, D-glucose and/or D-galactose uptake/transport.

In one particular embodiment, the diseases or disorders to be treated or prevented in accordance with this invention are associated with a surplus supply of nutrition and, in particular, a surplus of easily digestable carbohydrates, which leads/lead to a surplus of D-glucose and/or D-galactose in at least one part of the gastrointestinal tract and, hence, in the respective epithelial cells.

The preventing or treating of eating disorders leading to increased body weight/body mass or of disorders related to higher or pathologically high body weight due to the use of drugs (like corticosteroids, antipsychotic drugs, antidepressants, particularly tricyclic antidepressants, oral contraceptives, etc.) is also envisaged.

Disorders of metabolism linked to higher body weight/body mass are also envisaged to be treated or prevented. These comprise glycogen storage diseases, lipid storage diseases (like, e.g., Gaucher, Niemann Pieck), endocrine disorders (like, e.g., Cushings, hypothyroidism, insulinomas, lack of growth hormone, diabetes (like, for example, diabetes type 1 or 2), adrenogenltal syndrome, diseases of the adrenal cortex), tumors and metastases (such as craniophryngeomas), Prader-Willi syndrome, Down syndrome and genetic diseases and syndromes (like, e.g., hyperlipoproteinemias) or hypothalmic disorders.

The prevention and treatment of secondary disorders, consecutive complications and/or symptoms of any of the above and herein elsewhere defined diseases and disorders is also envisaged. For example, such secondary disorders, consecutive complications and/or symptoms are related to or caused by a (pathologically) high body weight and/or the occurrence of high blood glucose/galactose concentrations. These comprise, but are not limited to, high blood pressure (hypertension), cardio-vascular diseases, stroke, cancer, problems with sexual function and disorder of the muscular or bone system. Said cardio-vascular diseases comprise infarcts and stroke. Further, non-limiting examples of such consecutive complications and/or symptoms are high peaks of blood glucose level (for example after an energy-rich meal), secondary damage of organs/organ systems (e.g. kidneys, eyes, nerves, blood vessels, skin), cardiovascular diseases, blood flow disorders, diabetic skin infections, diabetic visual disorders, diabetic nephropathy, diabetic neuropathy, diabetic leg ulcers, diabetic retinopathy, diabetic oculomotor nerve palsy, diabetic glomerulosclerosis, diabetic vulvitis, diabetic glomerulonephritis etc.

The present invention also provides for means and methods for the medical intervention in an overweight subject, in particular in an overweight human patient. Also envisaged is the prevention or treatment of diseases/disorders related to, caused by or leading to higher or pathologically high body weight.

The medical intervention of a disease or disorder associated with higher levels of triglycerides and/or cholesterol in the blood of a patient is also envisaged. The recommended level of triglycerides (in a normal range) in males is 40-160 mg/dL and in females are 35 to 135 mg/dL. The recommended level of cholesterol (in a normal range) is 150-220 mg/100 ml.

Particular, non-limiting, diseases or disorders to be prevented or treated according to the invention are selected from the group consisting of obesity (adipositas), diabetes mellitus (type 1 or 2), hyperglycemia, hypercholesterolemia, defects in insulin secretion and/or insulin action and impaired glucose and/or galactose tolerance.

In one particular embodiment, obesity is to be prevented or treated. In another particular embodiment, diabetes, in particular type 1 or, preferably, type 2 diabetes is to be prevented or treated.

More particular, a disease or disorder to be prevented or treated according to the invention is selected from the group consisting of type 2 diabetes and prediabetes, even more particular, selected from the group consisting of untreated (slight/little pronounced) type 2 diabetes and untreated (slight/little pronounced) prediabetes.

Other diseases or disorders to be treated or prevented are described herein elsewhere. The skilled person/attending physician is readily in the position to treat or prevent other medical conditions following the gist of this invention, i.e. the medical use of an active compound as described herein (e.g. a (poly)peptide which consists of or comprises the amino acid sequence QEP or a derivative thereof).

Moreover, the skilled person/attending physician is well familiar with the diseases and disorders to be prevented or treated in accordance with the invention. In particular, the skilled person/attending physician knows how to, and is readily able to, diagnose the respective diseases and disorders.

For example, obesity or adipositas is commonly known as a disorder of appetite regulation and/or energy metabolism controlled by specific biological factors. Besides severe risks of illness such as diabetes, hypertension and heart disease, individuals suffering from obesity are often isolated socially. Obesity has a major impact on a person's physical, social and emotional well-being. Besides this, obesity regularly lead to an increased risk of illness including type 2 diabetes and/or high blood pressure (hypertension), that may further lead to other cardiovascular diseases and/or stroke. Obesity regularly also plays a role in cancer, problems with sexual-function, muscle and bone disorders and dyslipidaemia. Obesity may, inter alia, be characterized by elevated fasting plasma insulin and/or an exaggerated insulin response to oral glucose intake (Kolterman (1980), J. Clin. Invest 65, 1272-1284). Moreover, a clear involvement of obesity in type 2 diabetes mellitus can be confirmed (Kopelman (2000), loc. cit.; Colditz (1995), Arch. Int. Med. 122, 481-486).

Commonly, the skilled person/attending physician refers to "obesity" when the Body Mass Index (BMI) of the patent is 30 $kg/m^2$ or more. The BMI is commonly calculated by dividing the patient's weight in kg by the height in meters squared. "Overweight" commonly means that the BMI of the corresponding patient is 25 $kg/m^2$ or more. Alternatively, a person is considered obese if he or she has 20 percent or more extra body fat with regard to his/her age, height, sex, and bone structure.

Hence, in one embodiment, the patients to be treated in accordance with this invention have a BMI of 25 $kg/m^2$ or more, in particular, a BMI of 30 $kg/m^2$ or more. In certain medically indicated cases, it is also envisaged that patients with a BMI below 25 $kg/m^2$ am to be treated in order to reduce their body weight.

Also diabetes or diabetes mellitus is commonly known to relate to a group of metabolic disorders sharing the common underlying feature of hyperglycemia. Usually, hyperglycemia in diabetes results from defects in insulin secretion, insulin action, or, most commonly, both. The common meaning of diabetes or diabetes mellitus is, for example, described in Kumar ("Clinical Medicine", $3^{rd}$ edition, 1994, Bailliére Tindall). Commonly, diabetes encompasses diseases or disorders like type 1 diabetes, type 2 diabetes and prediabetes (impaired glucose tolerance), and others.

Blood glucose values are normally maintained in a very narrow range, usually 70 to 120 mg/dL. The diagnosis of diabetes is commonly established by noting elevation of blood glucose by any one of the following three criteria:
1. A random glucose concentration greater than 200 mg/dL, with classical signs and symptoms.
2. A fasting glucose concentration greater than 126 mg/dL on more than one occasion.
3. An abnormal oral glucose tolerance test (OGTT), in which the glucose concentration is greater than 200 mg/dL 2 h after a standard carbohydrate load.

Commonly, a patient which suffers from (untreated) prediabetes has a blood glucose (and/or galactose) concentration (under uninebration) in between about ≥80 and about ≤120 mg/100 ml, in particular, in between about ≥90 and about ≤110 mg/100 ml. Normally, such a patient would have a blood glucose (and/or galactose) concentration in between about ≥140 and about ≤200 mg/100 ml about 2 hours after an OGTT.

Commonly, a patient which suffers from (untreated) slight/little pronounced type 2 diabetes has a blood glucose (and/or galactose) concentration (under uninebration) of about ≥100 mg/100 ml, in particular of about ≥110 mg/100 ml. Normally, such a patient would have a blood glucose (and/or galactose) concentration of about ≥180 mg/100 ml, in particular of about ≥200 mg/100 ml, about 2 h after an OGTT. Typically, a patient which suffers from type 2 diabetes and, in particular from (un-treated) slight/little pronounced type 2 diabetes has a reduced sensitivity to insulin.

In particular, the pharmaceutical composition as disclosed herein is, is to be or is prepared to be administered to a patient which suffers, is going to suffer or is expected to suffer from any of the diseases, disorders, complications and/or symptoms as described herein.

In one aspect, the patient is a (hitherto) untreated patient, i.e. a patient which is not, or is not to be, treated as to the herein described disease, disorder, complication and/or symptom with (an)other pharmaceutical composition(s).

In another aspect, the patient is already treated, or is to be treated, as to this disease, disorder, complication and/or symptom with (an) other pharmaceutical composition(s).

Hence, it is also envisaged according to the invention that the herein disclosed pharmaceutical composition is (to be) or is prepared to be administered to a patient in the context of a co-therapy or co-prevention (with (an)other pharmaceutical composition(s)), in particular, in the context of a co-therapy or co-prevention of a disease, disorder, complication and/or symptom as described herein (with (an)other pharmaceutical composition(s)).

A particular example of an un-treated patient in accordance with the invention is an un-treated patient suffering from prediabetes or type 2 diabetes, in particular slight/little pronounced prediabetes or type 2 diabetes.

The herein disclosed pharmaceutical composition may be administered in combination with one or more other anti-diabetic agent(s), in particular with one or more other anti-diabetic agent(s) having a different mode of action.

One example of such a co-therapy or co-prevention is an administration in combination with Metformin, in particular in cases where an administration of Metformin alone is insufficient (the common situation as to the administration of Metformin alone). Another example of such a co-therapy or co-prevention is the administration in combination with a sulfonyl urea derivative. Another example is the administration in combination with both, Metformin and insulin. In such a co-therapy or co-prevention, the amount/dosage of insulin (and/or Metformin) to be administered to the patient may be reduced. Another example is the administration in combination with one or more inhibitor(s) of the renal glucose (and/or galactose) transporter SGLT2 (e.g. Dapagliflozin or Canagliflozin) Such a combined administration offers the opportunity of an improved (long-term) adaption of the blood sugar level.

A (poly)peptide as described in the context of this invention may also be administered in combination with (an) other peptide(s) representing (h)RS1 or with one or more other (poly)peptide(s) as described in the context of this invention. For example, it is envisaged that all possible combinations of a (poly)peptide as described in the context of this invention and a RS1 fragment as disclosed in WO 2006/105913 and WO 2006/105912 are employed. Particular examples of these other peptides are peptides/proteins consisting of or comprising the amino acid sequences OCP, OSP, QTP, QPP, QTP and/or SDSDRIEP (or consisting of or comprising at least 3 consecutive amino acid residues of SDSDRIEP (but comprising the second S residue (S45))). It s clear that in any of such combination at least one of a (poly)peptide as described in the context of this invention is comprised. It is particularly envisaged that solely a peptide as described in the context of this invention is employed.

The herein disclosed pharmaceutical composition may also be administered in lieu of another pharmaceutical composition for the treatment/prevention of the disease or disorder described herein, for example in lieu of an GLP1-analog (for example Exenatid) or in lieu of dipeptidylpeptidase 4-Inhibitors (for example Sitagliptin). As compared to GLP1-analoga and dipeptidylpeptidase 4-inhibitors, the pharmaceutical composition of the invention provides for the advantage that physiological stimulation of GLP1 secretion (and the resulting effect) occurs only during or after an energy-rich meal, the uptake of energy-rich food and/or during an energy-rich diet. Hence, the pharmaceutical composition of the invention provides for the advantage that less/reduced side effects occur also in this respect.

As mentioned, it is particularly envisaged that, in the context of the above or herein elsewhere described (co-)prevention or (co-)therapy, the pharmaceutical composition is, is to be or is prepared to be administered under a high-sugar condition, in particular, under a high-sugar condition as described herein above, for example, in sections (i) to (iv), supra. Under such a condition, the (poly)peptide or other active compounds as defined herein (or a pharmaceutically acceptable salt thereof) may also be used to decrease, smoothen and/or prevent high peaks of glucose within the serum of, for example, diabetic patients, in particularly diabetic patients being adjusted insufficiently.

The use of the herein described active compound (for example (poly)peptide, nucleic acid molecule or vector) for reducing bodyweight or in avoiding an increase in bodyweight is also envisaged. Also in this aspect, the described active compound is, is to be or is prepared to be administered under a high-sugar condition/situation.

In general, it is envisaged that QEP itself, a derivative of QEP and a (poly)peptide comprising one or more of QEP and/or (a) QEP derivative(s) are to be used in accordance with this invention.

In principle, a "derivative of QEP" or "QEP derivative" refers to any compound, in particular any tripeptide, which has a sterical/chemical structure similar or even identical to that of QEP. A QEP derivative is also characterized in that it has a similar or the same three-dimensional/tertiary structure as the original QEP amino acid sequence per se, or as QEP being comprised in a longer (poly)peptide with more amino acid residues. Accordingly, and most preferably, the QEP derivative has, as compared to the original QEP motive an essentially unchanged three-dimensional/tertiary structure. However, some (slight) differences in the three-dimensional/tertiary structure are allowed, as long as the QEP activity/function is maintained. The person skilled in the art is readily in the position to deduce corresponding three-dimensional and/or tertiary structures.

For example, "QEP derivative" refers to an amino acid stretch QXP, wherein X is an amino acid or amino acid-like compound which is similar to E (i.e. has a chemical/sterical structure and/or "structural behaviour" similar to that of E within a three-dimensional (tri)peptide, in particular within QXP). X is also further referred to herein as being an E analogue. An amino acid-like compound may, for example, be a compound which does not fall within the art-known definition of "amino acid" but can be incorporated in a stretch of amino acids, i.e. into a peptide/protein.

"E analogue" in the context of this invention means a residue, particularly an amino acid residue, having a structural character (sterical/chemical) similar to that of E (or to phosphorylated S). The term "E analogue" or "phosphorylated S analogue" particularly refers to a(n) (amino acid) residue having a chemical structure and/or "behavior" within a 3-dimensional (tri)peptide structure (QXP) which is more similar to that of E (or phosphorylated S) itself than to that of any other amino acid residue, like, for example, non-phosphorylated S.

The skilled person is readily in the position to deduce which particular compounds fall under the meaning of the terms "E analogue" and "phosphorylated S analogue", i.e. which compounds are, structurally and/or functionally, more closely related to E or phosphorylated S itself, than to any other amino acid, in particular to non-phosphorylated S.

Particular E analogues or phosphorylated S analogues in accordance with the present invention may be those, the C-side chain of which is shortened or elongated as compared to E or phosphorylated S itself (for example by (a) —$CH_2$-residue(s)). The C-residues of the C-side chain may be up to 5, preferably up to 3, more preferably 1 or 2. One example of such an analogue having a shortened or elongated C-side chain is an analogue with the basic structure of E but having one additional —$CH_2$-residue inserted into the C-side chain.

Particular examples of X, in particular of an E analogue, in accordance with the present invention are phosphorylated S (preferably $S_{thiophosphate}$), D (Aspartic acid) (or a D analogue), Y (Tyrosine) (or a Y analogue) and T (Threonine) (or a T analogue) (e.g. T thiophosphate). Preferred examples of X or of an E analogue are $S_{thiophosphate}$ and phosphorylated S. In principle, E and the E analogues described herein may also be seen as phosphorylated S analogues, D analogues, Y analogues and T analogues. What has been generally said with respect to "analogues" herein elsewhere, applies here, mutatis mutandis. Preferred E analogues are amidated E analogues, for example amidated D, amidated Y and amidated T. A particularly preferred E analogue is amidated E.

The E analogues, and the other amino acid analogues described herein, share the functional feature that, when they replace the E residue (or the corresponding other residue) in the QEP motive of the disclosed (poly)peptides, or are inserted as the X in the QXP motive of the disclosed (poly)peptides, respectively, the resulting (poly)peptide is capable of reducing/inhibiting SGLT1-mediated glucose and/or galactose uptake into a cell under the high-sugar conditions described herein, in particular in the presence of an increased concentration of glucose and/or galactose.

In principle, what has been said with respect to E and X, supra, also applies to any other (amino acid) residue which might replace Q and/or P in QEP to form a QEP derivative referred to herein. Examples of other (amino acid) residues which might replace Q and/or P in the herein described QEP derivatives, for example Q analogues and/or P analogues, are N (or another N analogue) and/or $_{hydroxy}$P (or another P analogue).

Particular examples of QEP derivatives to be employed in accordance with the present invention are selected from the group consisting of:

(a) $QS_{thiophosphate}$-P;
(b) QSP, wherein the S residue is phosphorylated;
(c) QDP;
(d) QYP;
(e) QTP;
(f) QTP, wherein the T residue is phosphorylated;
(g) $QT_{thiophosphate}$-P;
(h) NEP;
(i) NSP, wherein the S residue is phosphorylated;
(j) $NS_{thiophosphate}$-P;
(k) NDP;
(l) QE-$_{hydroxy}$P;
(m) QD-$_{hydroxy}$P;
(n) QS-$_{hydroxy}$P, wherein the S residue is phosphorylated;
(o) $QS_{thiophosphate-hydroxy}$P;
(p) any one of (a) to (o) having its middle/second amino acid residue replaced by another E analogue or by another phosphorylated S analogue;
(q) any one of (a) to (p) having its first amino acid residue replaced by another Q analogue; and
(r) any one of (a) to (q) having its last amino acid residue replaced by another P analogue.

QEP derivatives and QEP as referred to herein also encompass secondary forms of the QEP amino add sequence, e. g. forms comprising D- and L-isoforms of comprised amino acid residues, natural and unnatural salts and secondary forms with modifications like acetylation, amidation, methylation, glycosylation and/or phosphorylation and substances with similar or the same mass-spectrometrical characteristics. For example, acetylated and, in particular, amidated forms of the QEP amino acid sequence may have the same, and even improved effects in accordance with the present invention, e.g. the same or improved effects on glucose and/or galactose uptake, as the corresponding non-acetylated or non-amidated forms. Accordingly, also secondary modifications/forms of the herein defined (poly) peptides are part of this invention. In principle, a QEP derivative as referred to herein also encompasses the herein described tripeptides itself (like QEP), optionally with (a) (small) modification(s) at one or more of their reactive group(s). A particularly preferred form of a QEP derivative or QEP, or a (poly)peptide comprising the same, is an amidated QEP derivative or QEP, or a (poly)peptide comprising the same. In particular, the E or E analogue as comprised in such a QEP derivative, QEP, or (poly)peptide is envisaged to be amidated.

QEP or QEP derivatives or (poly)peptide consisting of or comprising the same may be made hydrophobic. Such a hydrophobic peptide is able to cross (biological) membranes. For instance, QEP may be coupled with antennapedia proteins (or fragments thereof) in order to obtain corresponding hydrophobic forms; see also Derossi (1994), J. Biol. Chem. 269, 10444-10450.

In one embodiment, QEP or a QEP derivative encompasses all such tripeptides or similar substances that can function as substrates for (human) peptide-proton symporters, e.g. (h)PEPT1 (and/or (h)PEPT2). The molecular structure of such tripeptides or substances can be deduced by the skilled person and are described in, for example, Daniel (2004), Pflügers Arch. 447, 610-618. Corresponding screening assays for the function of such tripeptides or substances as substrates for (h)PEPT1 (and/or (h)PEPT2) can readily be deduced by the skilled artesian from, for example, Daniel (2004), loc cit.

It is to be understood, that the embodiments characterized herein for the QEP peptide also apply to the herein described QEP derivatives, in particular to the herein exemplified QEP derivatives.

In general, it is envisaged that a QEP derivative in accordance with the invention has at least one of the following features, in particular under high-sugar condition:

(a) the function/activity of (h)RS1 in its active state (but not inhibiting OCT2, CNT1 and CNT3) (see also sections (A) to (D), infra;
(b) transportable by a peptide transporter like (h)PEPT1;
(c) binding to/interacting with ODC (in vive or in vitro); and
(d) inhibiting/reducing ODC expression/activity (in vivo or in vitro).

In the context of the present invention, "RS1" particularly refers to a polypeptide that has the function/activity of the naturally occurring RS1 in its active state. For instance, such "RS1" may be the (full length) human RS1 (hRS1), for example as characterized by an amino acid sequence of SEQ ID NO: 2 or by a fragment thereof having the function/activity of the naturally occurring hRS1 in its active state.

The regulatory protein RS1 is known in the art (see, e.g. Veyhl (1993), J. Biol. Chem. 268, 25041-25053; Koepsell (1994), J. Membrane Biol. 138, 1-11; Lambotte (1996), DNA and Cell Biology 15, 9, 769-777; Valentin (2000), Biochimica et Biophysica 1468, 367-380; Korn (2001), J. of Biological Chemistry 276, 48, 45330-45340; Veyhl (2003), J. Membrane Biol. 196, 71-81; Osswald (2005), Mol Cell Biol. 25, 78-87). Particularly known are the human RS1 (hRS1), Acc. No. NM_006511 or X82877; the porcine RS1, Acc. No. NM_213793 or X64315; the mouse RS1, Acc. No. Y11917 and the rabbit RS1, Acc. No. X82876. The human RS1 (Acc. No. NM_006511, X82877; Lambotte (1996), DNA and Cell Biology 15, 9, 769-777) consists of 617 amino acids with 74% amino acid identity to RS1 from pig (Acc. No. NM_213793, X64315, Veyhl (1993), J. Biol. Chem. 268, 25041-25053.). Other homolog RS1 proteins are from rabbit (Acc. No. X82876) or mouse (Acc. No. Y11917). hRS1 is illustratively shown in SEQ ID No. 2 which is encoded by a nucleic acid molecule as shown in SEQ ID No. 1. Within the human RS1, the SDSDRIEP motive as mentioned herein is from amino acid position 43 to 50 and the QSP motive as mentioned herein is present in the hRS1 two times, namely from amino acid positions 19-21 and 91-93 (see SEQ ID No. 2 and 6). RS1 (i) inhibits the human sodium-D-glucose cotransporter hSGLT1 and some other plasma membrane transporters posttranscriptionally (Veyhl (2003), J. Membrane Biol. 196, 71-81), (ii) is located within the cytosol as well as within nuclei (Osswald (2005), Mol Cell Biol. 25, 78-87), and (iii) inhibits transcription of SGLT1 (Korn (2001), J. Biol. Chem. 278, 45330-45340).

For example, the active state (h)RS1 function/activity in accordance with the present invention is at least one of the following functions/activities:
(A) the (highly selective) reduction/inhibition of SGLT expression and/or activity (in particular the Na+-D-glucose and/or galactose cotransport);
(B) the (highly selective) reduction/inhibition of glucose and/or galactose uptake into the small intestine (in particular as medicated by SGLT1);
(C) the binding to/interacting with ODC (in vitro or in vivo); and
(D) the inhibiting/reducing ODC expression/activity.

As mentioned, however, the herein described (poly)peptides differ from the endogenous (h)RS1 in that they exhibit the above functions/activities even under high-sugar conditions, in particular in the presence of high/an increased (intracellular) glucose and/or galactose concentration.

The (highly selective) reduction/Inhibition of SGLT1 expression and/or activity ((A), supra) and/or of glucose and/or galactose uptake into the small intestine ((B), supra) may be at least 10%, 20%, 30%, 40%, 50%, 60%, 70%, 75% or 80% as compared to the common SGLT1 expression/activity and glucose/galactose uptake, respectively, under a high-sugar condition/situation (when, for example, native/endogenous RS1 is inhibited).

The skilled person is readily in the position to test whether a given (poly)peptide (for example a QEP derivative) has active state (h)RS1 function/activity, in particular under high-sugar conditions, by methods known in the art (e.g. WO 2006/105913 and WO 2006/105912) or provided herein and in the appended examples.

In order to identify and/or verify a useful QEP derivative in accordance with the present invention, further several art-known techniques may be employed. These techniques are, for example, in-gel digestions, electroelution procedures, microsequencing, amino acid analysis, Edman-sequencing or mass spectroscopy. Also crystalographic methods may be employed. Some techniques directly start from gel(s), others need a transfer to membranes by blotting. The first group comprises, inter alia, coelectrophoresis, internet comparison of position, peptide mapping by SDS-PAGE (Cleveland (1977), J. Biol. Chem. 252, 1102), protein elution and MALDI-MS or N-terminal sequencing by Edman degradation (Edman (1950), Acta Chem. Scand. 4, 283), enzymatic in-gel digestion, analysis of peptides directly in the mixture by mass spectrometry, peptide mass fingerprinting (Pappin (1993), Curr. Biol. 3, 327), ESI-MS (electrospray-ionization-MS), MALDI PMF and/or MALDI PDS (like, e.g. PSD-MALDI-MS (Spengler (1992), Rapid Commun. Mass Spectrom. 6, 105)). As a matrix for MALDI-MS, nicotinic acid, 2,5-dihydroxy benzoic acid or alpha-cyano-4-hydroxyciannamic acid may be used.

In a specific aspect, the (poly)peptide to be employed in accordance with the invention (and which comprises at least a QEP or a QEP derivative) consists of at most 100 amino acids, in particular, consecutive amino acids, more specifically, of at most 78 or at most 83 amino acids, in particular, consecutive amino acids. For example, the (poly)peptide may consist of at most 3, 6, 11, 14, 20, 40, 60, 75 or 80 (consecutive) amino acids. However, in general, longer amino acids are also envisaged.

A particular (poly)peptide to be employed in accordance with the invention (and which comprises at least a QEP and/or a QEP derivative), may be selected from the group consisting of:
(a) a polypeptide which comprises or consists of the regulatory domain of RS1 (RS1-Reg) having at least its first/N-terminal glutamine-serine-proline (QSP) motive replaced by the amino acid sequence QEP or by a derivative thereof as defined herein;
(b) a polypeptide which comprises or consists of a polypeptide being at least about 25%, 35%, 50%, 60%, 70%, 85%, 90%, 95%, 98%, 99% or 100% identical to RS1-Reg and having at least the first/N-terminal QSP motive of RS1-Reg replaced by the amino acid sequence QEP or by a derivative thereof as defined herein;
(c) a polypeptide which comprises or consists of a polypeptide encoded by a nucleic acid molecule hybridizing under stringent conditions to the complementary strand of a nucleic acid molecule encoding RS1-Reg, said polypeptide having at least the first/N-terminal QSP motive of said RS1-Reg replaced by the amino acid sequence QEP or by a derivative thereof as defined herein;
(d) a polypeptide which comprises or consists of a polypeptide of Formula I:

$$x_n\text{-Q-E-P-}x_m \quad (I)$$

wherein x is any amino acid, n is an integer of 0-3, preferably 3, and m is an integer of 0-77 (preferably 77) or an integer of 0-72 (preferably 72);
(e) a polypeptide which comprises or consists of the polypeptide of Formula I having the QEP motive replaced by a derivative thereof as defined herein;
(f) a polypeptide which comprises or consists of a fragment of the polypeptide of any one of (a) to (e), wherein said fragment comprises the amino acid sequence QEP or the derivative thereof as defined herein.

The herein described RS1-Reg may be mouse RS1-Reg (mRS1-Reg) or, preferably, human RS1-Reg (hRS1-Reg). hRS1-Reg may have an amino acid sequence as depicted in SEQ ID NO. 6 and mRS1-Reg may have an amino acid sequence as depicted in SEQ ID NO. 8. A particular polypeptide to be employed in accordance with the invention may be a polypeptide which comprises or consists of a polypeptide being at least about 24.1%, 36.2%, 48.2%, 60.3%, 72.3%, 84.4%, 90.4%, 96.4% or even 100% identical (the higher values are preferred) to hRS1-Reg (for example as depicted in SEQ ID NO: 6) or at least about 25.6, 38.5%, 51.3%, 64.1%, 76.9%, 89.7, 96.2% or even 100% identical (the higher values are preferred) to mRS1-Reg (for example as depicted in SEQ ID NO: 8) and having at least the first/N-terminal QSP motive of the hRS1-Reg and mRS1-Reg, respectively, replaced by the amino acid sequence QEP or by a derivative thereof as defined herein. As to hRS1-Reg, the above values of percentage correspond to at least about 20, 30, 40, 50, 60, 70, 75, 80 and 83 amino acid residues, respectively. As to mRS1-Reg, the above values of percentage correspond to at least about 20, 30, 40, 50, 60, 70, 75 and 78 amino acid residues, respectively.

Particular examples of the polypeptide to be employed in accordance with the invention are mRS1-Reg(S19E) and, preferably, hRS1-Reg(S20E), in particular mRS1-Reg (S19E) and hRS1-Reg(S20E) as depicted in SEQ ID NOs: 10 and 9, respectively.

In the context of the present invention, "hybridizing" means that hybridization can occur between one nucleic acid molecule and another (complementary) nucleic acid molecule. Hybridization of two nucleic acid molecules usually occurs under conventional hybridization conditions. In the context of the invention, stringent hybridization conditions are preferred. Hybridization conditions are, for instance, described in Sambrook and Russell (2001), Molecular Cloning: A Laboratory Manual, CSH Press, Cold Spring Harbor, N.Y., USA. In a particular embodiment, "hybridizing" means that hybridization occurs under the following conditions:

| Hybridization buffer: | 2 × SSC, preferably 1 × SSC; 10 × Denhardt solution (Fikoll 400 + PEG + BSA; ratio 1:1:1); 0.1% SDS; 5 mM EDTA; 50 mM Na$_2$HPO$_4$; 250 µg/ml of herring sperm DNA; 50 µg/ml of tRNA; or 0.25M of sodium phosphate buffer, pH 7.2; 1 mM EDTA 7% SDS |
|---|---|
| Hybridization temperature T | = 60° C., preferably 65° C. |
| Washing buffer: | 2 × SSC, preferably 1 × SSC, more preferably 0.1 × SSC; 0.1% SDS |
| Washing temperature T | = 60° C., preferably 65° C. |

A preferred version of Formula I as depicted above is Formula Ia:

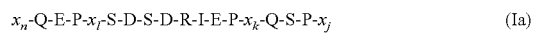

$x_n$-Q-E-P-$x_l$-S-D-S-D-R-I-E-P-$x_k$-Q-S-P-$x_j$     (Ia)

wherein x is any amino acid, n is an integer of 0-3 (preferably 3), l is an integer of 0-21 (preferably 21), k is an integer of 0-40 (preferably 40) or an integer of 0-35 (preferably 35) and j is an integer of 0-5 (preferably 5).

In the polypeptide of Formula Ia, one or more of the S residues of the SDSDRIEP (SEQ ID NO:35) and QSP motive may be replaced by E or an E analogue as described herein. A preferred S→E replacement is the replacement of the 2$^{nd}$ S in the SDSDRIEP (SEQ ID NO: 35) motif (the S45 of mRS1). Hence, preferred polypeptides of Formula I or Ia comprise SDEDRIEP (SEQ ID NO:35). An example of such a polypeptide is hRS1-Reg(S45E) as described herein and in the appending examples.

In the polypeptide of Formula I and Ia one or more of the QEP (and QSP) motive may be replaced by a QEP derivative as described herein.

In any of Formulas I and Ia, "$x_n$" may be XSG (X is any amino acid), preferably PSG or, more preferably, SSG and/or "$x_m$" may be XVGXPXSLARSVSASXCXIK-PXDXXXIEXXAXXAXKASAEFQXNSXKXXXXX-LQXLXDXAS SAX(HAPTD)QSXAMPXX (X is any amino acid), preferably EVGSPTSLARSVSASVCAIK-PGDPNSIESLAMEATKASAEFQTNSKKTDPPPLQVLP-DLAS SAEQSLAMPFH or, more preferably, DVGNPMSLARSVSASVCPIKPSDSDRIEPKAVKA-LKASAEFQLNSEKKEHLSLQDLSDHA SSADHAPT-DQSPAMPMQ, or an amino acid stretch sharing at least 10, 20, 30, 40, 50, 60, 70 or 75 identical amino acid residues with any of the above amino acid stretches. "$x_l$" may be XVGXPXSLARSVSASXCXIKP (X is any amino acid), preferably EVGSPTSLARSVSASVCAIKP or, more preferably, DVGNPMSLARSVSASVCPIKP, or an amino acid stretch sharing at least 5, 10, 15 or 20 identical amino acid residues with any of the above amino acid stretches. "$x_k$" may be XAXXXAXKASAEFQXNSXKXXXXXLQX-LXDXASSAX(HAPTD) (X is any amino acid), preferably LAMEATKASAEFQTNSKKTDPPPLQVLPDLASSAE or, more preferably, KAVKALKASAEFQLNSEKKE-HLSLQDLSDHASSADHAPTD, or an amino acid stretch sharing at least 10, 20, 30, 35 or 38 identical amino acid residues with any of the above amino acid stretches. "$x_j$" may be AMPXX (X is any amino acid), preferably AMPFH or, more preferably, AMPMQ, or an amino acid stretch sharing at least 1, 2, 3 or 4 amino acid stretches with any of the above amino acid stretches. "$x_j$" or "$x_n$" may comprise at least 1, 2, 3, 4, 5, 6, 7, 8, 9 or 10 amino acid residues, preferably consecutive amino acid residues of the respective amino acid sequence stretches of hRS1 or mRS1 (amino acids 94-103 and 88-97, respectively, and amino acids 9-18 and 8-17, respectively).

The polypeptide or the fragment of the polypeptide referred to herein may at least consist of 3, 4, 5, 6, 7, 8, 9, 10, 15, 20, 30, 40, 50, 60, 70, 75 or 80 amino acids, preferably consecutive amino acids. In any case, the polypeptide or polypeptide fragment comprises at least one QEP motive or QEP derivative. The polypeptide or polypeptide fragment may further comprise (an) additional QEP, QSP, SDSDRIEP and/or SDEDRIEP motive(s). Preferably, the polypeptide or polypeptide fragment comprises one QEP, one SDSDRIEP or one SDEDRIEP and one QSP motive (more preferably in this order). Moreover, the polypeptide or polypeptide fragment may comprise at least one QEP motive or QEP derivative and, in addition, one or more of "$x_n$", "$x_l$", SDSDRIEP or SDEDRIEP, "$x_k$", QSP, "$x_j$" and "$x_m$", preferably in an order which reflects the order in Formula I or Ia, supra.

It is also envisaged herein that modifications of RS1-Reg (e.g. of hRS1-Reg(S20E) or mRS1(S19E)) in which additional serine residues in (a) predicted phosphorylation site(s) is/are mutated to, for example, alanine or an alanine analog (preventing phosphorylation) or to glutamate or a glutamate analog (mimicking phosphorylation) are made.

Hence, in one embodiment, the S residue of one or more (predicted) phosphorylation site(s) of the polypeptide or the fragment thereof as described herein may be mutated to alanine (A), to glutamic acid (E), to aspartic acid (D), to phosphorylated S, to thiophosphorylated S, to phosphorylated T and/or to thiophosphorylated T, and/or to another E analogue, D analogue or phosphorylated S analogue. What has been said with respect to the respective analogue herein elsewhere also applies here, mutatis mutandis. Particular (predicted) phosphorylation sites are known in the art. Such (predicted) phosphorylation sites may be those of RS1-Reg. Particular examples of (predicted) phosphorylation sites of hRS1-Reg and mRS1-Reg are listed in FIGS. 1 and 6. In this context, the most preferred phosphorylation sites are those present in the SDSDRIEP motive, in particular the phosphorylation site which comprises the $2^{nd}$ S residue of this motive.

In one embodiment, the herein described polypeptide comprises or consists of the entire/full length RS1 having at least its first/N-terminal glutamine-serine-proline (QSP) motive replaced by the amino acid sequence QEP or by a derivative thereof as defined herein. The RS1 may be human RS1 (hRS1) or mouse RS1 (mRS1). The hRS1 may have an amino acid sequence as depicted in SEQ ID NO. 2 and the mRS1 may have an amino acid sequence as depicted in SEQ ID NO. 4. However, it is preferred in the context of the present invention that the herein described polypeptide does neither consist of nor does comprise the entire/full length RS1.

In particular, it is envisaged that any of the above- (or herein elsewhere-) defined and described (poly)peptides and fragments (and any of the other active compounds), e.g. the QEP, the QEP derivatives, the (poly)peptides comprising QEP and/or (a) QEP derivative(s), the fragments thereof, the nucleic acid molecules encoding the same, the vectors comprising the nucleic acid molecules, are capable of
(i) reducing/inhibiting glucose and/or galactose (SGLT1-mediated) uptake into a cell under high-sugar conditions, in particular, in the presence of an increased concentration of glucose and/or galactose); and/or
(ii) any of the other features and/or functions/activities as described herein above with respect to the QEP derivative and the active state (h)RS1.

It is further envisaged that the (poly)peptide or fragment thereof described herein binds to and/or interacts with (in vivo or in vitro) ornithine decarboxylase (ODC; for example ODC as accessible under UnProtKB: P11926). More particular, it is envisaged that the (poly)peptide described herein is capable to reduce/inhibit ODC expression and/or activity.

In accordance with the invention, the use of a protein or (poly)peptide (or other compound) which can be processed into any of the herein described (poly)peptide or fragment is also envisaged.

"Can be processed into" means that the protein or (poly) peptide, which may comprise additional (amino acid) residue(s), can be dissected, cleaved, shortened, digested or otherwise (chemically) modified by a corresponding process/reaction, so that at least one QEP or QEP derivative (or (poly)peptide or fragment) is released/obtained. The corresponding process may be chemically or enzymatically driven. An example for an enzymatically driven process is a proteolytical driven process, i.e. a process during which proteases cleave the protein or (poly)peptide so that at least one QEP or other (poly)peptide is released/obtained.

The "processing" may occur in the gastrointestinal tract of a subject (for example by (proteolytic) cleavage in the stomach or in the small intestine). This means that the (poly)peptide of the present invention (for example in form of the herein disclosed pharmaceutical composition or comestible) may be administered in form of a precursor. i.e. In form of a protein or (poly)peptide comprising (an) (amino acid) residue(s) in addition to the QEP stretch or its derivative or comprising several QEP stretches or its derivatives. Said precursor is then (proteolytically) processed into the QEP stretch(es) or its derivative(s). Without being bound by theory, said QEP stretch(es) or derivative(s) may then be taken up by PEPT1 and exert its effects on glucose/galactose uptake within the cell.

It is particularly envisaged that the particular (amino acid) structure of the longer protein or (poly)peptides provided herein enables the processing of said peptides into QEP(s) or its derivative(s). For this purpose, the longer proteins/(poly) peptides may have a pattern of alternating (proteolytically) cleavable and non-proteolytically cleavable (peptide) bonds, wherein the cleavable bonds are between/outside the comprised QEP stretch(es) or derivative(s) and wherein the non-cleavable bonds are within the same. Examples of corresponding peptides and bonds are provided herein elsewhere.

Proteins and (poly)peptides which can be processed in accordance with this invention may, for example, comprise one, two, three, four, five, six, seven, eight, nine or ten additional amino acid residues. However, also longer amino acid stretches, comprising the herein defined QEP or its derivative are envisaged. Accordingly, the protein or (poly) peptide may comprise at least 3, 5, 7, 9, 11, 13, 14, 15, 16, 17, 18, 19, at least 20, at least 30, at least 40, at least 50, at least 60, at least 70, at least 80, at least 90 or at least 100 amino acid residues. Also at the most 150 amino add residues, preferably at the most 120 amino acid residues are envisaged. However, in accordance with this invention, smaller (poly)peptides of, for example, 3 to 12 amino acid residues are preferred, whereby 3 to 10 amino acid residues are more preferred.

In accordance with the present invention, the protein or (poly)peptide which can be processed into QEP or a derivative thereof may also be a fusion construct, for example a fusion protein. These fusion construct/protein and corresponding embodiments are described in more detail below.

In accordance with this invention, it is also envisaged that the "peptide" comprises the QEP motive (or a derivative thereof) in form of repeats/tandems. Accordingly, also (synthetic or recombinant) peptides are envisaged which are or which comprise motives like QEPQEP, QEPQEPQEP, etc. Said QEP motive may be repeated 2, 3, 4, 5, 6, 7, 8, 9 or more times within the (poly)peptide. The repeated stretches may be interrupted by spacers/linkers of, for example, other amino acid residues. Accordingly, the repeated sequences may be of the format "QEPXQEP", "QEPXQEPXQEP", etc. In principle, "X" may represent any (amino acid) residue and any number of (amino acid) residues. For example, "X" is selected from the group consisting of the amino acid residues A (alanine), K (lysine) or R (arginine). It is preferred that the number of linker/spacer amino acid residues is at least one. It is more preferred that the number of linker/spacer amino acid residues is 2 or 3. The number may also be 1, 4, 5, 6, 7, 8, 9 or 10, or even more. It is particularly envisaged, that the peptides consisting of or comprising repeats/tandems of Q-E-P or a derivative thereof may also comprise more than 150 amino acids.

The "X" of the (poly)peptide as described above may be a cleavable site, for example a site cleavable by hydrolysis (e.g. catalyzed by hydrolases). In particular, "X" may be S—S. Furthermore, "X" may be an ester bond which, for instance, may be cleavable by corresponding esterases. It is particularly envisaged that the spacers/linkers, like the "X", interrupting the QEP motives (or derivatives thereof) render the corresponding (poly)peptide comprising these spacers/ linkers and motives accessible to be processed into the QEP motives (or derivatives thereof) in accordance with the present invention. One particular example of "X" is or comprises PS or SP, or any other of the spacers/linkers as described in WO 2008/155134 ("second domain").

In the (poly)peptide as described herein, the QEP motive (or derivative thereof), or repeats/tandems thereof, may be attached to further amino acids, heterologous peptides and/or heterologous proteins (see, for example, the "second domain" as disclosed in WO 2008/155134). Said further amino acids, peptides or proteins may also comprise one or more of RS1 fragments like those disclosed in WO 2006/105913 and WO 2006/105912 as well as all possible combinations of said RS1 fragments with the herein described QEP peptide or derivative thereof. Furthermore, said further amino acids, heterologous peptides and/or heterologous proteins may comprise, derived from and/or consisting of domains having additional functionalities, like, e. g. domains providing further pharmacological effects or specific tags for facilitating protein purification, like, e.g., His-tags. Accordingly the (poly)peptide or QEP stretch or derivative thereof as defined herein may also be part of a fusion polypeptide or a fusion protein. In accordance with the present invention, said fusion polypeptide or fusion protein comprising the peptide or QEP motif or derivative thereof as defined herein may also comprise more than 100 or more than 150 amino acids.

The term "QEP" or "QEP derivative" also relates to QEP or its derivatives having at least one, preferably both internal peptide bond(s) substituted by a (covalent) bond, for example, which is not (proteolytically) cleavable, for example which is not cleavable when the corresponding protein or (poly)peptide is processed into said QEP or its derivative in accordance with this invention. Such covalent bound may be, for instance, selected from the group consisting of —CH2-CH2-, —CH(OH)—CH2-, —CH2-CH(OH)—, —CH(OH)—CH(OH)—, —C=O—CH2-, —CH2-C=O—, —CH(OH)—C=O—, —CH=CH—, —C(OH)=CH2-, —CH=C(OH)—, C(OH)=C(OH)—, —N=CH—, —N=C(OH)—. Preferably, such covalent bound may be, for instance, selected from the group consisting of —CH2-C=O—, —CH(OH)—C=O—, —CH=CH—, —CH—C(OH)—, C(OH)=C(OH)—, —N=C(OH)—. Such (a) bond(s) renders the Q-E-P or its derivative inert, for example, against further (proteolytic) digestion and, therefore, keep(s) its functionality within the gastrointestinal tract.

As pointed out above, the inventive (poly)peptide may also comprise several QEP motives or derivatives thereof, wherein said QEP motives are directly linked to each other, e.g. in the format "( . . . )QEPQEP( . . . )", or wherein said QEP motives are separated by linker/spacer structures and/or additional amino acid residues, e.g. in the format "( . . . )QEPXQEP( . . . )", wherein "X" denotes at least one additional (amino acid) residue. In such peptides, the above-mentioned and defined (proteolytically) non-cleavable (peptide/covalent) bonds are preferably comprised between "Q" and "E" and/or between "E" and "P" of the QEP motif or between the corresponding (amino acid) residues of the corresponding QEP derivative. The bond between "X" and "Q" and/or between "P" and "X" is preferably a (peptide/covalent) bond which is (proteolytically) cleavable, for example when the corresponding "peptide" is processed into the Q-E-P stretch or its derivative in accordance with the invention. Accordingly, the longer (poly)peptide as defined herein is envisaged to be proteolytically cleaved in vivo (for example after administration into the stomach by gastric juices, in the (small) intestine or in the blood stream), whereby the proteolytically non-cleavable bonds comprised between "Q" and "E" and "E" and "P" are not cleaved, leading to a "proteolytically inert" QEP tripeptide which is particularly useful in the context of the means, methods and uses of the present invention. As mentioned above, the above-described embodiments are not restricted to the distinct QEP tripeptide, but also to derivatives thereof.

It is particularly envisaged for the longer proteins or (poly)peptides defined herein (which, for example, cannot be taken up by PEPT1 and/or PEPT2) that the comprised QEP peptide(s) or derivative(s) thereof have such inert bonds are, hence, not (proteolytically) cleavable. These inert QEP peptides may then remain intact (for example during the passage of the stomach and/or (small) intestine), whereas the (amino acid) residues/amino acid stretches flanking said peptides are (proteolytically) cleaved of. This leads to QEP stretches or derivatives thereof consisting of exactly 3 amino acids within the gastrointestinal tract. This kind of QEP tripeptides can then be transported, e.g. by PEPT1 and/or PEPT2, into those cells in which they are desired to be active.

In principle, the meaning of "sugar" in the context of the invention encompasses any poly-, di- or monosaccharides. More specifically, "sugar" means monosaccharides. Even more specifically, "sugar" means glucose and/or galactose, preferably D-glucose and/or D-galactose, more preferably (free) unphosphorylated D-glucose and/or (free) unphosphorylated D-galactose. Without being bound by theory, monosaccharides and, in particular, (free) unphosphorylated D-glucose and/or (free) unphosphorylated D-galactose are the preferred substrates of SGLT1 and are responsible for the reduction/blockage of the SGLT1-inhibitory effect of RS1 and the regulatory protein RS1 fragments as described in WO 2006/105913 and WO 2006/105912. In this context, the most relevant "sugar" is (free) unphosphorylated D-glucose. Evidence has been provided herein in the appended examples that it is (free) unphosphorylated D-glucose which is responsible for the reduction/blockage of the SGLT1-inhibitory effect of RS1 within the enterocytes of the small intestine. In particular, it has been demonstrated herein and in the appended examples that AMG (which is not phosphorylated) causes such reduction/blockage.

In a specific aspect, a "sugar" is capable to act as a substrate of SGLT1 and, hence, can be internalized by an SGLT1-mediated transport into a cell like, for example, into an enterocyte. In a preferred embodiment, any of the herein described "sugar" has this feature.

However, sugars like glucose and/or galactose are not necessarily ingested as such but rather derived/released from other (more complex) sugars and/or other carbohydrates like saccharose, glycogen or starch. In particular, saccharose is known to be the most relevant "sugar" in (mal)nutrition. The meaning of "sugar" also encompasses sugars like saccharose, in particular if "sugar" in an energy-rich meal is meant.

In principle, the at least one part of the patient's gastrointestinal tract is such a part which is capable to absorb sugars like glucose and/or galactose and the epithelial cells of which express SGLT1, respectively. In particular, the at least one part of the patient's gastrointestinal tract is the small intestine, even more particular, the jejunum. In the context of the invention, particular epithelial cells of the at least one part of the patient's gastrointestinal tract are the enterocytes.

As mentioned, it is particularly intended in accordance with the invention to administer the active compounds or the pharmaceutical composition of the invention under a high-sugar condition/situation, more particular, under a high-sugar condition/situation at and/or, preferably, in the epithelial cells of at least one part of the patient's gastrointestinal tract. In this context, a high-sugar condition/situation is to be seen as a condition/situation where the endogenous/native regulatory protein RS1 (and peptides which represent the endogenous/native regulatory protein RS1; e.g. as disclosed in WO 2006/105912 and WO 2006/105913) is predominantly present in the non-phosphorylated form and, hence, little active or not active at all. Active, in this context, particularly means reducing/Inhibiting the activity of SGLT1. In particular, a high-sugar condition/situation is a condition/situation where the concentration of glucose and/or galactose is increased, in particular, in the lumen, at and/or, preferably, in the epithelial cells of the at least one part of the patient's gastrointestinal tract.

In principle, a high-sugar condition/situation and a condition/situation where the concentration of (a) sugar(s) like glucose and/or galactose is increased is a condition/situation, where (a) sugar(s) is present in a higher amount or at a higher concentration as compared to a normal-sugar condition/situation or, preferably, as compared to a fasting condition/situation or a condition/situation of uninebration and a low-sugar condition/situation, respectively. The skilled person is readily able to differentiate between a high-sugar, normal-sugar and a low-sugar condition/situation in accordance with the invention. For example, a high-sugar condition/situation occurs during or after an energy-rich meal. For example, a low-sugar condition/situation occurs during or after an energy-low meal or during fasting periods or during periods of uninebration, for example in between (energy-rich) meals or during the night. For example, a normal-sugar condition occurs during or after a meal having a normal energy content. For example, a high-sugar condition/situation is a condition/situation where the amount or concentration of sugar is increased, for example in the lumen, at and/or, preferably, in the epithelial cells of the at least one part of the patient's gastrointestinal tract, more than about 10%, 20%, 30%, 40%, 50%, 60%, 70%, 80%, 90%, 100%, 200%, 300%, 500%, or 1000%, as compared to a normal- or low-sugar condition/situation.

Increased concentrations of (a) sugar(s) like glucose and/or galactose in the lumen and/or the epithelial cells of at least one part of the gastrointestinal tract (and/or in the blood and/or in the urine are particular conditions/situations which represent high-sugar conditions/situations. In this context, it is particularly envisaged that the increased concentrations of (a) sugar(s) like glucose and/or galactose are within the physiological range.

Increased concentrations of (a) sugar(s) like glucose and/or galactose in the epithelial cells of the at least one part of the patient's gastrointestinal tract may be concentrations of $\geq 10$ µM, $\geq 20$ µM, $\geq 30$ µM, $\geq 40$ µM, $\geq 50$ µM, $\geq 60$ µM, $\geq 80$ µM or $\geq 100$ µM. Upper limits of concentrations of (a) sugar(s) like glucose and/or galactose in the mentioned epithelial cells, even under a high-sugar condition, may be $\leq 250$ µM, $\leq 450$ µM, $\leq 1$ mM, $\leq 5$ mM, $\leq 10$ mM, $\leq 50$ mM, $\leq 100$ mM. In principle, any possible range of increased concentrations of (a) sugar(s) like glucose and/or galactose as defined by any possible combination of any of the above lower limits and any of the above upper limits is envisaged. Particular ranges are from about 10 µM to about 100 mM, from about 10 µM to about 10 mM, from about 10 µM to about 5 mM, from about 10 µM to about 1 mM, from about 50 µM to about 250 µM, from about 50 µM to about 450 µM, preferably from about 50 µM to about 1 mM, from about 50 µM to about 5 mM, from about 50 µM to about 10 mM and from about 50 µM to about 100 mM.

Increased concentrations of (a) sugar(s) like glucose and/or galactose in the lumen of the at least one part of the patient's gastrointestinal tract may be a concentration of $\geq 10$ µM, $\geq 50$ µM, $\geq 100$ µM, $\geq 500$ µM, $\geq 1$ mM and $\geq 5$ mM. Upper limits of concentrations of (a) sugar(s) like glucose and/or galactose in the lumen of the at least one part of the patient's gastrointestinal tract, even under a high-sugar condition, may be $\leq 500$ µM, $\leq 1$ mM, $\leq 10$ mM, $\leq 25$ mM and $\leq 100$ mM. In principle, any possible range of increased concentrations of (a) sugar(s) like glucose and/or galactose as defined by any possible combination of any of the above lower limits and any of the above upper limits is envisaged. Particular ranges are from about 10 µM to about 100 mM, from about 10 µM to about 10 mM, from about 10 µM to about 1 mM, from about 50 µM to about 25 mM, from about 10 µM to about 25 mM and, preferably, from about 5 mM to about 25 mM.

In principle, (a) sugar(s) like glucose and/or galactose in the lumen of the at least one part of the patient's gastrointestinal tract are transported into the epithelial cells of this tract and thereby are accumulated to a factor of about 10 to 20. However, most of the transported sugar(s) will rapidly be phosphorylated and, hence, most of the accumulated sugar(s) is (are) phosphorylated. However, as mentioned, the most relevant, i.e. modulatory, sugar(s) with respect to a high-sugar condition/situation in accordance with the invention is (are) unphosphorylated sugar(s).

In principle, a high-sugar condition/situation, for example in the lumen and/or epithelial cells of at least one part of the patient's gastrointestinal tract, may lead, may be going to lead or may be expected to lead also to a high-sugar condition/situation in the patient's blood and/or urine. Hence, in principle, the high-sugar condition/situation in accordance with the invention also encompasses a condition/situation where the concentration of (a) sugar(s) like glucose and/or galactose is, is going to be or is expected to be increased in the patient's blood and/or urine.

Increased concentrations of (a) sugar(s) like glucose and/or galactose in the patient's blood may be concentrations of $\geq 70$ mg/dL, $\geq 80$ mg/dL, $\geq 90$ mg/dL, $\geq 100$ mg/dL, $\geq 110$ mg/dL, $\geq 120$ mg/dL, $\geq 126$ mg/dL, $\geq 150$ mg/dL, $\geq 200$ mg/dL or $\geq 300$ mg/dL. Upper limits of concentrations of (a) sugar(s) like glucose and/or galactose in the patient's blood, even under a high-sugar condition, may be $\leq 126$ mg/dL, $\leq 140$ mg/dL or $\leq 200$ mg/dL. In principle, any possible range of increased concentrations of (a) sugar(s) like glucose and/or galactose as defined by any possible combination of any of the above lower limits and any of the above upper limits is envisaged. Particular ranges are from about 70 to about 400 mg/dL, from about 70 to about 200 mg/dL, from about 120 to about 200 mg/dL, from about 120 to about 400 mg/dL, from about 140 to about 200 mg/dL, from about 126 to about 200 mg/dL or from about 100 to about 126 mg/dL.

The above-mentioned increased concentrations in the patient's epithelial cells and/or lumen of its gastrointestinal tract or blood may occur during or after an energy-rich meal/food intake or during an energy-rich diet.

For example, a low-sugar condition/situation is present if the concentration of (a) sugar(s) like glucose and/or galactose in the lumen of the at least one part of the patient's gastrointestinal tract (for example in the jejunum) is below or about 1 mM. Such a condition/situation may commonly occur during fasting periods or periods of uninebration. The skilled person is readily able to determine/estimate concentrations of (a) sugar(s) like glucose and/or galactose in the lumen of the at least one part of the patient's gastrointestinal tract, for example during different times of the day and/or in relation to, for example, during or after, a(n) (energy-rich) meal/food intake or in relation to, for example, during a(n) (energy-rich) diet. Respective guidance is provided herein and is known in the art (see, for example, Ferraris Am. J. Physiol. 259 (Gastrointest. Liver Physiol. 22), 1990, G822-G837).

Another example of a low-sugar condition/situation is a concentration of (a) sugar(s) like glucose and/or galactose in the patient's blood at or below 70 to 120 mg/dL. Guidance for differentiating between low- and high-sugar conditions/situations on the basis of the sugar concentrations in the patient's blood is provided herein and is known in the art (see, for example, Kumar ("Clinical Medicine", $3^{rd}$ edition (1994), Bailliére Tindall).

In one aspect of the present invention, the pharmaceutical composition of the invention is (to be), or is prepared to be administered in combination with an energy-rich diet/food/food intake/meal. In accordance with the invention, an energy-rich diet/food/food intake/meal causes a high-sugar condition/situation. The pharmaceutical composition may be administered prior to, during or simultaneously with or after (the intake of) the energy-rich diet/food/food intake/meal, in particular prior to (or simultaneously with) the respective patient may have, may be going to have or may be expected to have an increased concentration of sugar in the lumen and/or in the epithelial cells of at least one part of its gastrointestinal tract (or otherwise being, going to be or being expected to be in a high-sugar condition/situation).

In principle, it is envisaged that the pharmaceutical composition of the present invention is (to be) administered to the patient so that (the peak of) the respective pharmaceutical effect/efficacy coincides with (the peak of) a high-sugar condition/situation, for example with the (peak of) an increased concentration of sugar in the lumen and/or in the epithelial cells of at least one part of the patient's gastrointestinal tract as, for example, resulting from (the intake of) an energy-rich diet/food/food intake/meal. The attending physician is readily able to coordinate and set the administration regimen so that this is fulfilled. In particular, the attending physician is readily able to coordinate/set the dosage regimen, time of administration, kind of pharmaceutical carrier (e.g. time and/or site of release), etc. so that this is fulfilled. For example (in order to fulfil this), the attending physician may administer the pharmaceutical composition of the present invention 3 h prior, 2 h prior, 1 h prior, 30 min prior, directly prior, during, or even (shortly) after (the beginning of)(the intake of) the energy-rich diet/food/food intake/meal. In particular, if the pharmaceutical composition is targeted quickly to and/or released quickly at the desired site of the respective effect/efficacy, it may be administered close to or even (shortly) after (the intake of) an energy-rich diet/food/food intake/meal. The preferred site of effect/efficacy of the active compounds and pharmaceutical composition of the invention is the at least one part of the patient's gastrointestinal tract as described herein and, more particular, the epithelial cells thereof as described herein.

Depending on the character (digestibility) of the energy-rich diet/food/food intake/meal (for example eupeptic or dispeptic), (the peak of) the high-sugar condition/situation is expected to occur at least about 10 min, 15 min, 20 min, 30 min, 40 min, 1 h, 1.5 h, 2 h or 2.5 h after (the beginning of) (the intake of) the energy-rich diet/food/food intake/meal. For example, (the peak of) the high-sugar condition/situation is expected to occur at least about 10 min, 15 min, 20 min, 30 min or 40 min after (the beginning of) (the intake of) an (highly) eupeptic diet/food/food intake/meal (comprising, for example, huge portions of mono- and/or and disaccharides). For example, (the peak of) the high-sugar condition/situation is expected to occur at least about 40 min, 1 h, 1.5 h, 2 h or 2.5 h after (the beginning of) (the intake of) a weakly eupeptic or dispeptic diet/food/food intake/meal (comprising, for example, huge portions of complex polysaccharides and/or fats/oils).

In principle, energy-rich in accordance with the invention means non-energy-low. Hence, in principle, an energy-rich diet/food/food intake/meal in accordance with the invention also encompasses normal diet/food/food intake/meal. Commonly, a normal diet/food/food intake/meal is known to have a normal sugar, carbohydrate, protein, fibre etc. content but is capable to cause a (moderate) high-sugar condition/situation in accordance with the invention. In a particular aspect, however, energy-rich means an increased and/or easier available energy content as compared to a normal energy content.

The energy-rich diet/food/food intake/meal may be a sugar-rich, carbohydrate-rich and/or fat-rich diet/food/food intake/meal and/or a diet/food/food intake/meal having a normal or high glycemic index. The sugar content in the sugar-rich diet/food/food intake/meal may be ≥1% by weight, ≥10% by weight or, preferably, ≥5% by weight. The carbohydrate content in the carbohydrate-rich diet/food/food intake/meal may be ≥10% by energy, ≥70% by energy or, preferably, ≥55% by energy. The glycemic index of the energy-rich diet/food/food intake/meal may be ≥70 or, preferably, ≥90.

Preferably, the pharmaceutical composition of the invention is (to be) administered to a human patient/a human. However, the herein described diseases or disorders (e.g. glucose uptake and/or SGLT-associated conditions, in particular corresponding pathological or non-pathological conditions) may also be treated or prevented in a non-human animal subject/patient like, for example, a pet (e.g. dog, cat, rabbit, rat and mouse), a cattle (e.g. cow, pig, sheep), a horse or pony or a bird (e.g. chicken, turkey, parrot).

The active compounds of the pharmaceutical composition of the invention may be administered with a pharmaceutically acceptable excipient/carrier. Hence, the formulation of the pharmaceutical composition of the invention may comprise the active compounds as defined herein (or a pharmaceutically acceptable salt thereof) and (a) pharmaceutically acceptable carrier(s)/excipient(s). In general pharmaceutically acceptable carriers/excipients comprise carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate; binders, adjuvants, solubilizers, thickening agents, stabilizers, disintergrants, glidants, lubricating agents, buffering agents, emulsifiers, wetting agents, suspending agents, sweetening agents, colourants, flavours, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-β-cyclodextrin, polyvinylpyrrolidone, low melting waxes, ion exchange resins. Other suitable pharmaceutically acceptable carriers/excipients are described in Remington's Pharmaceutical Sciences, $15^{th}$ Ed., Mack Publishing Co., New Jersey (1991).

For example, the active compounds described herein ((poly-)peptides, nucleic acid molecules, vectors) may be comprised in dragées, tablets or pills and the like, in particular in case they are (to be) administered in form of a pharmaceutical composition (but also in form of a dietary product/composition/supplement or food supplement). In a preferred embodiment, said peptides are comprised in coated, e.g. film-coated, dragées, tablets or pills. Such a coating is particularly preferred to enable time- and/or location-controlled release of the active compounds. Corresponding coatings are known in the art and are, inter alia, described in EP-A1 0 109 320, WO 94/06416, EP-A1 0 630 646 or EP-A1 0 548 448.

In principle, it is envisaged that the pharmaceutically acceptable excipient/carrier (and/or the coating) allows for the release of the active compounds (e.g. the (poly)peptides as defined herein) at the desired site of effect/efficacy. In particular, the pharmaceutically acceptable excipient/carrier to be employed in accordance with the invention is envisaged to be capable to target and/or release the pharmaceutical composition ((poly)peptide, nucleic acid molecule or vector) into the at least on part of the patient's gastrointestinal tract as described herein and/or into the epithelial cells thereof. In this context, a preferred part of the gastrointestinal tract is the small intestine, or, more particular, the jejunum and the respective enterocytes.

Preferred carriers, excipients or coatings in this respect are those which confer a resistance to gastric juices and, accordingly, are capable to release active compounds in the gut/intestine, preferably in the small intestine and/or the colon, more preferably in the jejunum. Accordingly, gastric juice resistant carriers, excipients or coatings are preferred. Such carriers, excipients and coatings are known in the art and comprise cellulose derivatives, like carboxymethylene ethylcellulose (Aquateric®), cellulose acetatephthalate (HP50®) or hydroxypropylene cellulose methylphthalate (HP55®); polymeric compounds derived from methacrylic acid and methacrylic acid esters, like Eutragit® L and Eutragit® S (for retard forms Eutragit® RL und Eutragit® RS). Also polyvinyl derivatives may be used. These comprise, inter alia, polyvinylpyrrolidone (e.g. Kolldon®) polyvidone acetate or polyvinyl acetate phthalate (e.g. Opadry®).

The active compounds of the present invention (or salts thereof) or medicaments comprising them may be administered intracellularly by using corresponding techniques known in the art. For example, the active compounds may be encapsulated into liposomes, transferosomes and miosomes and then administered as described above. Liposomes are spherical lipid bilayers with aqueous interiors. Usually, molecules present in an aqueous solution at the time of liposome formation are incorporated into the aqueous interior. The liposomal contents are, on the one hand protected from the external microenvironment and, on the other hand, because liposomes fuse with cell membranes, can be efficiently incorporated into a cell after having been delivered near the cell surface.

Delivery systems involving transfersomes, niosomes and liposomes in pharmaceutical uses are well established, and the person skilled in the art is readily in a position to prepare corresponding transferosomes, niosomes and liposomes comprising the herein defined active compounds, i.e. the herein defined (poly)peptides, nucleic acid molecules encoding the same or vectors comprising said nucleic acid molecules. Corresponding methods are, inter alia, provided in Müller/Hildebrand "Pharmazeutische Technologie: Modeme Arznei", WVG. Wiss Verlag, Stuttgart (1998); Gupta (2005), Int. J. Pharm. 293, 73-82; Torchilin (2005), Nat. Rev. Drug Discov. 4, 145-160. In particular, nucleic acid molecules may be administered to patients in need of medical intervention via transferosomes, liposomes or niosomes. Corresponding preparation methods are known in the art, see, inter alia, Mahoto (2005), Adv. Drug Deliv. Rev. 57, 699-712 or Kawakami (2004), Pharmazle. 59, 405-408.

Also microparticles, nanoparticles or nanogels may be used as delivery systems for the active compounds as defined herein. Such carriers have been developed as an important strategy to deliver peptides and more recently nucleotides/nucleotide sequences. Microparticles, nanoparticles and nanogels and other colloidal drug delivery systems usually modify the kinetics, body distribution and drug release of an associated drug. Corresponding technologies are, inter alia, described and referenced in Kayser (2005), Curr. Pharm. Biotechnol. 6(1), 3-5; Moghimi (2005), FASEB J. 19, 311-330; kettel (2012), ACS Nano 6(9), 8087-93 and Albrecht (2010), Advances in Polymer Science 234, 65-93.

Furthermore, in particular when polypeptides or protein stretches are to be administered in accordance with this invention, hydrogels may be employed. Hydrogels may be employed as microgels (hydrogel microparticles) or as nanogels (hydrogel nanoparticles). Corresponding means and methods are provided and summarized in Pappas (2004), Expert Opin. Biol. Ther. 4, 881-887; Singh (2013), Angewandte Chemie International Edition, 52(10), 3000-3; Singh (2013), Angewandte Chemie 125(10), 3074-77; Singh (2013), Macromolecular Bioscience 13(4), 470-82 and Groll (2009) Journal of Polymer Science Part A: Polymer Chemistry 47(20), 5543-49. Hydrogels are useful in the transmucosal (mostly oral) administration/delivery of therapeutic proteins or polypeptides.

In particular, it is envisaged that the pharmaceutical composition of the invention,
(i) is (to be) or is prepared to be delivered by a hydrogel;
(ii) is (to be) or is prepared to be administered with a pharmaceutically acceptable excipient/carrier which is or comprises a hydrogel; and/or
(iii) comprises the herein described (poly)peptide, nucleic acid molecule or vector being coupled to a hydrogel.

The hydrogel to be employed may comprise thiol-functionalized polymers, in particular linear thiol-functionalized polymers. In a more specific aspect, the hydrogel is based on glycidol, in particular, on polyglycidol, more particular, on thiol-functionalized (linear) (poly)glycidol. The herein described (poly)peptide (nucleic acid molecule or vector) may be coupled to the hydrogel by (a) disulfide linkage(s). In one particular aspect, a TAT (transactivator of transcription) peptide is linked via SS-bridges to the hydrogel. This may increase endocytosis and, hence, may further improve the administration regimen of the herein described pharmaceutical composition. Particular examples of a hydrogel to be employed in accordance with the present invention are disclosed in Groll (2009) (loc. cit.).

One advantage of the hydrogel to be employed is its biocompatibility and degradability. Moreover, it has been demonstrated herein in the appended examples that the use of hydrogel nanoparticles as the pharmaceutical acceptable excipient/carrier provides for highly effective means and methods to effectively introduce polypeptides, such as RS1-Reg. into the epithelial cells as described herein, in particular, after oral application. Moreover, it has been demonstrated that, by the use of hydrogel nanoparticles as the respective pharmaceutically acceptable excipient/carrier, an extraordinary high increase in efficacy can be achieved, in particular, when the herein described RS1-Reg variants have been used as the respective active ingredient. For example, it was demonstrated herein and in the appended examples that about 20000 times less mol of a RS1-Reg variant as compared to mol QEP (administered with another type of pharmaceutically acceptable excipient/carrier) was required to achieve the desired effect (inhibition of glucose (and/or galactose) uptake). A particular hydrogel to be used in this context may be hydrogel nanoparticles composed of thiol-functionalized polymers based on star-shaped (poly)ethylene oxide-stat-propylene oxide as described by Groll (2009, Journal of Polymer Science 47, 5543-5549). RS1-Reg was attached to these gels by thiosulfate linkage.

The (poly)peptide or other active compounds to be employed in accordance with this invention may be administered in form of a pharmaceutically acceptable salt. The most common pharmaceutically acceptable salt employed in patients, in particular in human patients, is the hydrochloride form, i.e. a hydrochloride of the (poly)peptide as defined herein. Such salt is also a preferred salt in context of this invention. However, also other salts are known and envisaged. These comprise, but are not limited to, add addition salts, like acetate, adipate, alginate (particularly preferred), ascorbate, aspartate, benzoate, benzenesulfonate, bisulphate, butyrate, citrate, cyclopentanepropionate, digluconate, dodecyl sulphate, ethane sulfonate, fumarate, glucoheptanoate, glycerophosphate, heptanoate, hexanoate, hydrochloride, 2-hydroxyethane sulfonate, lactate, maleate, methane sulfonate, nicotinate, nitrate, oxalate, pamoate, pectinate, persulphate, 3-phenyl sulfonate, 3-phenylpropionate, phosphate, propionate, salicylate, succinate, sulphate, sulfonate, tartrate, undecanoate, or the like.

Preferred are oral administrations (also in form of a dietary product, dietary composition, food, feed, meal or food additives as described herein). However, in particular patients and particular medical uses, other administration routes (e.g. in form of enemas or suppositories) may be indicated.

Particular dosage forms for oral administration include tablets, dragées, capsules, lozenges, pills, wafers, granules, oral liquids such as syrups, suspensions, solutions, emulsions, powder for reconstitution. Examples of non-aqueous carriers/solvents are propylene glycol, polyethylene glycol, vegetable oils such as olive oil, and injectable organic esters such as ethyl oleate. Aqueous carriers/solvents include water, alcoholic/aqueous solutions, emulsions or suspensions, including saline and buffered media.

Pharmaceutical compositions (e.g. for oral use) comprising a peptide, nucleic acid molecule or vector in accordance with the present invention can be obtained by combining/admixing the active compound(s) with a (solid) excipient/carrier, optionally grinding the resulting combination/mixture, and/or processing the combination/mixture of granules, after adding suitable auxiliaries, if desired, to obtain tablets or dragée cores and the like. As mentioned, these may have a gastric juice resistant coating such as derivatives of cellulose, polymer of methacrylic acid and methacrylic acid esters or derivatives of polyvinyl.

Also provided herein is a method for preparing a pharmaceutical composition for preventing or treating a disease or disorder as described herein and detailed herein, comprising the step of adding and, optionally, admixing a (poly)peptide, a nucleic acid molecule or a vector as disclosed in the context of this invention with a pharmaceutically acceptable carrier.

The pharmaceutical compositions of the invention may be produced as known in the art, for example, as described in Remington's Pharmaceutical Sciences, $15^{th}$ Ed., Mack Publishing Co., New Jersey (1991). In particular, the (poly)peptide as comprised in the pharmaceutical composition may be produced synthetically or recombinantly. For example, the (poly)peptide may be produced as described in Example 1.

The amount of active compounds as defined herein (or a pharmaceutically acceptable salt thereof), which actually may be combined with a pharmaceutically acceptable carrier/excipient to formulate a (single) dosage form, will vary upon the host treated and the particular mode of administration (see herein elsewhere).

The (poly)peptide, nucleic acid molecule, vector or pharmaceutical composition described herein is (to be) or is prepared to be administered to a subject at a suitable dose. Corresponding dosage unit formulations may comprise (a) pharmaceutically acceptable excipient(s)/carrier(s). The active compounds described herein, and optionally an additional therapeutic agent, may be formulated in one single dosage form, or may be present in separate dosage forms and may either be administered concomitantly (i.e. at the same time) or sequentially. In general, the pharmaceutical compositions comprising the active compounds as defined herein may be in any form suitable for the intended method of administration.

The dosage regimen of the active compounds/pharmaceutical compositions as defined herein will be determined by the attending physician and clinical factors. As known in the medical arts, dosages for any one patient depend on many factors, including the patient's size, weight, body surface area, age, the particular compound to be administered, sex, time and route of administration, general health, and on other drugs which may be administered concurrently. However, the skilled person/the attending physician is readily in a position to (a) deduce (therapeutically) effective concentration(s), e. g. in vivo or ex vivo. Corresponding samples may be taken from, for example, the small intestine by a duodenal probe and the active compounds may be detected and their corresponding concentrations may be determined in said samples, for example by HPLC.

The determination of the active compound concentrations may be obtained in human patients, healthy (human) individuals as well as in animals, like laboratory animals, non-human transgenic animals (e.g. transgenic mice, rats, pigs, and the like). It is envisaged that the determination of active compound concentrations in the gastrointestinal tract, e. g. in the gut duodenum or in the small intestine, may, for example, be deduced in (healthy) volunteers and corresponding administration schemes for human patients may be established. For example, the gut passage time, the passage of the active compounds in the gastro-intestinal tract, the dosage dependencies (e.g. oral dosage administered versus dosage detected in various regions of the gastro-intestinal tract) may be determined by standard methods known in the art. Further methods comprise, but are not limited to, the detection of labelled peptides in vivo (e.g. by corresponding labelling techniques, like radioactive labelling, fluorescent labelling, etc.) or physiological/biochemical assays. Accordingly, the dosage of active compounds to be administered, for example orally, in order to obtain a desired concentration of the active compounds in a certain part of the gastrointestinal tract, like the gut duodenum, may be deduced. These and other methods to deduce such concentrations are also known in the art.

For the purpose of the present invention, a (therapeutically) effective dosage of the active compounds, in particular the (poly)peptides as defined herein (or a pharmaceutically acceptable salt thereof) may be a dosage which results in a concentration (extracellularly and/or intracellularly) in the range from $1\times10^{-9}$ M to 1 M, preferably $1\times10^{-7}$ M to 0.5 M, more preferably $1\times10^{-5}$ M to 0.1 M, more preferably $1\times10^{-4}$ M to 0.1 M, more preferably $1\times10^{-3}$ M to 0.05 M, more preferably 20-30 mM, more preferably 2-10 mM and more preferably 5-10 mM. However, also concentrations in the range from 2-3 mM are envisaged in the context of the present invention. For example, in the small intestine, the (therapeutically) effective dosage of the peptides as defined herein (or a pharmaceutically acceptable salt thereof) may be a concentration between 5-10 mM, but also the aforementioned other concentrations may occur in the small intestine.

The extracellular concentrations of the active compounds, in particular the (poly)peptides as defined herein (or a pharmaceutically acceptable salt thereof) may even rise up to 0.05, 0.1, 0.5 or 1 M. Especially in the gut (where, e.g. very high concentrations of sugars (for example after consumption of sweets) may occur), said concentrations may reach those high levels. However, without being bond by theory, the transport capacity of the herein described peptide-transporters may be saturated at a concentration of the (poly)peptides (or a pharmaceutically acceptable salt thereof) of about 100 mM. Accordingly, it is particularly envisaged that the extra cellular concentration of said peptides is at up to about 100 mM. However, as documented, clear physiological effects of the herein defined peptides could already be deduced at concentrations of about 0.1 mM or even smaller concentrations in the extracellular medium. Accordingly, corresponding compositions, e.g. the herein described products, compositions, food, feed, food supplements, meal(s), pharmaceutical compositions (e. g. in form of tablets), and the like, may comprise the active compounds/peptides in amounts that an extracellular concentration of the active compounds/peptides in the range of at least 0.05 mM, 0.01 mM, 0.5 mM, 1 mM, 2 mM, 3 mM or 4 mM is reached in vivo (e.g. in humans). The corresponding concentration in the means/carriers/excipients to be administered may be in the range of 0.1 to 4 M.

In one aspect, the active compounds/ingredients as described therein, for example the (poly)peptides, may be administered at a dose of up to 8 g, up to 5 g, up to 3 g, up to 2 g, up to 1 g, up to 0.5 g or up to 0.1 g per day and patient. This corresponds to a dose of, approximately, up to 115-160, 71-100, 43-60, 29-40, 15-20, 7-10 or 1, 5-2 mg/kg bodyweight (bw) per day. Such (relatively high) dosages are preferred, if the active ingredient is (to be), or is prepared to be, administered freely or, for example, in a gastric juice resistant (coated) tablet or pill.

In another aspect, the active compounds/Ingredients as described herein, for example the (poly)peptides, may be administered at a dose of up to 20 mg, up to 15 mg, up to 10 mg, up to 5 mg, up to 3 mg, up to 2 mg, up to 1 mg or up to 0.1 mg per day and patient. This corresponds to a dose of, approximately, up to 0.3-0.4, 0.2-0.3, 0.15-0.2, 0.075-0.1, 0.04-0.06, 0.03-0.04, 0.015-0.01 or 0.0015-0.001 mg/kg bw per day. Such (relatively low) dosages are preferred, if the active ingredient is (to be), or is prepared to be, administered as/together with, for example, a hydrogel as described herein.

Any of the herein described doses, or any other dose found to be suitable by the attending physician, may be administered once per meal and, hence, 1 to 5 times a day, 2 to 4 times a day or 3 times a day. It is preferred that the meal may be an energy-rich meal as described herein.

In general, a typical patient is expected to have a body-weight of about 50-70 kg. Usually, the heavier the patient, the higher is the dose. However, this correlation may not be necessarily linear, for example, if obese patients are treated. In this context, the dosage may not increase to the same extent as the weight of the patients increases. Hence, once one typical patient to be treated according to the invention may be an obese patient having, for example, more than 80, more than 100, more than 120, more than 140, more than 160 and even more than 180 kg bw, the generally applied dosage regimen may have to be adapted. However, this can readily be done by the attending physician. There are also cases where obese patients were even treated with the same dose than patients having a normal body weight.

The invention further relates to a pharmaceutical composition for use in increasing insulin sensitivity (effect of a given insulin concentration to reduce blood glucose) and/or for decreasing serum glucose and/or galactose levels. This pharmaceutical composition of the invention is envisaged to comprise as an active ingredient (a (poly)peptide that is derived from the regulatory protein RS1 and/or that mimics the function/activity of the regulatory protein RS1 and, in particular, its capability to inhibit SGLT1-driven glucose and/or galactose absorption and/or its capability to bind to/modulate ODC (expression/activity). Nucleic acid molecules encoding this active ingredient ((poly)peptides) and vectors comprising these nucleic acid molecules are also envisaged to be used for this purpose. Particular examples of such (poly)peptides are the regulatory protein RS1 fragments, SDSDRIEP, QSP, QPP, QTP or QCP or any of the other regulatory protein RS1 fragments as disclosed in WO 2006/105912 or WO 2006/105913. Further (preferred) examples of such (poly)peptides (and their corresponding nucleic acid molecules and vectors) are the (poly)peptides as described herein. In a specific aspect, a combination of the (poly)peptide (or the corresponding nucleic acid molecules or vectors) as described herein with the above-described other regulatory protein RS1 fragments may be administered, sequentially or simultaneously.

In particular, insulin sensitivity means effect of a given insulin concentration to reduce blood glucose and insulin effect on the reduction of blood glucose, respectively.

An increase in insulin sensitivity may come along with or correspond to a decrease of the concentration of insulin in the blood, for example, by at least 10%, at least 20%, at least 30%, at least 40%, at least 50%, at least 60% or at least 80%. Commonly, the basal concentration of insulin is increased during the onset of diabetes. Later on, during the course of the diabetes, it may be decreased. The insulin concentration in the blood after overnight fasting is about 0.1-0.5 μg insulin per 1 blood in healthy individuals. In prediabetic individuals or in individuals with a beginning diabetes type 2 the insulin concentration in the blood after overnight fasting is 1-2 μg insulin per l blood. These individuals have a decreased insulin sensitivity. Hence, in a particular aspect, an increase in insulin sensitivity may come along with or correspond to a decrease of the concentration of insulin in the blood, for example, by at least 10%, at least 20%, at least 30%, at least 40%, at least 50%, at least 60% or at least 80% of 1-2 μg insulin per 1 blood.

The increased insulin sensitivity may come along with or correspond to a reduction of blood glucose which is obtained by a lower increase of insulin in the blood as compared to patients without this increase in insulin sensitivity (resulting from, for example, an OGTT or an energy-rich diet/food/food intake/meal as described herein). For example, such a decreased/decelerated increase of insulin may be ≤4, ≤3, ≤2 or ≤1 μg/l/h (the lower values are preferred).

For example, an increased insulin sensitivity in the context of the invention is an insulin sensitivity which is higher than the (decreased) insulin sensitivity of a control as, for example, of an untreated patient/a patient to which the pharmaceutical composition according to the invention has not been administered. In particular, an increased/high insulin sensitivity means that less, a low or lowered amount of insulin is present/required in the serum or in the blood in order to restore normal glucose levels, for example, after an OGTT or an energy-rich diet/food/food intake/meal. For example, an increased insulin sensitivity (effect of a given insulin concentration to reduce blood glucose) s an insulin sensitivity which is 1.1, 1.3, 1.5, 1.75, 2, 2.5, 5, 7.5 or 10 times higher than the insulin sensitivity of a control. For example, a decreased/low insulin sensitivity (for example of a control/control patient) may come along with or correspond to an increase of insulin in the serum after application of glucose and/or galactose (resulting from, from example, an OGTT or an energy-rich diet/food/food intake/meal as described herein) of about 2-6, 2-5, 2-4, 3-4, 3-5 or 4-5 µg/l/h.

In particular, the dosage regimen and administration modes defined herein elsewhere also apply to the aspect of increasement of insulin sensitivity, mutatis mutandis. However, as demonstrated herein and in the appended examples, the amount of/dose of the active ingredients to be administered in order to increase insulin sensitivity can be lower as compared to the situation where glucose and/or galactose uptake is to be reduced/Inhibited. For example, the amount/dose can be 1.1, 1.2, 1.3, 1.5, 1.75, 2, 2.5, 5, 7.5, 10 or at least about 20 times lower, for example as compared to the (ranges of) doses as described herein elsewhere for the situation where glucose and/or galactose uptake is to be reduced/inhibited.

For example, if the herein described pharmaceutical composition is (to be), or is prepared to be, administered in order to increase the insulin sensitivity of a patient, it is (to be), or is prepared to be administered at a daily dose of ≤5 g, ≤3 g, ≤2 g, ≤1 g, ≤0.5 g, ≤0.3 g, ≤0.2 g or ≤0.1 g if administered freely or with a pharmaceutically acceptable carrier as defined herein elsewhere, and at a daily dose ≤10 mg, ≤5 mg, ≤3 mg, ≤2 mg, ≤1 mg, ≤0.5 mg or ≤0.3 mg if particularly administered via a hydrogel as defined herein.

In order to obtain the increased insulin sensitivity, it is preferred that the respective pharmaceutical composition is (to be), or is prepared to be, administered over a longer period of time; and not necessarily in combination with an energy-rich diet/food/food intake/meal as described herein. A longer period of time may, for example, be at least 2, 3, 4, 5, 6 or 7 days, at least 1, 2, 3 or 4 weeks, at least 2, 3, 5 or 6 months or at least 1, 2, 3, 4 or 5 years.

In one aspect as to the increase of the insulin sensitivity, the respective pharmaceutical composition is (to be), or is prepared to be, administered in combination with an energy-rich diet/food/food intake/meal as described herein. A non-limiting example of this is the administration in combination with high-fat diet/food/food intake/meal.

In principle, what has been said with respect to the (characteristics of) the pharmaceutical composition for the treatment or prevention of the disease or disorder as described herein elsewhere also applies to the aspect of the increasement of insulin sensitivity, mutatis mutandis.

Any of the pharmaceutical compositions of the invention may be provided together with an instruction manual or instruction leaflet. The instruction manual/leaflet may comprise guidance for the skilled person/attending physician how to treat or prevent a disease or disorder as described herein in accordance with the invention. In particular, the instruction manual/leaflet may comprise guidance as to the herein described mode of administration/administration regimen (for example route of administration, dosage regimen, time of administration, frequency of administration). In particular, if the disease or disorder to be treated is caused by, physiologically linked to or associated with glucose and/or galactose uptake, the instruction manual/leaflet may comprise the instruction that the pharmaceutical composition is to be administered under a sugar-rich situation, i.e. when there is an increased concentration of glucose and/or galactose in the lumen and/or in the epithelial cells of at least one part of the patient's gastrointestinal tract. Such instruction may comprise the instruction that the pharmaceutical composition is to be administered in combination with a(n) (energy-rich) meal like, for example, 3, 4 or 5 times a day (directly) prior, during or (shortly) after a(n) (energy-rich) meal. In particular, if the insulin sensitivity is to be increased, the instruction manual/leaflet may comprise the instruction that the pharmaceutical composition is to be administered, for example, 3 times a day (in the morning, at noon, in the evening). In principle, what has been said herein elsewhere with respect to the mode of administration/administration regimen may be comprised in the instruction manual/leaflet.

The pharmaceutical composition of the invention may further comprise substances/chemicals and/or equipment suitable for the corresponding therapeutic or preventive intervention and which may be useful for a protocol to reduce glucose and/or galactose uptake via the patient's gastrointestinal tract.

The invention also relates to the (poly)peptide, fragment, nucleic acid molecule or vector as described and defined herein.

The invention further relates to a food composition comprising
(a) a food and/or a food supplement which is capable to cause an increased concentration of sugar as described and defined herein, in particular glucose and/or galactose, in the lumen and/or in the epithelial cells of at least one part of the gastrointestinal tract as described herein (and/or in the blood and/or in the urine); and
(b) the (poly)peptide as described and defined herein.

The invention also relates to a corresponding dietary product/composition/supplement, food (like functional food or "life style food"), feed and food supplement additives, all of which are also referred to herein under the umbrella term "comestibles" according to the invention), as well as to corresponding uses and methods for preparing the same. The comestibles of the present invention may also be used as health comestibles, functional comestibles or lifestyle comestibles. In accordance with the invention, al these "comestibles" are capable to cause an increased concentration of sugar as described as defined herein, in particular glucose and/or galactose, in the lumen and/or in the epithelial cells of at least one part of the gastrointestinal tract as described herein (and/or in the blood and/or in the urine). Accordingly, the present invention is not limited to medical or pharmaceutical uses, means and methods. The descriptions and definitions of the corresponding active compounds, i.e. (poly)peptides, nucleic acid molecules, vectors and, in particular, the QEP peptide or derivatives thereof, provided herein elsewhere also apply to the comestibles, mutatis mutandis. Also the comestibles are characterized in that they comprise the active compound(s) described herein, in particular the herein described (poly)peptide comprising QEP or a derivative thereof. These comestibles are particularly useful, since the absorption/uptake of the sugar provided by these comestibles is reduced/Inhibited or downregulated by the comprised active compounds.

The food and/or food supplement as comprised in the food composition of the invention, or any of the other comestibles described herein, may be energy-rich as described herein or may be an energy-rich food/food intake/meal as described herein.

Like the described energy-rich food/food intake/meal, also the comestibles according to this invention may be sugar-rich, carbohydrate-rich and/or may have a high glycemic index. Also envisaged are comestibles being fat-rich.

As documented herein and in the appended examples, the active compounds disclosed in the context of the present invention are particularly useful in the prevention of sugar-in/uptake into cells (for example in/uptake of monosaccharides, like galactose and, in particular, glucose) under a high-sugar condition. Accordingly, the active compounds of the present invention are particularly useful in comestibles where, on the one hand, the presence of (a high amount of) sugar or other carbohydrates is desired (e.g. because of taste) but, on the other hand, the absorption of sugar (glucose and/or galactose) is (desired) to be avoided (for example because of medical indications like the herein described disorders or diseases or because an (increased) uptake of calories is not desired). It is one major advantage of a comestible of the invention that it can be energy-rich (e.g. sugar-rich, carbohydrate-rich and/or having a high glycemic index) but, nevertheless, can be administered even if an absorption of sugar (glucose and/or galactose) is (desired) to be avoided. In general, the meaning of terms like "food", "feed", "food/dietary supplement/additive", "food basics" and "food precursors" are well known in the art (e.g. Belitz, Grosch, Schelberle, Lehrbuch der Lebensmittelchemie, 5. Auflage, Springer). In principle, the described comestibles refer to all eatable and drinkable compounds/compositions, in particular solid as well as liquid aliment.

In principle, all relevant definitions provided herein elsewhere with respect to the pharmaceutical compositions of the invention apply to the comestibles of the invention, mutatis mutandis.

Non limiting examples of comestibles of this invention or comestibles being prepared in accordance with this invention are:

Bakery products such as cake, cookies, biscuits, doughnuts, bead. Meat products such as sausages, meat balls, Hamburgers, meat pies. Cereal products such as cake mixtures, muffin mixtures, granola. Milk products such as yogurts, curd cheese mixtures, junkets, ice creams, cheeses, milkshakes, butter. Cacao-und chocolate products such as chocolate bars, chocolate coatings. Alcoholic beverage such as liqueur, beer, wine. Non-alcoholic beverage such as soft drinks, lemonade, coca cola. Fruit products such as jams, jellies, fruit bears. Confectionery or sweeties such as jelly bears, marzipan, chewing gum, sugar syrup, sugar mass used for stuffing, candies, dessert powders. Potato products such as French fries, chips. Fat und oil containing products such as mayonnaise, oleomargarine.

Also envisaged is the use of the herein defined active compounds (e.g. the (poly)peptide) in fast food such as frozen foods, canned products, fried or dried products.

The present invention provides for comestibles like dietary compositions/products/supplements, "novel food", "functional food" (food with components whose positive effects can be regarded as physiological or even healthy), "life style food" and wellness products (products with beneficial effects) comprising the herein defined active compounds, in particular the (poly)peptides. For example, such dietary compositions/products/supplements, "novel food", "functional food", "life style food" and wellness products are in form of drinks, bars, powders, (fizzy) tablets, dragées, ampulla, shakes, like, e. g. protein shakes, and the like. Also the dietary compositions/products/supplements, "novel food", "functional food", "life style food" and wellness products, may particularly be carbohydrate-rich and/or may have a high glycemic index and, optionally, may be fat-rich. Said products may also have a high content of proteins, e.g. for the purpose of muscle formation.

Further examples of the herein described comestibles are gum, spray, candies, infant formula, ice cream, frozen dessert, sweet salad dressing, milk preparations e.g., cheese, quark, (lactose-free) yogurt, acidified milk, coffee cream or whipped cream and the like.

Further specific comestibles, to which the active ingredient may be added, include juices, refreshing drinks, shakes, like protein shakes, soups, teas, sour milk beverages, dairy products such as fermented milks, ices, butter, cheese, processed milk and skim milk, meat products such as ham, sausage, and hamburger, fish meat, cake products, egg products such as seasoned egg rolls and egg curd, confectioneries such as cookie, jelly, snacks, and chewing gum, breads, noodles, pickles, smoked products, dried fishes and seasonings. The form of comestibles include, for example, powder, sheet-like forms, bottled forms, canned forms, retort forms, capsule forms, tablet forms and fluid forms.

The feed of the present invention may be any feed comprising the active ingredient. The feed includes, for example, pet feed (e.g. for dogs, cats and rats), cattle feed for cows and pigs, chicken feed for chicken and turkeys, and fish cultivation feed (e.g. for porgy and yellowtail).

The comestibles as referred to and provided herein may be produced by a general corresponding method for producing the same including adding/administering the active ingredient/compound to a raw or (pre-)cooked material and/or precursors of the comestibles. In this context, the compartments may be blended/(ad)mixed. The comestibles according to the present invention may be moulded and granulated in the same manner as generally applied to food, drink or feed, etc. The moulding and granulating method includes, for example, granulation methods such as fluid layer granulation, agitation granulation, extrusion granulation, rolling granulation, gas stream granulation, compaction moulding granulation, cracking granulation, spray granulation, and injection granulation, coating methods such as pan coating, fluid layer coating, and dry coating, puff dry, excess steam method, foam mat method, expansion methods such as microwave incubation method, and extrusion methods with extrusion granulation machines and extruders.

Raw food/feed material or food/feed precursors include, for example, cereals, brans, oil-seed meals, animal-derived raw feed materials, other raw feed materials and purified products.

The present invention also relates to comestibles like dietary additives and additives for food, drinks and feed, which, due to the presence of active compounds as defined herein, are capable of specifically modifying glucose and/or galactose transport in accordance with this invention. The additives can be produced by general art known methods for producing additives. Examples of art-known additives to be blended/admixed with the active compounds of the invention are described in Food Additive Handbook (The Japan Food Additives Association; issued on Jan. 6, 1997). Particular examples of additives include sweeteners, colorants, preservatives, thickeners and stabilizers, anti-oxidants, color fixing agents, bleaches, antiseptics, gum base, bitters, enzymes, brightening agents, acidifier, seasonings, emulsifiers, enhancers, agents for manufacture, flavors, and spice extracts. Further, conventional saccharides, starch, inorganic materials, plant powders, excipients, disintegrators, lubricants, binders, surfactants, and plasticizers.

The concentration of the active compound as comprised in the comestibles (or in the pharmaceutical composition), in particular the (poly)peptide as defined herein, may be 0.001 to 100% by weight, 0.01 to 50% by weight, 0.1 to 25% by weight, 1 to 25% by weight, 2 to 10% by weight, 3 to 7% by weight or about 5% or 10% by weight of the respective comestible (or pharmaceutical composition). For example, a drink containing 100 ml with about 5 g of the active ingredient may be employed in accordance with the present invention.

The amount of the comestibles according to the present invention to be ingested is not specifically limited. The amount to be ingested may generally be 0.1 g to 500 g, 0.1 g to 200 g, 0.1 g to 100 g, 0.1 g to 50 g or 0.1 g to 20 g daily, for example based on the total amount of the active ingredient. The comestibles may continuously ingested (at this amount) for a period from a single day up to 5 years, or even more, for example from 2 weeks to one year. Herein, the amount ingested can be adjusted to an appropriate range depending on the need, desire, severity of a symptom of the individual ingesting the comestibles, the age and body weight thereof, and the like.

The carbohydrates/sugars to be increased in the diets/comestibles of the present invention may be glucose, galactose, saccharose, lactose, maltose, glycogen and/or starch.

Carbohydrate-rich, sugar-rich, starch-rich and fat-rich diets/comestibles, as well as diets/comestibles having a high glycemic index, are known in the art. For example, such compositions are described in Björck and Elmståhl (2003) Proceedings of Nutrition Society 62, 201-206 and Kennedy (2001) J. Am. Diet. Assoc. 101(4):411-420.

The glycemic index (GI) is a ranking of carbohydrates based on their immediate effect on blood glucose (blood sugar) levels. It compares foods gram for gram of carbohydrate. Carbohydrates that breakdown quickly during digestion have the highest GIs. The blood glucose response is then fast and high. Carbohydrates that break down slowly, releasing glucose gradually into the blood stream, have low GIs. The GI is a ranking of carbohydrates on a scale from 0 to 100 according to the extent to which they raise blood sugar levels after eating. Foods with a high GI are those which are rapidly digested and absorbed and result in marked fluctuations in blood sugar levels. Low-GI foods, by virtue of their slow digestion and absorption, produce gradual rises in blood sugar and insulin levels, and have proven benefits for health. Low GI diets have been shown to improve both glucose and lipid levels in people with diabetes (type 1 and type 2). They have benefits for weight control because they help control appetite and delay hunger. Low GI diets also reduce insulin levels and insulin resistance. Recent studies from Harvard School of Public Health indicate that the risks of diseases such as type 2 diabetes and coronary heart disease are strongly related to the GI of the overall diet. In 1999, the World Health Organisation (WHO) and Food and Agriculture Organisation (FAO) recommended that people in industrialised countries base their diets on low-GI foods in order to prevent the most common diseases of affluence, such as coronary heart disease, diabetes and obesity.

As mentioned, however, the above-mentioned advantages of low-GI foods can also be achieved with the normal- or high-GI foods of the invention (comprising the herein-described active ingredients).

To determine a food's GI rating, measured portions of the food containing 10-50 grams of carbohydrate are fed to for example 10 healthy people after an overnight fast. Finger-prick blood samples are taken at 15-30 minute intervals over the next two hours. These blood samples are used to construct a blood sugar response curve for the two hour period. The area under the curve (AUC) is calculated to reflect the total rise in blood glucose levels after eating the test food. The GI rating (%) is calculated by dividing the AUC for the test food by the AUC for the reference food (same amount of glucose) and multiplying by 100. The use of a standard food is essential for reducing the confounding influence of differences in the physical characteristics of the subjects. The average of the GI ratings from all ten subjects is published as the GI of that food.

In view of the above, it is clear that the glycemic index can easily be determined by the skilled person for any given comestibles. Also available are lists and tables with the values of glycemic indices, for example in Brand-Miller, "The new glucose revolution" or in Brand-Miller, "The Glucose Revolution Top 100 Low Glycemic Foods", both published in 2003, Marlow and Company, New York, US.

"Carbohydrate-rich", for example, means that more than 55% of the energy within the comestibles is due to carbohydrates. "Fat-rich" means, for example, that more than 35% of the energy within the comestibles is due to fat. "Sugar-rich", for example, means that the comestible contains more than 5% by weight monosaccharides plus disaccharides. With respect to the present invention, a high glycemic index, for example, is a glycemic index of more than 70 or more than 90.

In accordance with the present invention, "sugar", for example, means all nutrition-relevant sugars and sugar derivatives. These sugars and sugar derivatives are well known in the art. As mentioned before, it is exemplarily envisaged that glucose, galactose, saccharose, lactose and/or maltose are to be employed in accordance with the present invention. Fructose and/or mannose may also be employed.

It is also envisaged that microorganisms express the (poly)peptide as described herein and that these microorganism are employed as/in comestibles or as/in pharmaceutical compositions. In addition to the probiotic effect, the probiotic microorganism expressing the peptide described herein is useful for treating or preventing the disorders or diseases mentioned herein or intervening the none-medical conditions as described herein. The amount of said probiotic microorganism is high enough to significantly positively modify the condition to be treated, preferably obesity, diabetes and the like, but low enough to avoid serious side effects (at a reasonable benefit/risk ratio), within the scope of sound medical judgment. An effective amount of said probiotic microorganism will vary with the particular goal to be achieved, the age and physical condition of the patient being treated, the severity of the underlying disease, the duration of treatment, the nature of concurrent therapy the specific microorganism employed, etc. A decided practical advantage is that the probiotic organism may be administered in a convenient manner such as by the oral route. Depending on the route of administration, a probiotic organism comprising the active ingredients may be required to be coated in a material to protect said organisms from the action of enzymes, acids and other natural conditions which may inactivate said organisms. In order to administer probiotic organisms by other than parenteral administration, they should be coated by, or administered with, a material to prevent inactivation. For example, probiotic organisms may be co-administered with enzyme inhibitors or in liposomes.

Enzyme inhibitors include pancreatic trypsin inhibitor and trasylol. Liposomes include water-in-oil-in-water P40 emulsions as well as conventional and specifically designed liposomes which transport lactobacilli or their by-products to the urogenital surface. Dispersions can also be prepared, for example, in glycerol, liquid polyethylene glycols, and mixtures thereof, and in oils. Generally, dispersions are prepared by incorporating the various sterilized probiotic organisms into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient plus any additional desired ingredient from previously sterile-filtered solution thereof. Additional preferred methods of preparation include but are not limited to lyophilization and heat-drying.

When the probiotic organisms are suitably protected as described above, the active compound may be orally administered, for example, with an inert diluent or with an assimilable edible carrier, or it may be enclosed in hard or soft shell gelatin capsule, or it may be compressed into tablets designed to pass through the stomach (i.e., enteric coated), or it may be incorporated directly with the food, drink or a diet or the comestibles described herein. For oral therapeutic administration, the probiotic organisms may be incorporated with excipients and used in the form of ingestible tablets, buccal tablets, troches, capsules, elixirs, suspensions, syrups, wafers, and the like. The probiotic organism is compounded for convenient and effective administration in effective amounts with a suitable pharmaceutically or food acceptable carrier in dosage unit form as described herein.

In accordance with the present invention, it is also envisaged, that other organisms express the peptide as described herein and that these organisms or parts thereof are employed as (or are for the preparation of) comestibles or pharmaceutical compositions. For example, such organisms to express the peptide as described herein are plants, animals, algae or fungi.

Also a nucleic acid molecule encoding the herein described (poly)peptide or a vector comprising said nucleic acid molecule may be employed in accordance with the present invention.

The nucleic acid molecule encoding the herein defined (poly)peptide may be any type of nucleic acid, e.g. DNA, RNA or PNA (peptide nucleic acid). The monomeric units for adenine, guanine, thymine and cytosine are available commercially (Perceptive Biosystems). A peptide nucleic acid (PNA) is a polyamide type of DNA analog. The DNA may, for example, be cDNA. In one embodiment it is a fragment of genomic DNA encoding RS1. The RNA may be mRNA. The nucleic acid molecule may be natural, synthetic or semisynthetic or it may be a derivative, such as peptide nucleic acid (Nielsen (1991), Science 254, 1497-1500) or phosphorothioates. Furthermore, the nucleic acid molecule may be a recombinantly produced (chimeric) nucleic acid molecule comprising any of the aforementioned nucleic acid molecules either alone or in combination.

The nucleic acid molecule may be part of a vector, for example a gene expression vector. A vector may be a plasmid, cosmid, virus, bacteriophage or another art-known vector used, for example, conventionally in genetic engineering, and may comprise further genes such as marker genes which allow for the selection of said vector in a suitable host cell and under suitable conditions or genes encoding tags.

In particular, the nucleic acid molecules encoding the (poly)peptide as defined herein may be inserted into commercially available vectors. Nonlimiting examples of such vectors include plasmid vectors compatible with mammalian cells, such as pUC, pBluescript (Stratagene), pET (Novagen), pREP (Invitrogen), pCRTopo (Invitrogen), pcDNA3 (Invitrogen), pCEP4 (Invitrogen), pMC1 neo (Stratagene), pXT1 (Stratagene), pSG5 (Stratagene), EBO-pSV2neo, pBPV-1, pdBPVMMTneo, pRSVgpt, pRSVneo, pSV2-dhfr, pUCTag, pIZD35, pLXIN and pSIR (Clontech) and pIRES-EGFP (Clontech). Baculovirus vectors such as pBlueBac, BacPacz Baculovirus Expression System (CLONTECH), and MaxBac™ Baculovirus Expression System, insect cells and protocols (Invitrogen) are available commercially and may also be used to produce high yields of biologically active protein. (see also, Miller (1993), Curr. Op. Genet. Dev. 3, 9; O'Reilly, Baculovirus Expression Vectors: A Laboratory Manual, p. 127). In addition, prokaryotic vectors such as pcDNA2; and yeast vectors such as pYes2 are non-limiting examples of other vectors which may be employed in accordance with the present invention. For vector modification techniques, see Sambrook and Russel (2001), loc. cit.

Vectors can contain one or more replication and inheritance systems for cloning or expression, one or more markers for selection in the host, e.g., antibiotic resistance, and one or more expression cassettes.

The coding sequences inserted in the vector can be synthesized by standard methods, isolated from natural sources, or prepared as hybrids. Ligation of the coding sequences to transcriptional regulatory elements (e.g., promoters, enhancers, and/or insulators) and/or to other amino acid encoding sequences can be carried out using established methods. Furthermore, the vectors may, in addition to the nucleic acid sequences encoding the (poly)peptide defined herein, comprise expression control elements, allowing proper expression of the coding regions in suitable hosts. Such control elements are known to the artisan and may include a promoter, translation initiation codon, translation and insertion site or internal ribosomal entry sites (IRES) (Owens (2001), Proc. Natl. Acad. Sci. USA 98, 1471-1476) for introducing an insert into the vector. Preferably, the nucleic acid molecule encoding for the (poly)peptide defined herein is operatively linked to said expression control sequences allowing expression in eukaryotic or prokaryotic cells. Control elements ensuring expression in eukaryotic and prokaryotic cells are well known to those skilled in the art. As mentioned above, they usually comprise regulatory sequences ensuring initiation of transcription and optionally poly-A signals ensuring termination of transcription and stabilization of the transcript Additional regulatory elements may include transcriptional as well as translational enhancers, and/or naturally-associated or heterologous promoter regions. Possible regulatory elements permitting expression in for example mammalian host cells comprise the CMV-HSV thymidine kinase promoter, SV40, RSV-promoter (Rous sarcoma virus), human elongation factor 1α-promoter, CMV enhancer, CaM-kinase promoter or SV40-enhancer. For the expression in prokaryotic cells, a multitude of promoters including, for example, the tao-lac-promoter, the lacUV5 or the trp promoter, has been described. The expression of the herein defined (poly) peptide in prokaryotic cells may be particularly useful in the preparation of pharmaceutical compositions or comestibles defined herein. It is, for example, envisaged that bacterial hosts are employed which are capable of expressing a (poly)peptide as defined herein, it is also envisaged that these bacteria are administered and/or given to humans in form of pharmaceutical compositions or comestibles; e.g. as "probiotic food-additives".

Beside elements which are responsible for the initiation of transcription, regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (In-Vitrogene, as used, inter alia in the appended examples), pSPORT1 (GIBCO BRL) or pGEMHE (Promega), or prokaryotic expression vectors, such as lambda gt11.

An expression vector according to this invention is at least capable of directing the replication, and preferably the expression, of the nucleic acids and protein of this invention. Suitable origins of replication include, for example, the Col E1, the SV40 viral and the M 13 origins of replication. Suitable promoters include, for example, the cytomegalovirus (CMV) promoter, the lacZ promoter, the gal10 promoter and the *Autographa californica* multiple nuclear polyhedrosis virus (AcMNPV) polyhedral promoter. Suitable termination sequences include, for example, the bovine growth hormone, SV40, lacZ and AcMNPV polyhedral polyadenylation signals. Specifically-designed vectors allow the shuttling of DNA between different host cells, such as bacteria-yeast, or bacteria-animal cells, or bacteria-fungal cells, or bacteria or invertebrate cells.

Beside the nucleic acid molecules encoding the (poly) peptide as defined herein, the vector may further comprise nucleic acid sequences encoding secretion signals. Such sequences are known in the art. Furthermore, depending on the expression system used, leader sequences capable of directing the expressed polypeptide to a cellular compartment may be added to the coding sequence of the nucleic acid molecules of the invention and are also known in the art. A leader sequence is assembled in appropriate phase with translation, initiation and termination sequences, and preferably, a leader sequence capable of directing secretion of translated protein, or a part thereof, into, inter alia, the extracellular membrane or the cytosol. Optionally, the heterologous sequence can encode a fusion protein including a C- or N-terminal identification peptide imparting desired characteristics, e.g., stabilization or simplified purification of the expressed recombinant product. Once the vector has been incorporated into the appropriate host, the host is maintained under conditions suitable for high level expression of the nucleotide sequences, and, as desired, the collection and purification of the peptide, antigenic fragments or fusion proteins of the invention may follow. Of course, the vector can also comprise regulatory regions from pathogenic organisms.

In one embodiment, vectors comprising the nucleic acid molecules of the invention may be suitable for gene therapy, i.e. the vector of the present invention may also be a gene transfer and/or gene targeting vector. Gene therapy, which is based on introducing therapeutic genes or nucleic acid constructs into cells by ex-vivo or in-vivo techniques is one of the most important applications of gene transfer. Suitable vectors, vector systems and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Wang, Nature Medicine 2 (1996), 714-716; WO 94/29469; WO 97/00957; Schaper, Current Opinion in Biotechnology 7 (1996), 635-640 or Verma, Nature 389 (1997), 239-242 and references cited therein. Nucleic acid molecules encoding the herein described peptides and the vectors disclosed herein may be particularly designed for gene therapy approaches. Said compounds may also be designed for direct introduction or for introduction via liposomes, or viral vectors (e.g. adenoviral, retroviral) into the cell. Additionally, baculoviral systems or systems based on vaccinia virus or Semliki Forest Virus can be used as eukaryotic expression system for said compounds. Various viral vectors suitable for gene therapy are, for example, adenovirus, herpes virus, vaccinia, or, preferably, an RNA virus such as a retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can also incorporate multiple genes. All of these vectors can transfer or incorporate a gene for a selectable marker so that transduced cells can be identified and generated.

Retroviral vectors can be made target specific by inserting, for example, a polynucleotide encoding a sugar, a glycolipid, or a protein. Those of skill in the art will know of, or can readily ascertain without undue experimentation, specific polynucleotide sequences which can be inserted into the retroviral genome to allow target specific delivery of the retroviral vector containing the inserted polynucleotide sequence.

The invention further relates to a method of screening for and/or identifying a compound suitable to prevent or treat a disease or disorder as described herein above when being administered to a patient under a high-sugar condition (as described herein above) and/or in combination with an energy-rich diet/food/food intake/meal (as described herein above), said method comprising the steps of i) contacting a compound with an SGLT1-expressing cell or introducing a compound into an SGLT1-expressing cell in the presence of an increased (intracellular) concentration of glucose and/or galactose (as described herein) and determining the glucose and/or galactose uptake activity of said cell, wherein a suppressed or reduced glucose and/or galactose uptake as compared to a control is indicative for the suitability of said compound to prevent or treat said disease or disorder; or ii) administering to an animal model a compound in the presence of an increased concentration of glucose and/or galactose (as described herein) in the lumen and/or in the epithelial cells of at least one part of the animal model's gastrointestinal tract and determining the glucose and/or galactose uptake into the epithelial cells of said at least one part of said gastrointestinal tract or (a) symptom(s) and/or (a) clinical sign(s)/the presence of said disease or disorder, wherein a suppressed or reduced glucose and/or galactose uptake as compared to a control or the decrease of the symptom(s) and/or clinical sign(s)/amelioration of said disease or disorder as compared to a control is indicative for the suitability of said compound to prevent or treat said disease or disorder.

In principle, the relevant definitions and descriptions made herein above with respect to the pharmaceutical and food compositions of the invention also apply here and in the other herein disclosed methods and kits, mutatis mutandis. In particular, the definitions and descriptions made herein elsewhere with respect to the disease or disorder to be prevented or treated, the sugar and high-sugar condition, the energy-rich diet/food/food intake/meal, the increased (intracellular) concentration of glucose and/or galactose, SGLT1 and SGLT1-activity/function and lumen and epithelial cells of at least one part of the gastrointestinal tract also apply here and in the other herein disclosed methods and kits, mutatis mutandis.

The SGLT1-expressing cell may be a cell as described herein and in the appended examples. For example, the cell may be an oocyte of *Xenopus laevis*. Means ad methods for producing such a cell are known in the art and are described herein and in the appended examples. The same applies for means and methods for determining the glucose and/or galactose uptake activity of such a cell. The SGLT1 expressing cell may further express ODC. A suitable animal model may be an animal model as described herein and in the appended examples. For example, a suitable animal model may be an RS1−/− mouse as, for example, described by Osswald (2005, loc. cit.) or a wild-type mouse as, for example, described in examples 6 and 11.

The SGLT1-expressing cell may also be comprised in (a sample of) a tissue of an animal, preferably of a mammalian. Particular examples of such a tissue (sample) are parts of the at least one part of the gastrointestinal tract (for example of the small intestine). A preferred tissue is a sample of the small intestine of a human being. Also such tissues (samples) are described herein and in the appended examples.

In the context of section (i), supra, a control may be an SGLT1-expressing cell (or a tissue comprising the same) in the presence of an increased (intracellular) concentration of glucose and/or galactose which has not been contacted with the compound to be screened and/or identified (or into which this compound has not been introduced) or which has been contacted with a compound which is known not to be capable to suppress or reduce glucose and/or galactose uptake in the presence of an increased (intracellular) concentration of glucose and/or galactose (or into which this compound has been introduced). Examples of a compound which is known not to be capable to suppress or reduce glucose and/or galactose uptake in the presence of an increased (intracellular) concentration of glucose and/or galactose are QCP, QSP, QTP and QPP and hRS1-Reg (S83E) or hRS-1-Reg(S45A). Another example is the reciprocal amino acid stretch of QEP, namely PEQ. Another suitable control as described herein and in the appended example may also be employed.

In the context of section (ii), supra, the control may be an animal model as described above to which the compound to be screened and/or identified has not been administered or to which a compound has been administered which is not capable to suppress or reduce glucose and/or galactose uptake or decrease one of the symptoms/clinical signs/ameliorate said disease or disorder. What has been said with respect to such a (control) compound as to section (i), supra, also applies here, mutatis mutandis.

The suppression or reduction of glucose and/or galactose uptake or decrease of the symptom(s)/clinical sign(s)/amelioration of said disease or disorder is indicative for the suitability of said compound to prevent or treat said disease or disorder if it is, as compared to the respective control, at least 5%, 10%, 20%, 50%, 100% or 200% (the higher values are preferred). The symptom(s) and/or clinical sign(s) may be the symptom(s) and/or clinical sign(s) as described herein above. Particular examples are reduced blood glucose/galactose, reduced blood glucose/galactose peaks (in particular under a high-sugar condition), reduced bodyweight, reduced insulin levels (in particular under a high-sugar condition) and/or reduced/slowed down increase of insulin level after an energy-rich meal or after an OGTT.

The invention further provides for a method of screening for and/or identifying a compound suitable to prevent or treat a disease or disorder as described herein and/or capable of inhibiting (SGLT1-mediated) glucose and/or galactose uptake into a cell, said method comprising the steps of
(i) contacting a compound with ornithine decarboxylase (ODC) or an ODC expressing cell; and
(ii) determining the ODC activity and/or expression (of said cell),
wherein a suppressed or reduced ODC activity and/or expression as compared to a control is indicative for the suitability of said compound to prevent or treat said disease or disorder and/or for the capability of said compound to inhibit (SGLT1-mediated glucose and/or galactose uptake).

In this context, a control may be ODC or an ODC-expressing cell which has not been contacted with the compound to be screened or which has been contacted with a compound which is not capable to suppress or reduce ODC activity and/or expression. Such (control) compounds are described herein and in the appended examples and are, for example, the above-described (control) compounds like the reciprocal amino acid stretches (for example PEQ instead of QEP). For example, a suppressed or reduced ODC activity and/or expression occurs, as compared to a control, if the ODC activity and/or expression is suppressed or reduced by at least about 5%, 10%, 20%, 50%, 100% or 200%.

The invention further provides for a method of screening for and/or identifying a compound suitable to prevent or treat a disorder or disease as described herein and/or capable of inhibiting (SGLT1-mediated) glucose and/or galactose uptake into a cell expressing ODC, said method comprising the steps of
(i) contacting a compound with an ODC-expressing cell; and
(ii) determining the glucose and/or galactose uptake into said cell,
wherein a suppressed or reduced glucose and/or galactose uptake as compared to a control is indicative for the suitability of the compound to treat or prevent a disorder or disease as described herein and/or for the capability of said compound to inhibit (SGLT1-mediated) glucose and/or galactose uptake into a cell expressing ODC.

In principle, what has been said above with respect to the control applies here, mutatis mutandis. A particular control, however, may be a cell which does not express ODC. Examples for such a control may be ODC knock-out cells/cell lines, cell/cell lines where the expression of ODC has been suppressed/reduced by si-RNA methods or ODC knock-out animals.

What has been said with respect to the suppressed or reduced glucose and/or galactose uptake herein above also applies here, mutatis mutandis.

In another aspect, the invention provides for a method of screening for and/or identifying a compound capable of increasing the inhibitory effect of an inhibitor of (SGLT1-mediated) glucose and/or galactose uptake into a cell expressing ODC, said method comprising the steps of
(i) contacting a compound and said inhibitor with an ODC expressing cell; and
(ii) determining the glucose and/or galactose uptake into said cell,
wherein a suppressed or reduced glucose and/or galactose uptake as compared to a control is indicative for the capability of said compound to increase the inhibitory effect of said inhibitor of (SGLT1-mediated) glucose and/or galactose uptake into a cell expressing ODC.

In principle, what has been said with respect to the ODC-expressing cells and the control, supra, also applies here, mutatis mutandis. A particular control may be an ODC-expressing cell which has been contacted only with the inhibitor of (SGLT1-mediated) glucose and/or galactose uptake or with a compound which is not capable to increase the inhibitory effect of the same (for example the reciprocal amino acid stretch). A particular compound to be screened in the context of this aspect is a compound which has positively screened in any of the above methods of screening for and/or identifying. What has been said with respect to the suppressed or reduced glucose and/or galactose uptake herein above also applies here, mutatis mutandis.

The ODC-expressing cell as employed in the context of the invention may further express SGLT1. ODC- (and SGLT1-) expressing cells can be prepared and ODC (and SGLT1) activity and expression (of such a cell) can be determined according to means and methods known in the art and as described herein and in the appended examples. For example, an ODC- (and SGLT1-) expressing cell may be an oocyte of *Xenopus laevis* or a HEK293 cell.

Any of the above-described methods of screening for and/or identifying which make use of the activity and/or expression of ODC may further comprise the step of determining whether the respective capability/suitability of the compound is present under a high-glucose condition and, in particular, in the presence of an increased (intracellular) concentration of glucose and/or galactose (as described herein).

It is known in the art that there are patients with an altered ODC activity and it is known that ODC may have mutations which may lead to such altered ODC activity (for example point mutations) (see, for example, Tamori (1995), Cancer Research 55, 3500-3 and Maekawa (1998), Jpn J Clin Oncol 28, 383-7). Such patients may, hence, not necessarily respond to the administration of the herein described (poly) peptides. Hence, it may also be tested in the context of the invention, whether patients which suffer from any of the diseases or disorders as described herein would indeed respond to the administration of the (poly)peptides and for which of these patients it would indeed be advisable treat them with the (poly)peptide.

Accordingly, the invention further provides for a method for predicting the non-response or response to a (poly) peptide (or another active compound) as described herein of a patient to be treated with said (poly)peptide and/or which suffers from a disease as described herein, said method comprising the steps of:
(i) determining in an ODC-expressing sample of said patient whether the expressed ODC binds to said (poly)peptide and/or whether the ODC activity and/or expression is unaltered or inhibited/reduced by (the binding of) said (poly)peptide;
(ii) attributing a non-binding and/or an unaltered ODC activity and/or expression to the non-response of said patient to said (poly)peptide; and
(iii) attributing a binding and/or inhibited/reduced ODC activity and/or expression to the response of said patient to said (poly)peptide.

An ODC-expressing sample may be a tissue sample of at least one part of the patient's gastrointestinal tract (for example a tissue sample from the small intestine). The skilled person is readily able to determine in an ODC-expressing sample whether said (poly)peptide binds to ODC and whether the ODC activity and/or expression is unaltered or inhibited/reduced by (the binding of) said (poly)peptide. For example, (SGLT1-mediated) glucose and/or galactose uptake or transport (into the sample/cell) may be used as a respective indicator. A respective control may be an ODC-expressing sample which has not been contacted with the (poly)peptide or with another (poly)peptide which is not capable to modulate ODC activity and/or expression and/or SGLT1 activity and/or expression (for example the above-described control compounds). Controls are also described herein and in the appended examples.

The invention further provides for a method for stratifying a patient for prevention or treatment with a (poly)peptide (or another active compound) as described herein, said method comprising steps (i) to (iii), supra;
wherein a non-binding and/or an unaltered ODC activity and/or expression indicates that the patient is not suitable for therapy with said (poly)peptide and that the patient is to be treated with an alternative therapy to said (poly)peptide; and
wherein a binding and/or inhibited/reduced ODC activity and/or expression indicates that the patient is to be treated with said (poly)peptide.

The relevant definitions and descriptions made herein elsewhere also apply here. In particular, the relevant descriptions and definitions made with respect to the method for predicting, supra, also applies here, mutatis mutandis.

The invention further provides for a kit for determining whether a patient suffering from a disease or disorder as described herein is a non-responder or responder to a (poly)peptide as described herein comprising means for determining ODC activity and/or expression and at least one (poly)peptide (or another active compound) as described herein. Examples of means for determining ODC activity and/or expression are provided herein and in the appended examples and are known in the art (see, for example, Milovic (2001, Biochem Pharmacol. 61, 199-206). The kit of the invention may be used in any of the above-described methods of screening or stratifying which make use of the activity and/or expression of ODC.

The invention further provides for a method of developing and/or designing a compound/drug suitable to prevent or treat a disease or disorder as described herein, said method comprising the steps of
(i) identifying the site of ODC to which a (poly)peptide as described herein binds; and
(ii) determining to which extent a compound/drug fits and/or binds to said site of ODC,
(iii) attributing a high extend of fitting and/or binding to the suitability of the compound/drug to prevent or treat said disease or disorder.

The above-described method of developing and/or designing may further comprise the step of modulating said compound/drug so as to fit and/or bind to said site of ODC more closely/tightly or to a higher extent.

On the basis of the common general knowledge and the disclosure provided herein, the skilled person is readily able to identify the site of ODC to which a (poly)peptide as described herein binds and, furthermore, perform the step of determining and attributing as the prescribed in section (i) and (ii), supra. Moreover, the skilled person is able to modulate the compound/drug to be developed and/or designed so as to fit/bind to said site of ODC more closely/tightly/to a higher extent. In this context, the skilled person could, for example, rely on the crystal structure of ODC as, for example, disclosed in Almrud (2000, J. Mol. Biol. 259, 7-16).

The present invention is further described by reference to the following non-limiting figures and examples.

The Figures show:

FIG. 1. Amino acid sequence of the regulatory domain of RS1 from human (hRS1-Reg) comprising amino acids 16-98 of hRS1. Previously identified active motifs are boxed. Seine residues within predicted phosphorylation sites are indicated FIGS. 2A-B. Effects of different intracellular concentrations of hRS1-Reg in the presence intracellular AMG concentrations <10 μM on hSGLT1-mediated AMG transport or on hCNT1-mediated uridine transport expressed in oocytes of Xenopus laevis. hSGLT1 (FIG. 2A) or hCNT1 (FIG. 2B) were expressed in oocytes by injection of 2.5 ng of hSGLT1 cRNA or of 0.5 ng hCNT1 cRNA and incubation for 3 days. Then 50 nl of a high potassium buffer (K-Ori buffer, Veyhl, (2003) J Membrane Biol. 196, 71-81) containing different amounts hRS1-Reg were injected. One hour later hSGLT1 expressed uptake of 50 μM [$^{14}$C]AMG (Veyhl (2003) loc.cit.) or hCNT1 expressed uptake of 5 μM [$^3$H]uridine was measured (Errasti-Murugarren loc. cit). The intracellular concentrations of tripeptides were calculated assuming an aqueous volume of 400 nl per oocyte. Mean value±SE of 24-30 oocytes from three independent experiments are presented.

Figure 2:
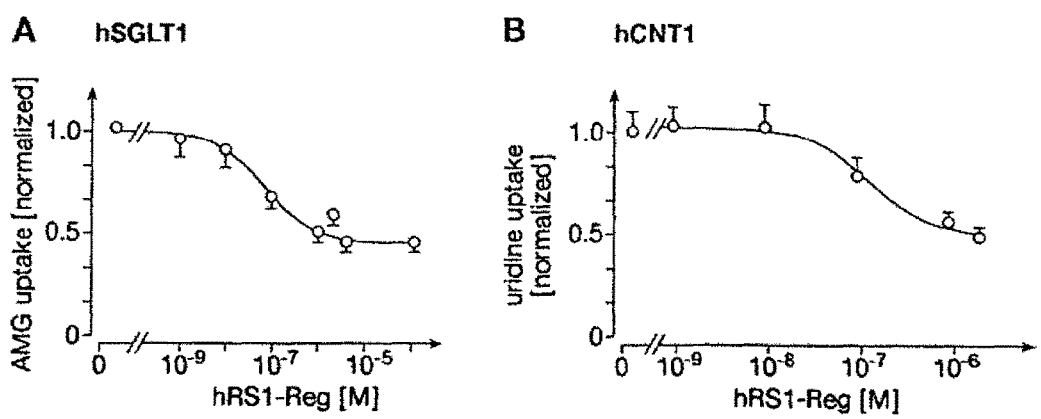
Figure 3:
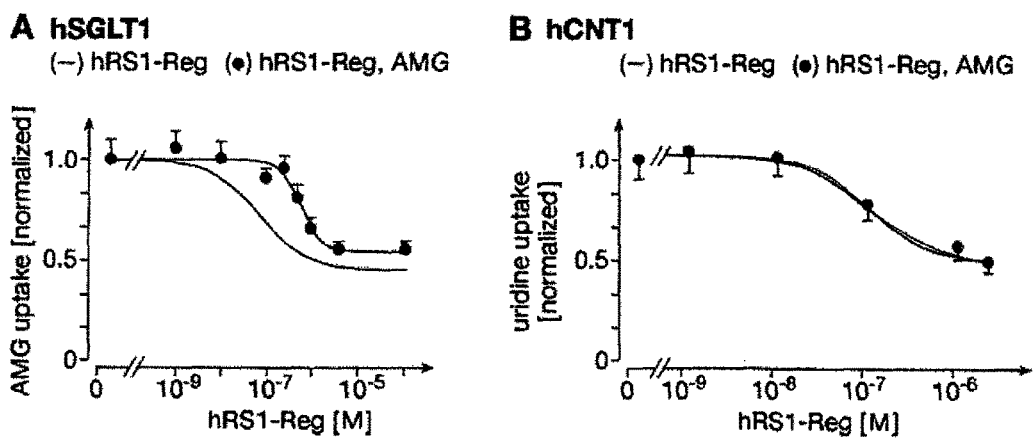

FIGS. 3A-B. Effects of different intracellular concentrations of hRS1-Reg in the presence of 250 μM AMG on hSGLT1-mediated AMG transport or on hCNT1-mediated uridine transport expressed in oocytes. hSGLT1 or hCNT1 were expressed in oocytes as described in FIG. 2. 50 nl of a high potassium buffer (K-Ori buffer, Veyhl (2003) loc.cit.) containing 100 pmol AMG plus different amounts hRS1-Reg were injected. One hour later hSGLT1 expressed uptake of 50 μM [$^{14}$C]AMG or hCNT1 expressed uptake of 5 μM [$^3$H]uridine was measured. Mean value±SE of 24-30 oocytes from three independent experiments are presented. The curves for inhibition of hSGLT1-mediated AMG transport (FIG. 3A) and hCNT1 mediated uridine transport (FIG. 3B) by different concentrations of hRS1-Reg observed without injection of AMG shown FIG. 2 are indicated as lines without symbols.

FIGS. 4A-B. Differential effects of mutations that prevent or mimick phosphorylation in hRS1-Reg on the affinity for down-regulation of hSGLT1 or hCNT1 expressed in oocytes at low intracellular glucose concentration. Oocytes expressing hSGLT1 or hCNT1 were injected with different amounts of the mutants hRS1-Reg(S45A), hRS1-Reg(S45E), hRS1-Reg(S83A) or hRS1-Reg(S83E) without coninjection of AMG as described in FIG. 2. In one of the experiments shown FIG. 4C different concentrations of hRS1-Reg wildtype were injected together with the Cam kinase 2 (CK2) inhibitor KN93. One hour after injection of hRS1-Reg or hRS1-Reg mutants SGLT1-mediated uptake of AMG (FIG. 4A,C) or hCNT1-mediated uptake of uridine (FIG. 4B,D) was measured as described in FIG. 2. Mean value±SE of 24-30 oocytes from three independent experiments are presented. The curves for inhibition of hSGLT1-mediated AMG transport and hCNT1-mediated uridine transport by different concentrations of hRS1-Reg observed without injection of AMG shown FIG. 2 are indicated as broken lines.

Figure 4:
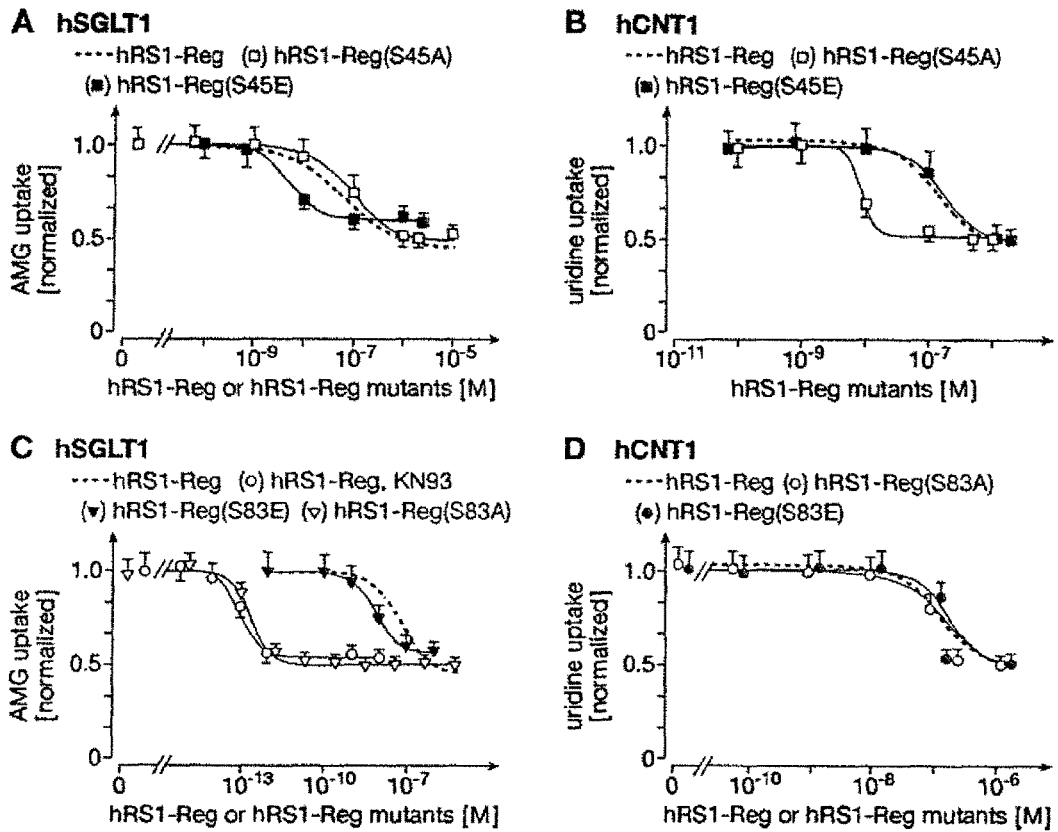
Figure 5:
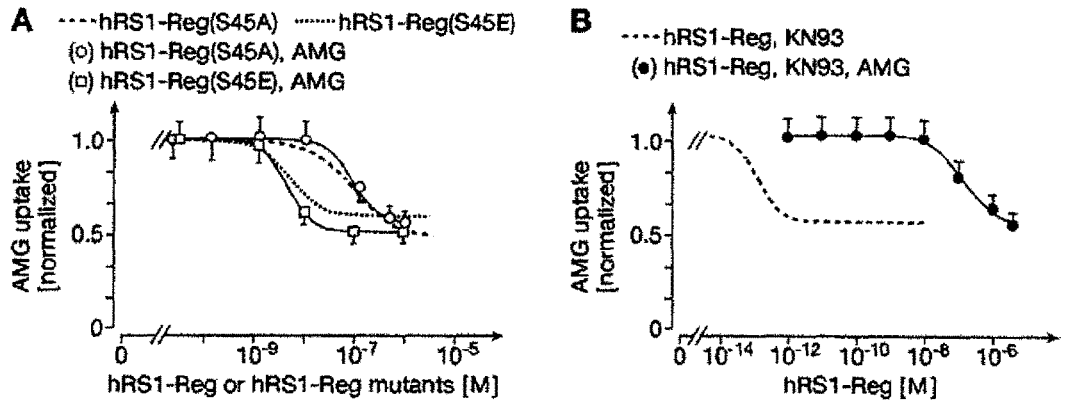

FIGS. 5A-B. Phosphorylation of serine 45 in hRS1-Reg but not phosphorylation of serine 83 is involved in glucose dependent change of affinity of hRS1-Reg for down-regulation of hSGLT1. Oocytes expressing hSGLT1 were injected with 50 nl of high potassium buffer containing different amounts hRS1-Reg(S45A), hRS1-Reg(S45E) or hRS1-Reg wildtype plus the CK2 inhibitor KN93. The mutants were injected without AMG (broken lines) or together with 100 pmol AMG (closed lines and symbols). One h after injection of hRS1-Reg (FIG. 5A) or hRS1-Reg mutants (FIG. 5B) SGLT1 mediated uptake of AMG was measured as described in FIG. 2. Mean value±SE of 24-30 oocytes from three independent experiments are presented. The detailed data from which the broken curves were derived are presented in FIG. 4.

Figure 6:
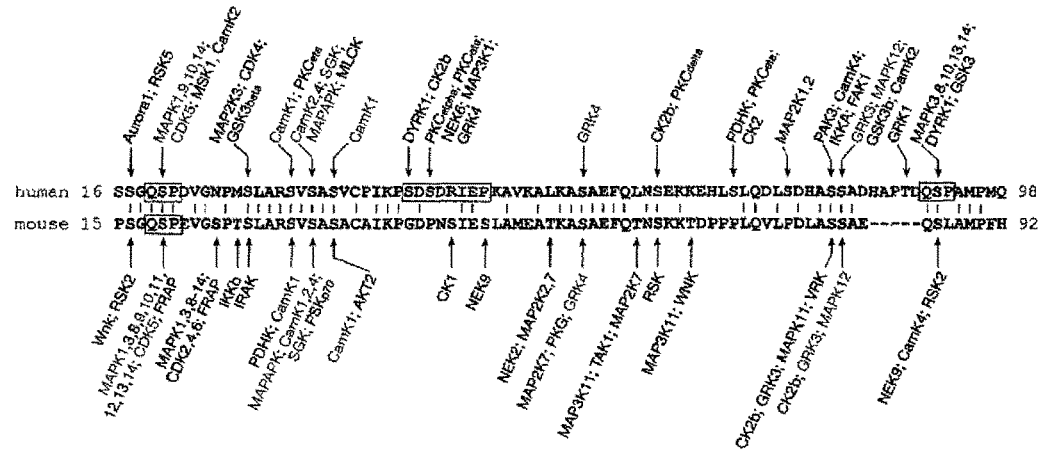

FIG. 6. Amino acid sequence comparison of hRS1-Reg (SEQ ID NO:9) and mRS1-Reg (SEQ ID NO:10). Previously identified active motifs are boxed and serine residues within predicted phosphorylation sites are indicated. Conserved predicted phosphorylation sites are indicated in blue.

FIGS. 7A-B. Phosphorylation of serine 20 in hRS1-Reg increases the affinity of hRS1-Reg for down-regulation of hSGLT1 in the presence of high intracellular glucose dramatically. Oocytes expressing hSGLT1 were injected with 50 nl of high potassium buffer containing different amounts of hRS1-Reg wildtype, hRS1-Reg(S20A) or hRS1-Reg (S20E) without (open symbols, broken lines) or with 100 pmol AMG (closed symbols). After 1 h SGLT1 mediated uptake of AMG was measured as described in FIG. 2. Mean value±SE of 24-30 oocytes from three independent experiments are presented (FIGS. 7A-B). The detailed data for inhibition by hRS1-Reg wildtype are shown in FIG. 2A.

Figure 8:
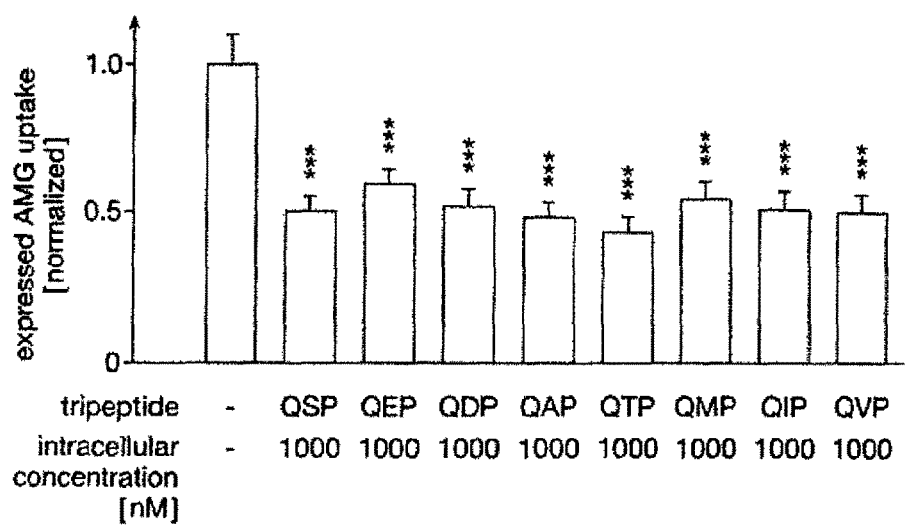
Figure 8:
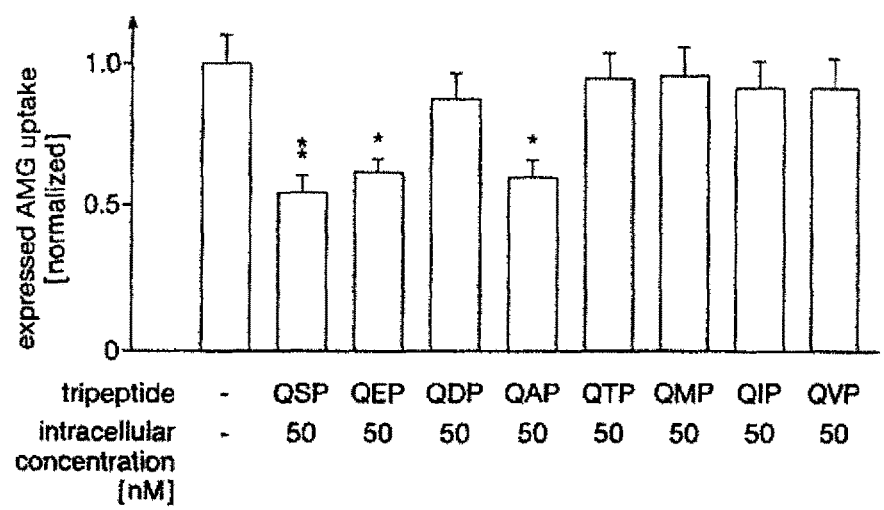

FIG. 8. Effects of two different concentrations (top: 100 nM; bottom: 50 nM) of QXP-type tripeptides on expressed SGLT1 mediated glucose transport in oocytes of Xenopus laevis without injection of AMG. 2.5 ng of hSGLT1 cRNA were injected in X. laevis oocytes, the oocytes were incubated for 3 days. Then 50 nl of a high potassium buffer containing different amounts of tripedides were injected. One hour later SGLT1-expressed uptake of 50 μM [$^{14}$C] AMG was measured. Mean value±SE of 16-18 oocytes from two independent experiments are presented. *P<0.05, **P<0.01 for difference to expression of SGLT1 in the absence of injected tripeptides determined by Anova test with post hoc Tukey comparison is indicated.

Figure 9:
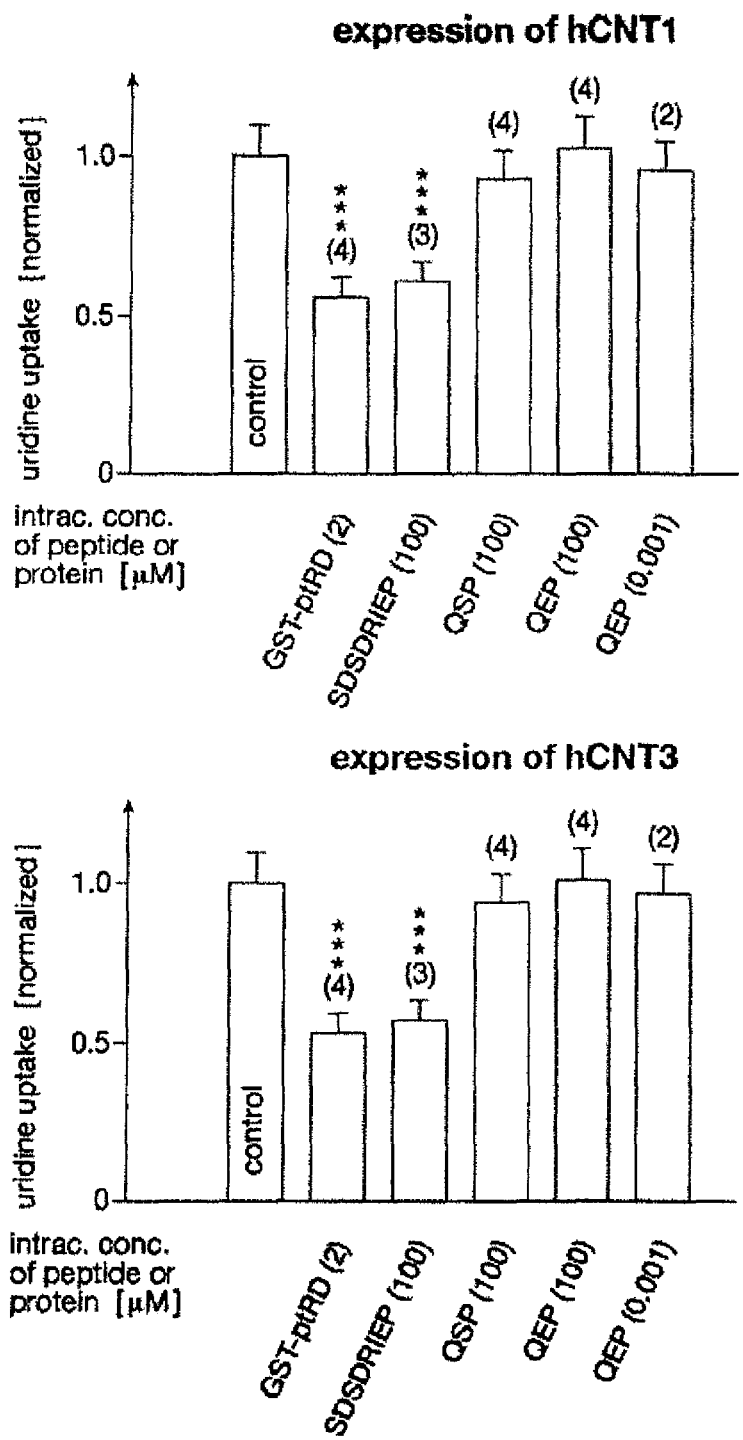

FIG. 9. In contrast to RS1-Reg and SDSDRIEP, QSP and QEP do not downregulate uridine transport expressed by nucleoside transporters hCNT1 (top) and hCNT3 (bottom). Posttranscriptional downregulation of hCNT1 and hCNT3 was measured without injection of AMG. 1.25 ng of hCNT1 cRNA or 10 ng hCNT3 were injected per oocyte, the oocytes were incubated for 3 days, and either 50 nl of K-Ori buffer, 50 nl K-Ori buffer containing either RS1-Reg, SDSDRIEP (SEQ ID NO:35), QSP or QEP were injected. One hour later uptake of 5 μM [$^3$H]uridine was measured. Mean value±SE of 2-4 independent experiments in each of which 8-10 oocytes were analysed are presented. *** P<0.001 indicates the significance to the control determined by ANOVA with post hoc Tukey comparison.

Figure 10:
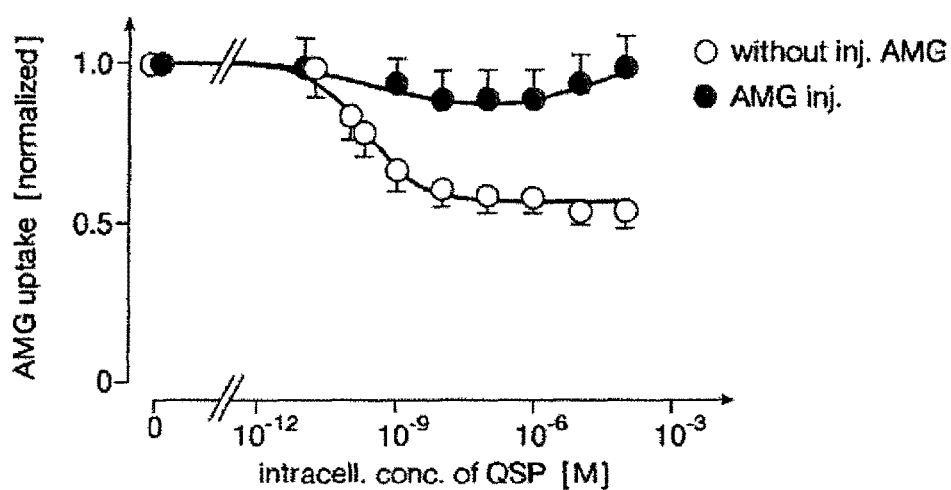

FIG. 10. Intracellular AMG prevents posttranscriptional down-regulation of hSGLT1 by QSP. 2.5 ng of hSGLT1 cRNA were injected into X. laevis oocytes, the oocytes were incubated for 3 days, and 50 nl of K-Ori buffer without of with 2 mM AMG or 50 nl K-Ori buffer containing different amounts of QSP without and with 100 pmol AMG were injected. One hour later uptake of 50 μM [$^{14}$C]AMG was measured. (○) Measurements without injection of AMG (intracellular AMG<10 μM), (●) Measurements with injection of AMG i (intracellular AMG~0.25 mM). Mean values±SE of 24-30 measurements from three independent experiments are indicated.

Figure 11:
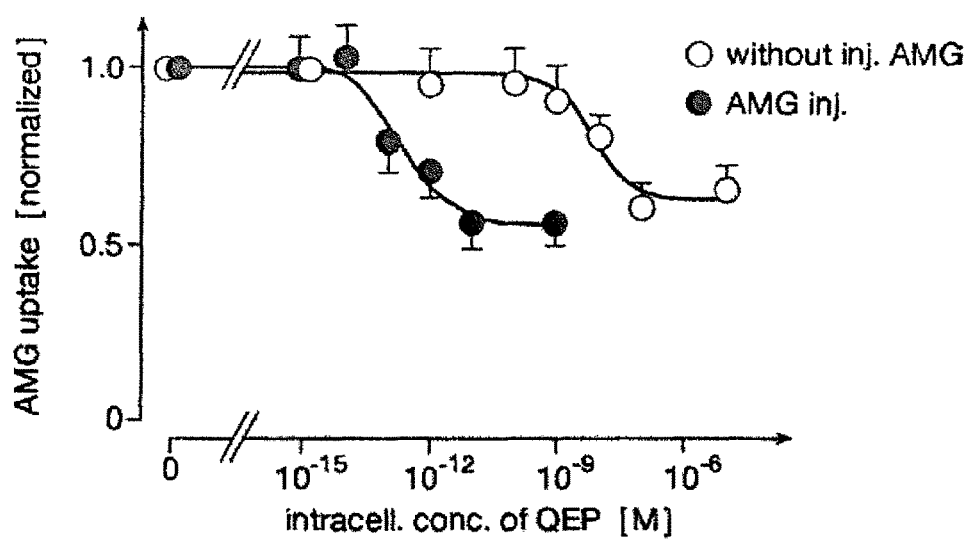

FIG. 11. Intracellular AMG increases the affinity of QEP to downregulate expression of hSGLT1. Effect of QEP on the expression of hSGLT1 mediated transport was measured in the presence of an intracellular AMG concentration<10 μM (○) or of about 250 μM (●). 2.5 ng of hSGLT1 cRNA were injected in *X. laevis* oocytes, the oocytes were incubated for 3 days, and 50 nl of K-Ori buffer without or with AMG or 50 nl K-Ori buffer containing different amounts of QEP without and with AMG were injected. One hour later uptake of 50 μM [$^{14}$C]AMG was measured. Mean value±SE of 24-30 measurements from three independent experiments are indicated.

Figure 12:
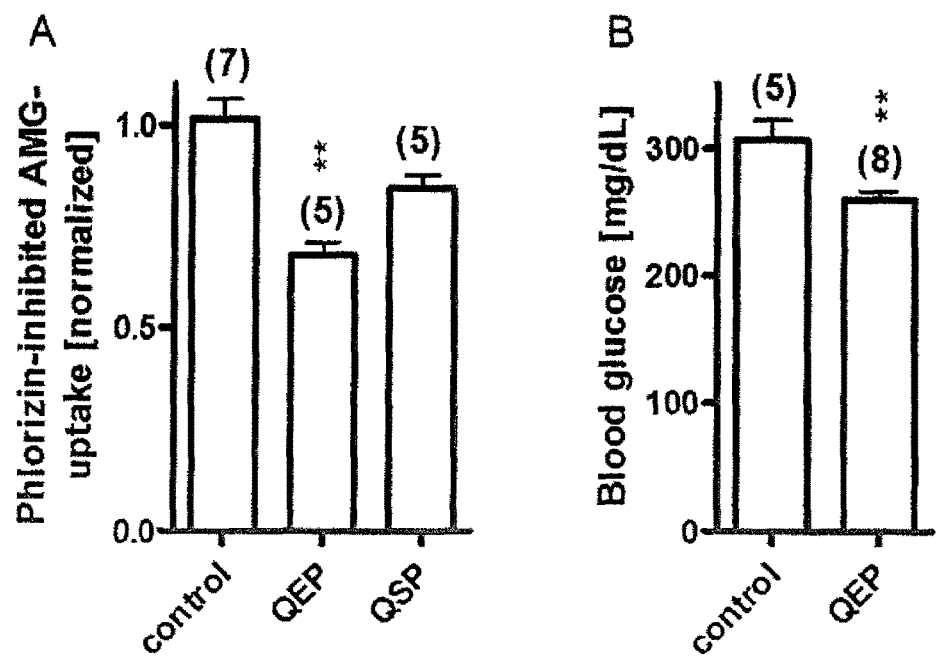

FIG. 12. Down-regulation of mSGLT1 and glucose absorption in small intestine after oral application of QEP in RS1−/− mice. RS1−/− mice on standard diet that had been starved over night were gavaged with 200 μl PBS (controls), 200 μl PBS containing 20 μmol QEP or 20 μmol QSP. A). After 2 h, uptake of 10 μM [$^{14}$C]AMG into everted small intestinal rings was measured in the absence and presence of 200 μM phlorizin and phorizin inhibited AMG uptake was calculated. B) 2 h after gavage with PBS or PBS containing QEP the mice were gavaged with 200 μl water containing 40% glucose and 15 min later the glucose concentration of the systemic blood was determined. Mean values±SE of 5 animals are presented. The uptake measurements in each animal were performed in quadruplicate. ** $P<0.01$ for difference to control calculated by ANOVA with posthoc Tukey comparison (A) or Student t-test (B).

Figure 13:
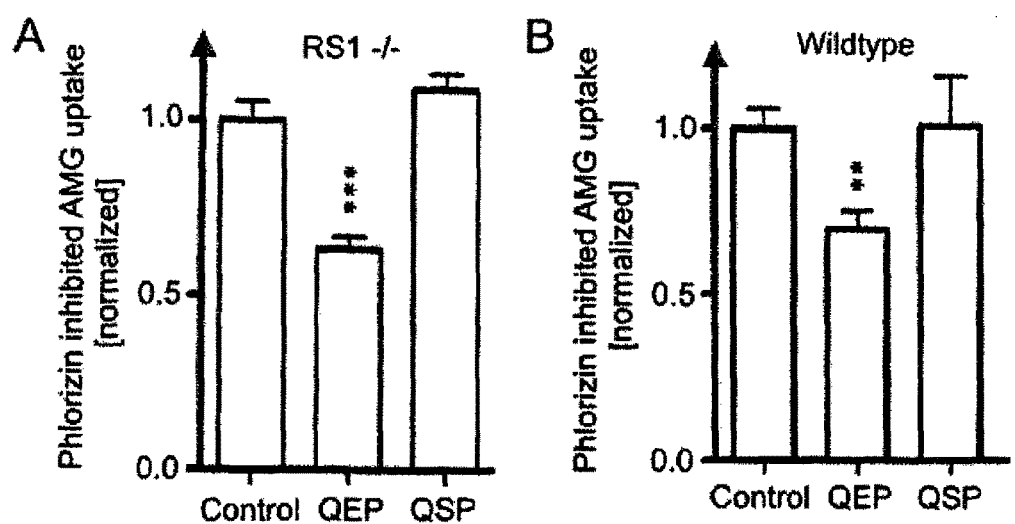

FIG. 13. Down-regulation of mSGLT1-mediated AMG uptake into everted small intestinal segments after incubation with QEP in RS1−/− mice (A) and wildtype mice (B). Segments of inverted jejunum were incubated for 30 min at 37° C. at pH 6.4 with tissue culture medium containing 5 mM D-glucose without addition (control) with 5 mM QEP (QEP) or with 5 mM QSP (QSP). After washing with PBS phlorizin inhibited uptake of 10 μM [$^{14}$C]AMG was measured as in FIG. 12. Mean values±SE of 5 animals are presented. The uptake measurements in each animal were performed in quadruplicate. The significance of the difference compared to control was determine by ANOVA with posthoc Tukey comparison $P<0.01$, *$P<0.001$.

Figure 14:
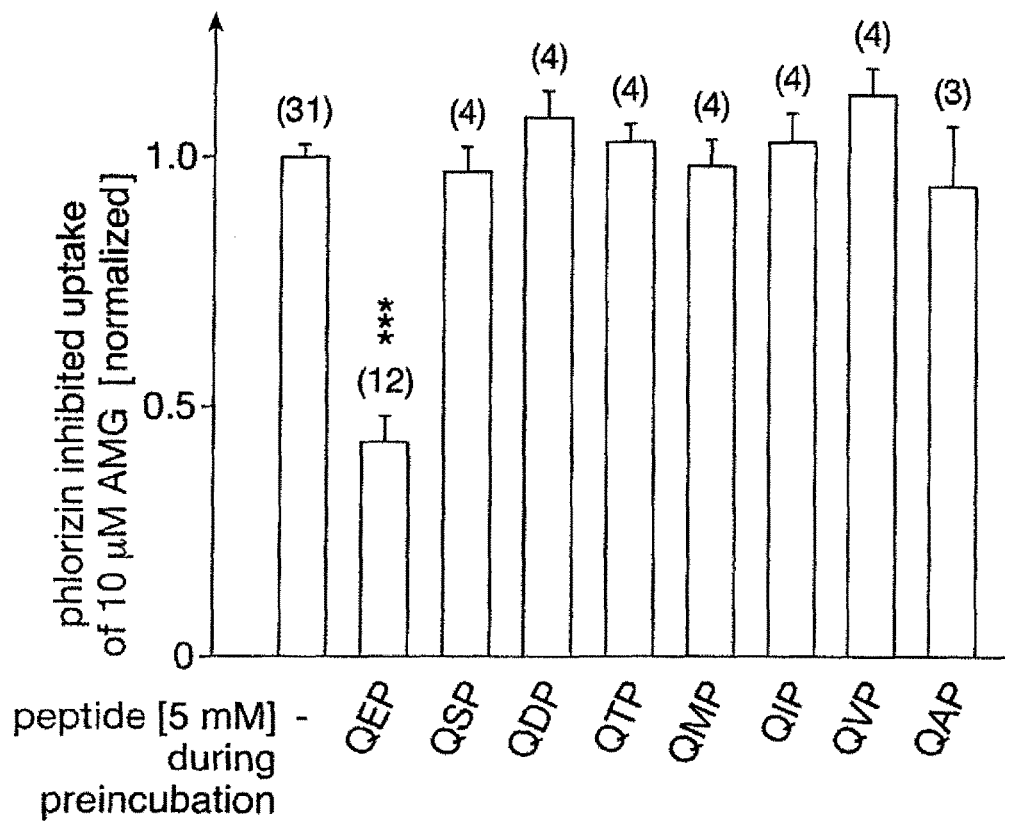

FIG. 14. QEP down-regulates transport activity of hSGLT1 in human small intestine after 30 min incubation with 5 mM of tripeptides in the presence of 5 mM D-glucose in contrast to other QXP-type tripeptides. The measurements were performed with identical areas of jejunal mucosa which were obtained during bariatric surgery of obese patients with body mass indices ~50. The mucosal pieces were incubated for 30 min in culture medium (pH 6.4, containing 5 mM D-glucose) in the absence and presence of 5 mM of the indicated tripeptides. After washing with PBS at pH 7.4 phlorizin inhibited uptake of 10 μM [$^{14}$C]AMG was measured as in FIG. 12. Mean values±SE are indicated. The number of independent experiments measurements are given in parenthesis. In each experiment 16 areas were measured, 8 without QEP (4 without phlorizin and 4 with phlorizin) and 8 with QEP (4 without phlorizin and 4 with phiortzin) ***$P<0.001$ indicates the significance to the uptake measured after incubation without tripeptides determined by ANOVA with post hoc Tukey comparison.

Figure 15:
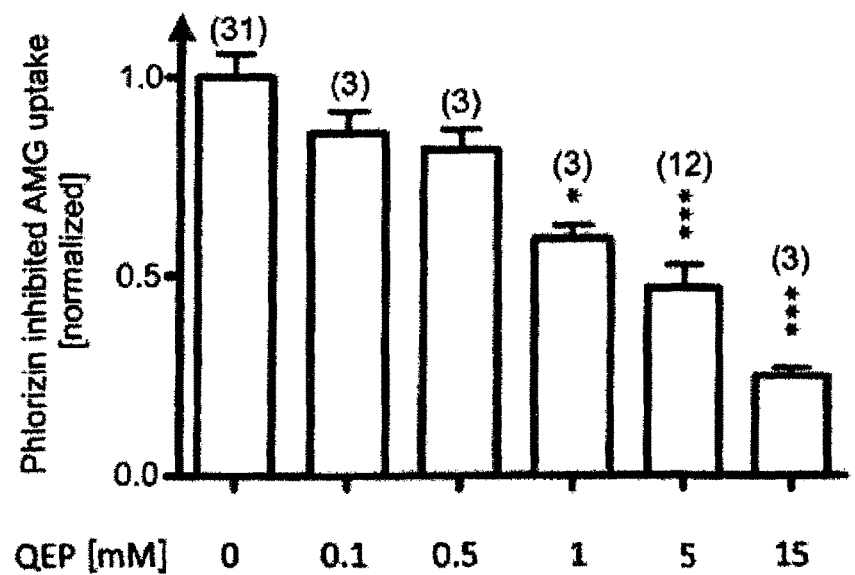
Figure 16:
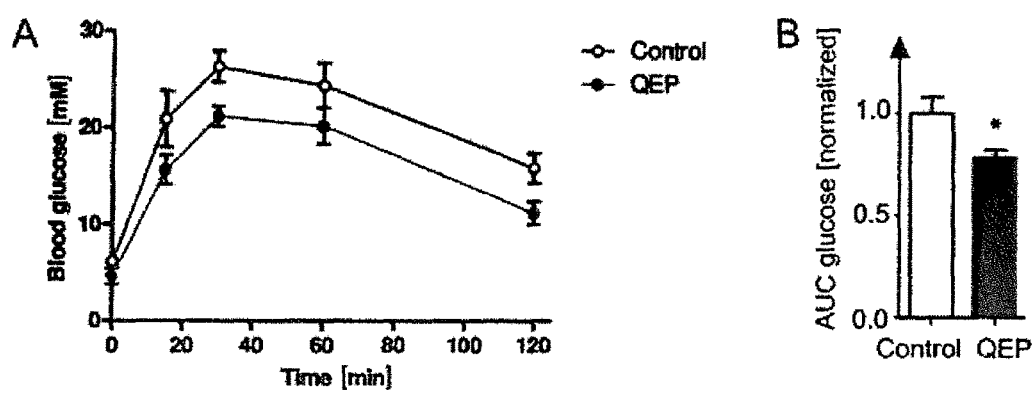

FIG. 15. QEP concentration dependence of QEP induced down-regulation of hSGLT1 in human small intestine after 30 min incubation in the presence of 5 mM D-glucose. Identical areas of human mucosa were incubated for 30 min with different concentrations of QEP in the presence of 5 mM D-glucose as in FIG. 14. After washing with PBS phlorizin inhibited uptake of 10 μM [$^{14}$C]AMG was measured as in FIG. 12. Mean values±SE are indicated. The number of independent experiments measurements are given in parenthesis. The significance to the uptake measured after incubation without QEP was determined by ANOVA with post hoc Tukey comparison. *$P<0.05$, ***$P<0.001$ FIG. 16. Effect of gavage with high dosage of QEP on glucose absorption during oral glucose tolerance test in mice. Starved New Zealand obese (NZO) mice on hypercaloric high fat, high glucose diet were gavaged two times with 200 μl water without (○) or with 100 mM QEP (●). Three h later an oral glucose tolerance test (OGTT) was performed by gavaging the mice with 200 μl water containing 40% D-glucose and measuring the D-glucose and insulin concentrations in the blood after different time intervals. A) Plasma glucose concentrations during the OGTTs. B) Areas under the curves shown in FIG. 16A. Mean values±SE are indicated.

Figure 17:
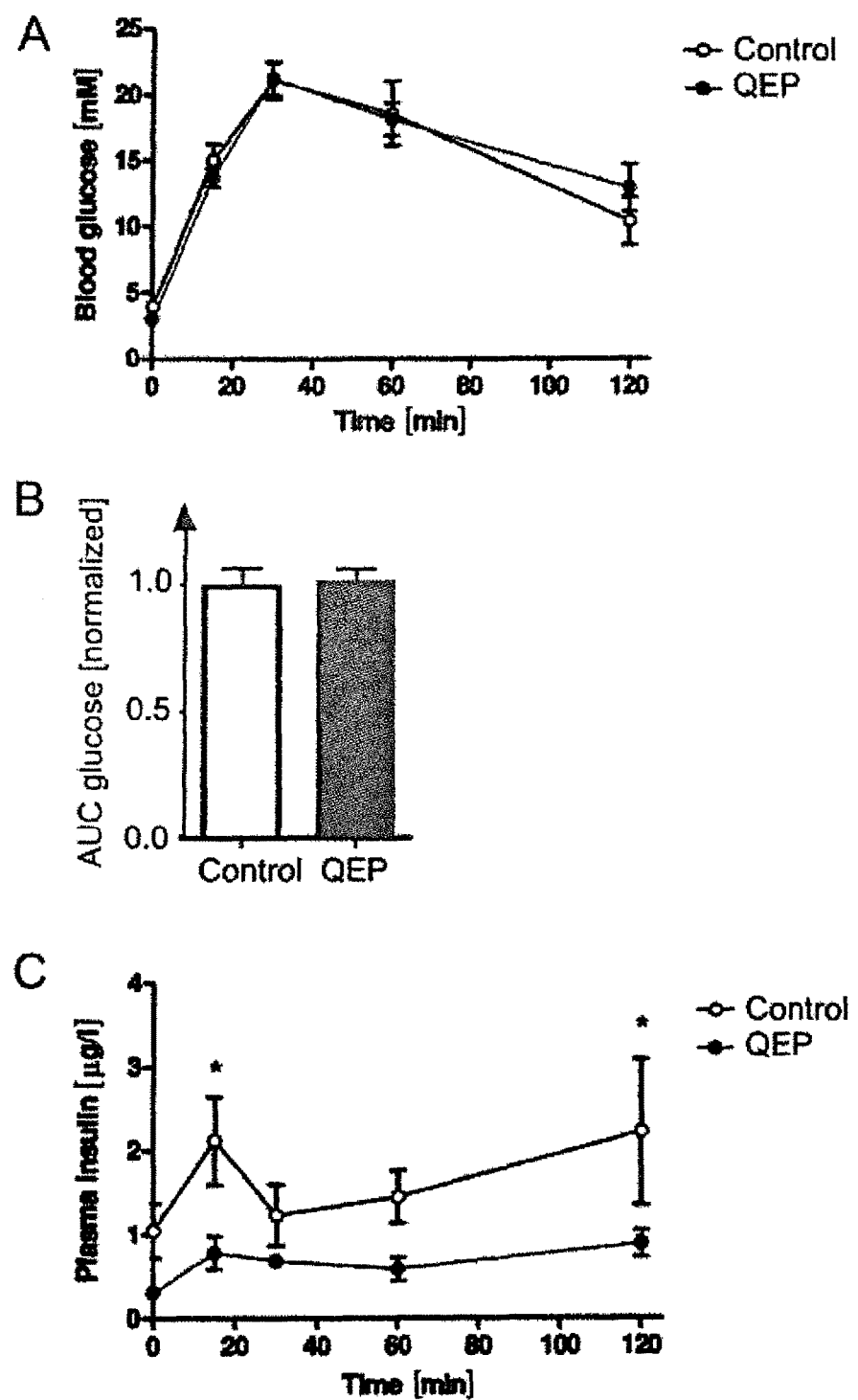

FIG. 17. Effect of 5 mM QEP in the drinking water of NZO mice on glucose and insulin concentration profiles in the blood during oral glucose tolerance test (OGTT). NZO mice on hypercaloric high fat, high glucose diet received drink water without (○) or with 5 mM QEP (●). After starving over night the animals were gavaged with 200 μl water containing 40% D-glucose and the D-glucose and insulin concentrations in the blood after different time intervals were measured. A) Plasma glucose concentrations during the OGTTs. B) Areas under the curves shown in FIG. 17A. C) Plasma insulin concentrations during the OGTTs. Mean values±SE are indicated. *$P<0.05$ for difference between insulin concentrations in the two experimental groups after the respective time intervals test by ANOVA with posthoc Tukey comparison.

Figure 18:
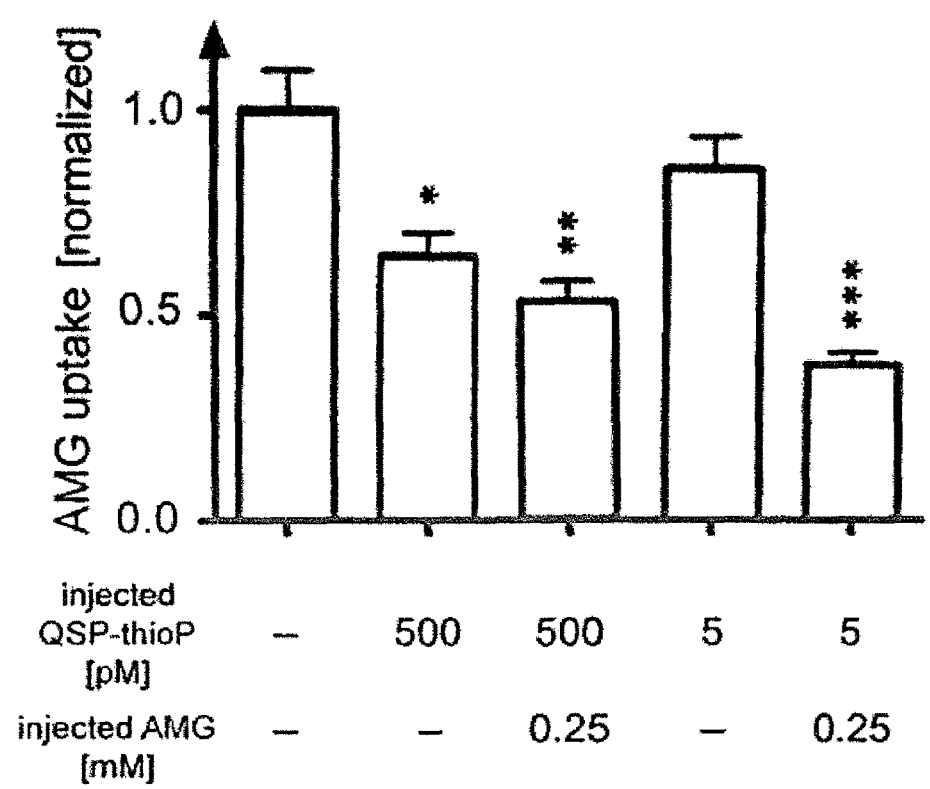

FIG. 18. Effects of different intracellular concentrations of QSP-thiophosphate (QSP-thioP) at low concentration (<10 μM) or 0.25 mM Intracellular AMG on hSGLT1 mediated AMG transport. hSGLT1 was expressed in oocytes as in FIG. 2. Then 50 nl of a high potassium buffer containing different amounts of QSP-thioP were injected. One hour later hSGLT1 expressed uptake of 50 μM [$^{14}$C]AMG was measured as described in FIG. 2. The intracellular concentrations of QSP-thioP and AMG which were calculated as in FIG. 2 are indicated. Mean value±SE of 16-20 oocytes from two independent experiments are presented. Significance of differences from the control without injection of QSP-thioP were calculated as in FIG. 8. *$P<0.05$, $P<0.01$, *$P<0.001$.

Figure 19:
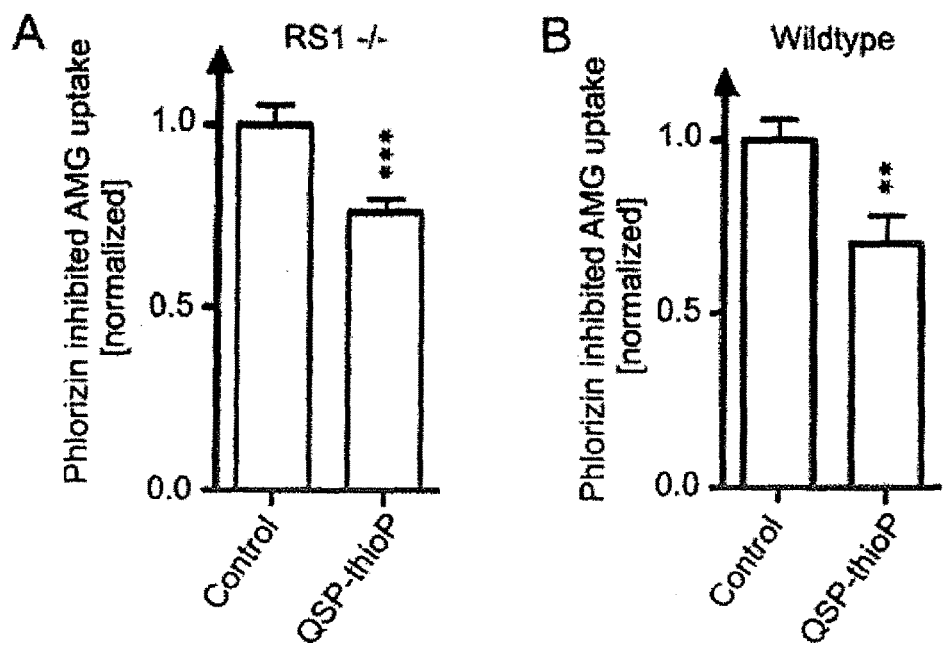

FIG. 19. Down-regulation of mSGLT1 mediated AMG uptake into everted small intestinal segments of RS1−/− (A) and wildtype mice (B) after incubation with QSP-thioP in the presence of 5 mM D-glucose. Segments of inverted jejunum were incubated for 30 min at 37° C. at pH 6.4 with culture medium containing 5 mM D-glucose without addition (control) or with 5 mM QSP-thioP. After washing with PBS phlorizin inhibited uptake of 10 μM [$^{14}$C]AMG was measured as in FIG. 12. Mean values±SE of 5 animals are presented. The uptake measurements in each animal were performed in quadruplicate. The significance of the difference compared to control was determine by Student t-test. $P<0.01$, *$P<0.001$.

Figure 20:
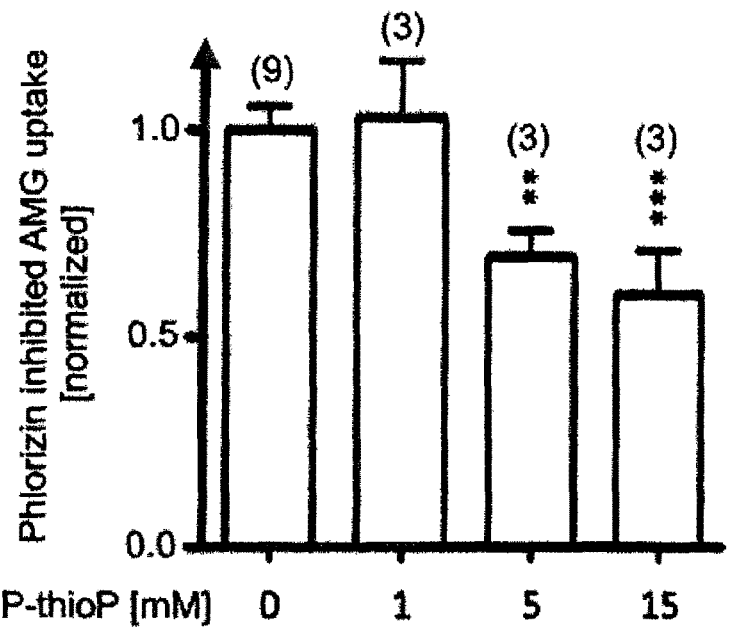

FIG. 20. QSP-thioP down-regulates hSGLT1 mediated AMG uptake in human small intestine in the presence of 5 mM D-glucose. Identical areas of human mucosa were incubated for 30 min with different concentrations of QSP-thioP in the presence of 5 mM D-glucose as in FIG. 14. After washing with PBS phlorizin inhibited uptake of 10 μM [$^{14}$C]AMG was measured as in FIG. 12. Mean values±SE are indicated. The number of independent experiments measurements are given in parenthesis. The significance to the uptake measured after incubation without QEP was determined by ANOVA with post hoc Tukey comparison. P<0.01, *P<0.001

FIGS. 21A-D. Introducing RS1-Reg into enterocytes by coupling to nanoparticles. RS1−/− mice on standard diet that had been starved over night were gavaged with 200 μl unloaded nanoparticles (controls), 200 μl nanoparticles with coupled mRS1-Reg(S19A) (mRS1-Reg(S19A)) or with 200 μl nanoparticles coupled with mRS1-Reg(S19E) (mRS1-Reg(S19E)). After 2 h, uptake of 10 μM AMG traced with [$^{14}$C]AMG (FIGS. 21A, C) or uptake of 1 mM AMG (FIGS. 21B, D) traced with [$^{14}$C]AMG into everted small intestinal rings was measured in the absence and presence of 200 μM phlorizin and phorizin inhibited uptake was calculated. Mean values±SE are presented. The number of animals in each of which quadruplicate measurements without phlorizin and with 200 μM phlorizin were performed, are indicated in brackets. ***P<0.001 for difference to control calculated by Student t-test (B).

Figure 22:
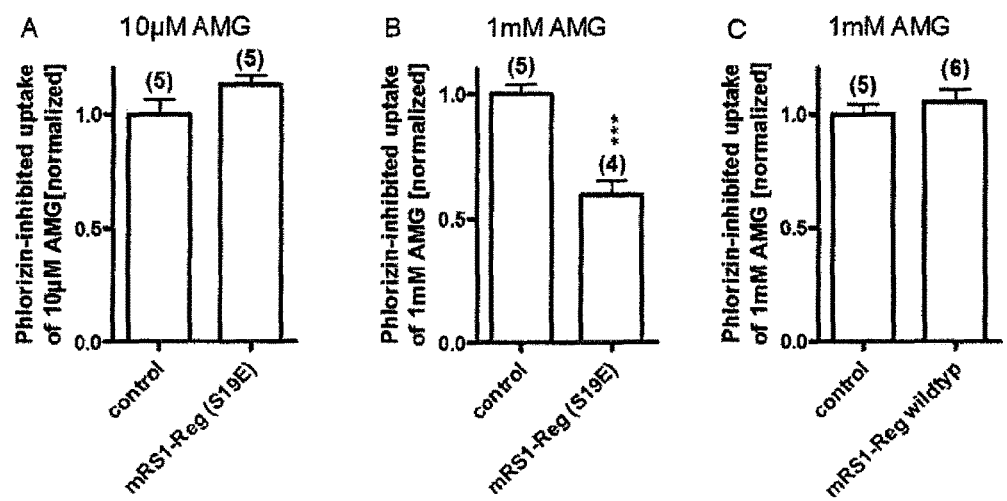

FIG. 22. Downregulation of SGLT1 in mouse small intestine by mRS1-Reg(S19E) coupled to nanoparticles. Wildtype mice on standard diet that had been starved over night were gavaged with 200 μl unloaded nanoparticles (controls), 200 μl of nanoparticles with coupled mRS1-Reg (S19E) (mRS1-Reg(S19E)) or with 200 μl nanoparticles coupled with wildtype mRS1-Reg. After 2 h, uptake of 10 μM AMG traced with [C]AMG (A) or uptake of 1 mM AMG traced with [$^{14}$C]AMG into everted small intestinal rings was measured in the absence and presence of 200 μM phlorizin (B, C). Mean values±SE of phlorizin inhibited AMG uptake are presented. The number of animals in each of which quadruplicate measurements were performed, are indicated in brackets. ***P<0.001 for difference to control calculated by Student t-test.

Figure 23:
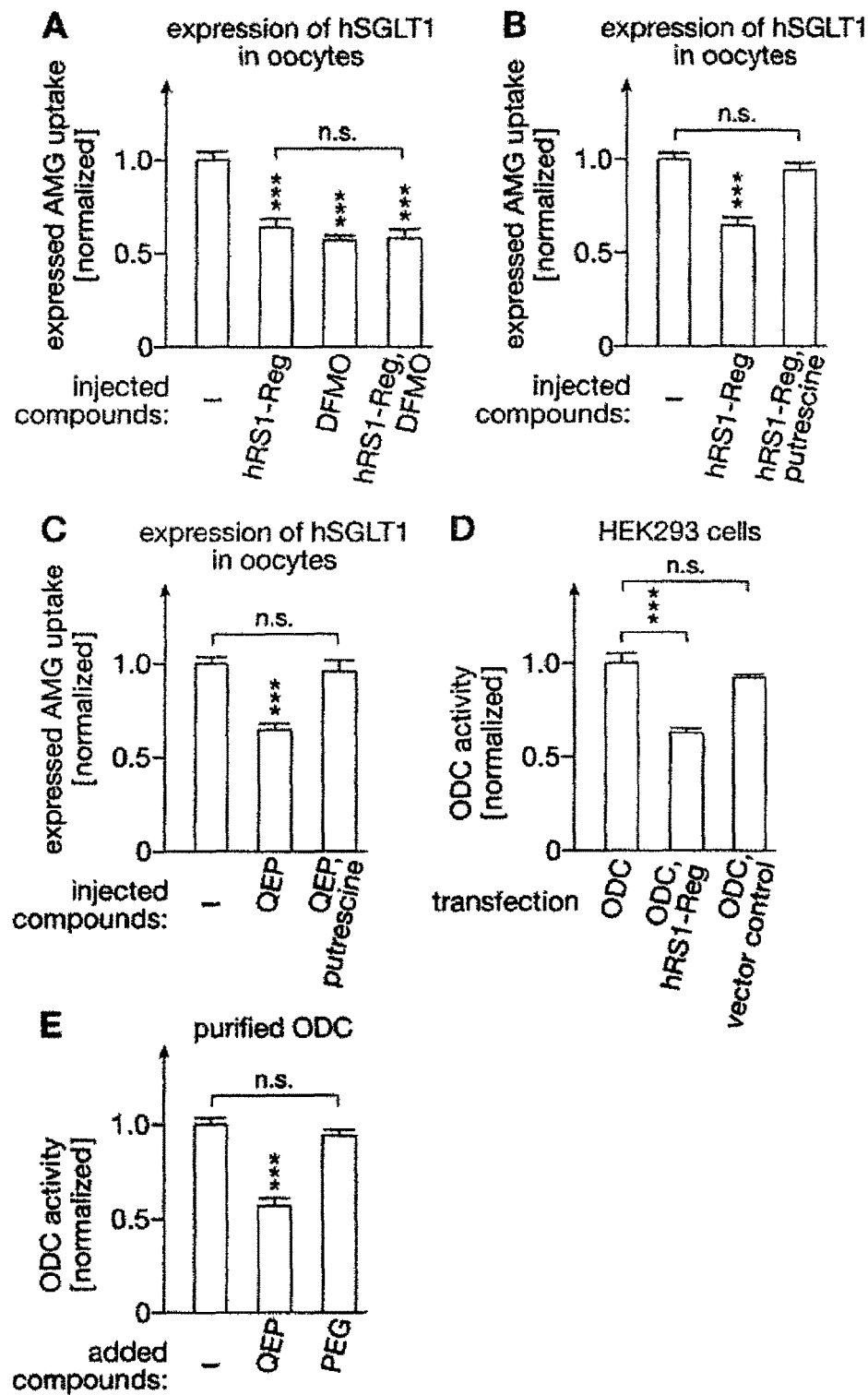

FIG. 23. ODC is the receptor of RS1-Reg and QEP and that putrescine generated by ODC induces down-regulation of SGLT1. In A-C hSGLT1 was expressed in oocytes as in FIG. 2. hRS1-Reg protein or QEP were injected alone or together with DFMO (intracell. concentration 3 mM) (A) or with putrescine (intracellular concentration 1 μM) (B, C). Expressed uptake of 25 μM [$^{14}$C]AMG was measured 1 h later as FIG. 2. In A-C mean value±SE of 24-30 oocytes from three independent experiments are presented. D) HEK293 cells were transiently transfected with ODC, ODC plus hRS1-Reg or with ODC plus control vector. After overnight expression the cells were lysed and ODC activity was determined by measuring released CO2 E) 80 ng of purified ODC was incubated for 1 h at 37° C. in 1 ml containing 100 μM QEP or 100 μM PEQ and ODC activity was measured as in FIG. 23D. In D and E mean values±SE from 3-5 independent experiments are indicated. ***P<0.001 for difference to controls measured by ANOVA with posthoc Tukey comparison.

EXAMPLE 1: MATERIALS AND METHODS

Synthesis of Peptides.
Peptides were synthesized employing the Fmoc (N-(9-fluorenyl)methoxycaronyl) strategy as described (Vemaleken (2007) J Biol Chem. 282, 28501-28513).

Human Small Intestine.
Jejunal segments which were routinely dissected during bariatric operations of highly obese patients were stored for 1-3 h on ice in Dulbecco's modified Eagle's medium containing 5 mM D-glucose. The mucosa was isolated and circular areas of the mucosa were dissected using a punching instrument. The mucosal pieces were washed three times at 37° C. with Krebs-Ringer buffer (25 mM HEPES, 108 mM NaCl, 4.8 mM KCl, 1.2 mM KH2PO4, 1.2 mM CaCl2, pH 7.4) containing 5 mM D-glucose before uptake measurements were performed.

Expression and Purification of RS1-Reg and RS1-Reg Mutants.
*E. coli* bacteria (strain BL21 STAR) were transfected with pET21a plasmids containing His-tagged RS1-Reg or RS1-Reg and grown to mid-log phase. Protein expression was induced by isopropyl-1-thio-β-D-galactopyranoside and bacteria were grown for 3 h at 30° C. After 15 min centrifugation at 6,000×g, bacteria were washed, suspended in 20 mM Tris-HCl pH 8.0 containing 500 mM NaCl and 50 mM imidazole, lysed by sonication at 4° C., and cellular debris was removed by 60 min entrifugaton at 100 000× g. For protein purification the supernatants were mixed with $Ni^{2+}$-NTA-Agarose (Qiagen, Hilden, Germany), incubated for 1 h under rotation, and poured into an empty gravity flow columns. After extensive washing with 20 mM Tris-HCl pH 8.0 containing 500 mM NaCl and 50 mM Imidazole, protein was eluted with the same buffer containing 500 mM imidazole. Fractions containing purified protein were pooled and dialyzed against 20 mM Hepes pH 7.5 containing 150 mM NaCl or K-Ori buffer (5 mM HEPES, pH 7.6, 100 mM KCl, 3 mM NaCl, 2 mM $CaCl_2$, 1 mM $MgCl_2$).

Expression of Transporters in Oocytes of *Xenopus Laevis*.
Human SGLT1 (hSGLT1) (Vemaleken (2007) J Biol Chem. 282, 28501-13) and human CNT1 (hCNT1) (Errasti-Murugarren, Mol Pharmacol 82 (2012), 59-67) were expressed in oocytes by injection of the respective linearized, $m^7G(5')G$-capped sense cRNAs as described. Stage V or VI oocytes were obtained from anesthetized animals, defolliculated by treatment with collagenase, washed, and kept in modified Barth's solution (15 mM HEPES, pH7.6, 88 mM NaCl, 1 mM KCl, 0.3 mM $Ca(NO_3)$, 0.4 mM $CaCl_2$, 0.8 mM $MgSO_4$) containing 12.5 μg $ml^{-1}$ gentamycin (Vemaleken (2007) J Biol Chem. 282, 28501-13). Selected oocytes were injected with 50 nl of water containing cRNAs (2.5 ng of hSGLT1 or 0.5 ng of hCNT1). For expression oocytes were incubated for 2-3 days at 16° C. in modified Barth's solution with gentamycin. Noninjected control oocytes were incubated in parallel.

Injection of Polypeptides and Other Compounds into Oocytes and Uptake Measurements.
Before uptake measurements were started, 50 nl of K-Ori buffer containing peptides, polypeptides, 1 pM of calmodulin stimulated kinase 2 (CK2) inhibitor KN93 (Calbiochem San Diego. Calif.), 3 mM of the omithinedecarboxlase inhibitor difluoromethylornithine DFMO and/or or 100 pmol α-methyl-α-D-glucopyranoside (AMG) were injected and the oocytes were incubated for 1 h at room temperature. Uptake was measured in Ori buffer at room temperature. Measurements in transporter expressing oocytes were corrected for measurements in noninjected oocytes. Uptake of 50 μM [$^{14}$C]AMG was measured after 15 min incubation and washing in ice-cold Ori buffer containing 1 mM phlorizin. Uptake of 5 μM [$^3$H]uridine was measured after 15 min incubation and washing in ice-cold Ori buffer. Oocytes were solubilized in 5% (w/v) SDS and analyzed for radioactivity by scintillation counting.

Preparation of Nanohydrogels with Coupled Peptides.
Inversed miniemulsions were prepared from 2.5 ml hexane containing 50.3 mg Span 80 (Sigma, Taufkirchen, Germany) and 16.7 mg TWEEN 80™ (Sigma) and 0.4 ml 20 mM Hepes pH 7.4 containing 100 mg of thiol-functionalized linear poly(glycidol) polymer (Groll (2009) Journal of Polymer Science 47,5543-5549), 0.5 mg CGRLLRRQRRR (TAT-peptide, Peptides International, Louisville, Ky., USA), and 0.28 mg cysteine-terminated RS1-Reg peptide. In control nanohydrogels the RS1-Reg peptide was omitted. The nanogels were prepared as described (Groll (2009) Journal of Polymer Science 47,5543-5549). Shortly, the organic and aqueous phase were combined, stirred, and a miniemulsion was prepared by ultrasonication at 0° C. For formation of disulphide bridges 60 µL of 0.1 M $H_2O_2$ in water were added. The mixture was sonicated for 60 s and incubated for 25 min at room temperature. Oxidation was quenched by acidification and the nanogels were separated by centrifugation. The aqueous layer containing the nanogels was separated and washed four times with a tetrahydrofuran/water (20%/80%)-mixture to remove the surfactants and unreacted polymer. Remaining organic solvents and acid were removed by dialysis against water. The nanohydrogel suspension was stored up to two weeks stored at 4° C.

Gavage of Mice with Nanogels—

Male Rs1−/− mice or wildtype mice (Osswald (2005) Mol Cell Biol. 25, 78-87) kept on standard diet were starved over night and gavaged with 200 µl water (adjusted with HCl to pH 5.5) containing 10 mg nanohydrohydrogel that was loaded with 45 µg mRS1-Reg mutant. As a control unloaded nanohydrogel was used. After 3 hours the mice were killed and the small intestine was removed, perfused at 0° C. with Krebs-Ringer buffer (25 mM HEPES, 108 mM NaCl, 4.8 mM KCl, 1.2 mM KH2PO4, 1.2 mM CaCl2, pH 7.4) and everted using a steel rod. The jejunum was cut into 1 cm long segments.

Incubation of Small Intestinal Mucosa with Tripeptides.

Standardised t areas of human small intestinal mucosa (FIGS. 13,19) or 1 cm segments of everted mouse small intestine (FIGS. 14,15,20) were washed three times at 37° C. with Krebs-Ringer buffer containing 5 mM D-glucose and incubated for 30 min at 37° C. in Krebs-Ringer buffer containing 5 mM D-glucose plus different concentrations of tripeptides. Thereafter the tissue was washed three times at 0° C. in Krebs-Ringer buffer without glucose and uptake measurements were performed.

Measurements of AMG in Small Intestine.

For measurement of SGLT1 mediated glucose uptake, the everted segments of mouse small intestine or defined areas of human mucosa were incubated for 2 min at 37° C. with Krebs-Ringer buffer containing 10 µM [$^{14}$C]AMG with or without 0.2 mM phlorizin. Uptake was stopped by transferring the segments into ice cold Krebs-Ringer buffer containing 0.2 mM phlorizin for 5 min. After washing with ice cold Krebs-Ringer buffer the intestinal segments or pieces of human mucosa were dissolved in 0.5 ml Soluence-350) (Perkin Elmer Inc. Waltham Mass., USA). Radioactivity was analysed by liquid scintillation counting. Phlorizin inhibited AMG uptake per cm length or per standard area of the mucosa was calculated.

Oral Glucose Tolerance Test.

Glucose and insulin in the blood was measured after 18 h of fasting at 10 a.m. (time 0) and then 20, 30, 60 and 120 min after administration of 3 g D-glucose/kg body weight by oral gavage.

Measurements of Glucose and Insulin in the Blood.

Blood (2 µL) was collected from the tail vein and analysed using the amperometric glucose oxidase method (glucose meter, ACCU-CHEK Aviva). Blood insulin-Insulin was determined using the rat C-peptide ELISA from Mercodia (Uppsala, Sweden) which is based on the sandwich technique using two monoclonal antibodies directed against two different antigenic determinants on the C-peptide.

Calculations and Statistics.

Intracellular concentrations of compounds injected into oocytes were estimated by assuming and internal distribution volume of 0.4 µl ((Vemaleken (2007) J Biol Chem. 282, 28501-28513). Values are given as mean±S.E. In experiments with oocytes, at least 24 individual measurements with transporter expressing oocytes were performed using three different oocyte batches. The curves were obtained by fitting the Hill equation to the data. The Hill equation was fitted to concentration inhibition curves and $IC_{50}$ values were calculated. For comparison of mean values from 3 or more groups the ANOVA test and posthoc Tukey comparison was performed. For comparison of mean values from 2 groups the Student's t-test for unpaired samples was employed.

EXAMPLE 2: FINDINGS ON THE FUNCTION OF RS1 THAT PROVIDED THE BASIS FOR DEVELOPMENT OF COMPOUNDS THAT DOWNREGULATE SMALL INTESTINAL GLUCOSE ABSORPTION AFTER A GLUCOSE-RICH MEAL

The posttranslational regulation of hSGLT1 by hRS1 and the peptides requires binding of hRS1 to a complex high affinity binding site allowing interaction with QSP and SDSDRIEP.

Amino acids 16-98 of hRS1 contain two QSP motifs and the SDSDRIEP motif (FIG. 1). The hRS1 fragment 16-98 (hRS1-Reg) contains an hRS1 domain which is responsible for posttranslational downregulation of SGLT1 (and hCNT1). hSGLT1 or hCNT1 were expressed in oocytes of *Xenopus laevis* by injection of the respective transporter cRNA and incubating the oocytes for 2-3 days. Then different concentrations of hRS1-Reg were Injected and the phlorizin (200 µM) inhibited uptake of alpha-methyl glucoside (AMG) expressed by hSGLT1 (FIG. 2A) or the sodium dependent uptake of uridine expressed by hCNT1 (FIG. 2B) was measured. The data indicate that hRS1-Reg downregulates both hSGLT1 and hCNT1 by about 50% with a similar affinity ($IC_{50}$ values: 71±2 nM (hSGLT1), 126±6 nM (hCNT1).

To differentiate whether hRS1-Reg down-regulates different transporters in parallel or is able to down-regulate individual transporters separately it was investigated whether the down-regulation of hSGLT1 and hCNT1 by hRS1-Reg is prevented when the intracellular concentration of AMG was increased above a concentration of 0.1 mM. Previously it had been observed that down-regulation of hSGLT1 by the tripeptides QSP and QCP was blunted when the intracellular AMG concentration was higher than 0.1 mM (Vemaleken, J Biol Chem 282 (2007), 28501-28513, FIG. 5C). Our previous studies showed that this glucose effect must be due to glucose binding downstream RS1 because it was observed with tripeptide motifs of hRS1 which cannot include a glucose binding site. It remained unclear whether the effect of glucose is due to an effect on the affinity of the RS1-Reg receptor or to an effect of glucose on a downstream step of the regulation. To differentiate between these possibilities the affinity of hRS1-Reg for down-regulation of hSGLT1 was measured using the oocyte expression system without injecting AMG Into the oocytes (intracellular AMG<10 iM) or after injecting 250 µM AMG. It was observed that the affinity of hRS1-Reg for downregulation of hSGLT1 was decreased 8 fold when the intracellular concentration of AMG was increased to 250 µM (FIG. 3A) whereas the affinity of hRS1-Reg for downregulation of hCNT1 was not altered (FIG. 3B).

The data indicate that glucose decreases the affinity for binding of hRS1-Reg to a receptor that down-regulates SGLT1 but does not change the affinity to a receptor which is responsible for down-regulation of hCNT1. Employing two-hybrid screening, immunoprecipitation and functional studies it was detected that ornithinedecarboxylase (ODC) is the RS1-Reg receptor which is responsible for glucose dependent regulation of SGLT1 and that ODC contains a glucose binding site (see, for example, FIG. 23). The data indicate that hRS1-Reg activates a glucose dependent mechanism for down-regulation hSGLT1 and a glucose independent mechanism for down-regulation of hCNT1. They suggest that hRS1-Reg can regulate different transporters by addressing different receptors at the Golgi apparatus that mediate the release of different vesicle populations containing different transporters. hRS1-Reg contains many conserved consensus sequences for phosphorylation (FIG. 1).

To investigate whether the phosphorylation pattern of hRS1-Reg may determine which transporter is regulated, serine residues in positions 45 and 83 which are located within predicted phosphorylation sites for protein kinase C (PKC) and calmodulin stimulated kinase 2 (CK2), respectively, were replaced (FIG. 1) either by alanine—to prevent phosphorylation—or by glutamate—to mimic phosphorylation—, and the effects of the mutations on the affinity for down-regulation of hSGLT1 or for down-regulation of hCNT1 were measured (FIG. 4). The affinity of hRS1-Reg wildtype for downregulation of hSGLT1 is similar to hRS1-Reg(S45A) (FIG. 4A) whereas the affinity of hRS1-Reg wildtype for downregulation of hCNT1 is similar to hRS1-Reg(S45E) (FIG. 4B). Mimicking phosphorylation in position 45 increases affinity for downregulation of hSGLT1 (FIG. 4A) and decreases affinity for downregulation of hCNT1 (FIG. 4B). The affinity of hRS1-Reg wildtype for downregulation of hSGLT1 is similar to the affinity of hRS1-Reg(S83E) suggesting that serine in position 83 is phosphorylated in hRS1-Reg wildtype (FIG. 4C). When phosphorylation of serine 83 is prevented by exchange with glutamate (hRS1-Reg(S83E)) or by blocking CK2 activity by the specific CK2 inhibitor KN93 the affinity for down-regulation of hSGLT1 is largely increased (FIG. 4C). In contrast to regulation of hSGLT1 the affinity of hRS1-Reg for down-regulation hCNT1 is not influenced when phosphorylation of serine 83 is prevented or mimicked (FIG. 4D). The data indicate that the phosphorylation pattern of hRS1-Reg determines which transporter is downregulated by a critical intracellular concentration of hRS1-Reg.

Since the phosphorylation pattern of hRS1-Reg influences the affinity for glucose dependent down-regulation of hSGLT1 versus the affinity for glucose independent down-regulation of hCNT1 it was tested whether the phosphorylation pattern of hRS1-Reg is critical for the glucose dependence of the regulation of hSGLT1. Glucose binding to ODC may alter the structure of the binding site for hRS1-Reg and differentially phosphorylated hRS1-Reg may have different affinities to the glucose modified hRS1-Reg binding site of ODC. To determine whether the affinities of mutant hRS1-Reg(S45E) or hRS1-Reg(S45A) are decreased in the presence of intracellular AMG as has been observed for hRS1-RS1 wildtype (FIG. 3A) the affinity of hRS1-Reg(S45E) or hRS1-Reg(S45A) was measured without and with injection of AMG (FIG. 5A). After exchange of serine 45 to alanine or to glutamate the effect of AMG on the affinity was abolished. This indicates that serine 45 in hRS1-Reg is critical for differentiation of hRS1-Reg binding between ODC without bound glucose and ODC with bound glucose (ODC-glucose).

Testing whether the phosphorylation of serine 83 in the CK2 phosphorylation site is Involved in the glucose dependent down-regulation of hSGLT1 it was investigated whether the affinity of hRS1-Reg wildtype is decreased after inhibition of CK2 by inhibitor KN93 which leads to dephosphorylated serine in position 83 and increased affinity (FIG. 5B). After inhibition of CK2 the affinity of hRS1-Reg was drastically decreased by intracellular AMG. The data show that serine 83 is not critical for the recognition of structural differences between the RS1-Reg binding site of ODC without bound glucose (ODC-glucose).

Since only the tripeptide motif QSP In positions 19-21 of human hRS1-Reg is conserved in mice (FIG. 6) It was tested whether phosphorylation of serine 20 may have an effect on the affinity of hRS1-Reg to down-regulate hSGLT1 and on the glucose dependence of this down-regulation.

Figure 7:
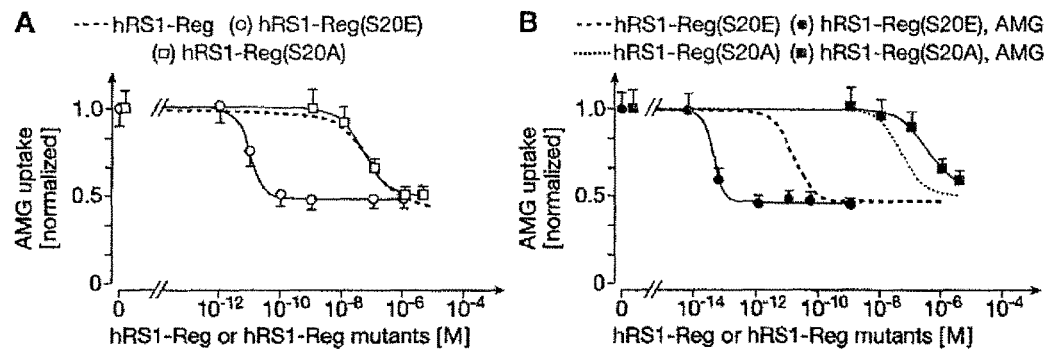

FIG. 7 shows that this is the case. Preventing phosphorylation at serine in position 20 in hRS1-Reg(S20A) does not alter the affinity for downregulation of hSGLT1 (FIG. 7A) indicating that hRS1-Reg wildtype is not phosphorylated at low intracellular glucose. At high intracellular glucose the affinity of hRS1-Reg(S20A) for downregulation is decreased by a factor of 7-8 similar to hRS1-Reg wildtype (compare FIG. 7B with FIG. 3A).

Mimicking phosphorylation in the hRS1-Reg(S20E) mutant increased the affinity compared to hRS1-Reg wildtype or hRS1-Reg(S20A) by a factor of 4000-6000. In the presence of high intracellular glucose the affinity of hRS1-Reg(S20A) was decreased compared to low intracellular glucose as observed with hRS1-Reg wildtype by 300 times. Thus in the presence of intracellular glucose the affinity of hRS1-Reg(S20E) was 15 Mill times higher compared to hRS1-Reg wildtype. The data indicate that serine 20 in hRS1-Reg is critical for differentiation of hRS1-Reg binding between ODC without bound glucose and ODC with bound glucose (ODC-glucose).

EXAMPLE 3: IN THE OOCYTE EXPRESSION SYSTEM, hRS1-REG(S20E) HAS A HIGHER AFFINITY THAN hRS1-REG WILDTYPE AND hRS1-REG(S20A) FOR DOWN-REGULATION OF EXPRESSED hSGLT1 IN THE PRESENCE OF HIGH INTRACELLULAR GLUCOSE

In hSGLT1 expressing oocytes, the effects of injection of different concentrations of hRS1-Reg wildtype and hRS1-Reg(S20E) on the activity of hSGLT1 mediated AMG uptake were measured at low (<1 M) and high intracellular concentrations of AMG (~250 µM) (FIG. 7). The $IC_{50}$ value of hRS1-Reg(S20E) for downregulation of hSGLT1 at low intracellular AMG is 6300 times lower as compared to hRS1-Reg wildtype. In the presence of high intracelluar AMG the $IC_{50}$ value for down-regulation hSGLT1 by hRS1-Reg wildtype was increased 8 fold whereas the $IC_{50}$ value for down-regulation of hSGLT1 by hRS1-Reg (S20E) was decreased 300 fold so that the affinity for down-regulation of hSGLT1 by hRS1-Reg(S20E) at high intracellular glucose was 15 Mill higher as compared to hRS1-Reg wildtype. The data indicate that serine 20 in hRS1-Reg is critical for differentiation of hRS1-Reg binding between ODC (ODC without bound glucose) and ODC-glucose (ODC with bound glucose). They show that hSGLT1-Reg(S19E) is capable to down-regulate glucose absorption in humans after a glucose-rich meal.

EXAMPLE 4: QEP DOWNREGULATES hSGLT1 IN THE PRESENCE OF HIGH INTRACELLULAR GLUCOSE IN CONTRAST TO TRIPEPTIDE QSP EMPLOYING THE OOCYTE EXPRESSION SYSTEM

The improved understanding of the posttranslational regulation of transporters by hRS1 implicated that different QXP peptides may have different affinities for down-regulation of SGLT1 e.g. for binding to ODC. It also implicated that different QXP peptides may exhibit different glucose-induced affinity changes for down-regulation of hSGLT1 e.g. for binding to ODC without bound glucose versus binding to ODC with bound glucose. There was a probability that all QXP-type tripeptides are not capable to down-regulate the hSGLT1 expression in the presence of high intracellular glucose concentrations or have a very low affinity for down-regulation of hSGLT1 as has been observed for hRS1-Reg wildtype. Since high glucose concentrations are expected in enterocytes after ingestion of glucose-rich food, it appeared to be possible that all QXP peptides are not able to downregulate SGLT1 in the luminal membrane of enterocytes after a glucose-rich meal. When the carbohydrate content in small intestine between meals or overnight is low, the QXP peptides were supposed to be active. However, in this situation endogenous RS1 should be also active so that the possibility was considered that the QXP-type tripeptides may not induce an additional down-regulation.

To check the potential of different QXP type tripeptides for downregulation of hSGLT1 at low intracellular glucose concentrations in the absence of endogenous RS1 the inhibition of hSGLT1 mediated uptake of [$^{14}$C]AMG observed after injection of 1 μM and 50 nM of different QXP tripeptides using the oocytes expression system was measured (FIG. 8). Whereas all tested tripeptides inhibited SGLT1 mediated transport at 1 μM, inhibition at 50 nM was only observed with tripeptides QSP, QEP and QAP. The data suggest higher affinities of QSP, QEP and QAP as compared to QDP, QTP, QMP, QIP and QVP at low intracelluar glucose concentrations.

Since hRS1-Reg does not only inhibit the expression of hSGLT1 posttranscriptionally but also the expression of the Na+-nucleoside transporter CNT1 and CNT3 (Errasti-Murugarren loc. cit.) the transporter selectivity of QEP and QSP at low intracellular glucose concentration in the absence of endogenous RS1 in comparison to hRS1-Reg and SDS-DRIEP using the oocytes expression system (FIG. 9) was determined. Uptake of 5 μM [$^3$H]uridine expressed by the nucleoside transporters hCNT1 or hCNT3 was decreased when hRS1-Reg and SDSDRIEP were injected whereas QSP or QEP were not able to inhibit transport expressed by hCNT1 or hCNT3. The data show that QSP and QEP are selective for SGLT1 versus CNT1 and CNT3 and suggest that QXP tripeptides are selective for SGLT1 versus other transporters regulated by RS1-Reg.

Previously it was shown that hSGLT1 expression in oocytes was inhibited 40-50% after injection of 200 nM QSP in the absence of injected intracellular AMG (intracellular AMG<10 μM) and that this inhibition was abolished after injection of AMG leading to intracellular concentrations of AMG higher than 250 μM (Vernaleken loc. cit.). Measuring the concentration dependence of intracellular QSP for down-regulation of SGLT1 without injection of AMG a $C_{50}$-value of 0.2 nM (FIG. 10) was determined. However, in the presence of 250 μM intracellular AMG the effect of QSP on hSGLT1 expression was abolished. The AMG dependent blunting of the QSP effect suggests that QSP does not reduce glucose absorption in small intestine after a glucose-rich meal.

Without injection of AMG QEP Inhibited SGLT1 mediated AMG uptake by about 40% with an $IC_{50}$ value of 7.9+0.8 nM (FIG. 11). This value is about 40 times higher as compared to QSP observed without injection of AMG. With injection of AMG (intracellular AMG~0.25 mM) QEP inhibited SGLT1 expression by about 50% and exhibited an affinity that was increased more than 15000 fold as compared to low intracellular AMG. The $IC_{50}$ value of QEP in the presence of about 0.25 mM intracellular AMG was 0.2+0.3 pM. Thus QEP is an inhibitor of hSGLT1 expression in the presence of high intracellular glucose with an affinity that is about 1000 times higher than the affinity of QSP in the presence of low intracellular glucose concentrations.

Taken together the data indicate that QEP is a hSGLT1 specific posttranslational inhibitor that down-regulates the expression of hSGLT1 with very high affinity in the presence of a high intracellular concentration of glucose. In contrast to QSP, QEP is supposed to be capable to inhibit small intestinal glucose absorption after a glucose-rich meal.

EXAMPLE 5: QEP IS ABLE TO DOWNREGULATE mSGLT1 AND TO DECREASE GLUCOSE ABSORPTION IN SMALL INTESTINE USING MICE IN WHICH ENDOGENEOUS MOUSE RS1 WAS REMOVED

To compare the potential of QEP versus QSP to down-regulate the expression of SGLT1 in vivo Balbc mice were employed in which endogenous mRS1 was removed genetically (Osswald, Mol Cell Biol 25 (2005), 78-87) to avoid an interaction with endogenous RS1. RS1-/- mice that were starved over night were gavaged with 200 μl PBS or 200 μl PBS containing 100 mM QEP or 100 mM QSP. This represents application of 20 μmol of QEP or QSP per mouse. After 2 h the animals were killed, their small intestines were everted and phlorizin inhibited uptake of 10 μM [$^{14}$C]AMG Into segments of the everted jejunum was measured (FIG. 12A). After gavage with QEP the uptake of AMG was decreased about 30% whereas QSP showed no significant effect. To determine whether the down-regulation of SGLT1 by QEP has an effect on glucose absorption RS1-/- mice were gavaged with 200 μl PBS buffer or 200 μl PBS buffer containing 20 μmol QEP, gavaged the mice 3 h later with 400 μl water containing 40% (w/v) D-glucose and measured the plasma D-glucose 15 min later (FIG. 12B). The plasma concentration was significantly reduced. The data demonstrate that QEP is able to down-regulate mSGLT1 in mouse small intestine and thereby decrease the small intestinal absorption of glucose.

EXAMPLE 6: QEP IS ABLE TO DOWNREGULATE mSGLT1 IN WILDTYPE MICE IN THE PRESENCE OF HIGH INTRACELLULAR GLUCOSE

To determine whether QEP down-regulates mSGLT1 in small intestine of wildtype mice, ex vivo experiments were performed in which everted small intestinal segments in the absence or presence of 5 mM D-glucose without and with QEP were incubated and mSGLT1 mediated transport activity to detect down-regulation of mSGLT1 was measured. In a first series of experiments segments of jejunum of wildtype mice were incubated for 30 min at 37° C. with culture medium containing 5 mM D-glucose (pH 6.4) or with culture medium containing 5 mM D-glucose and 5 mM QEP. Thereafter the segments were washed with PBS buffer and phlorizin inhibited uptake of 10 μM [$^{14}$C]AMG was measured. Under these conditions no effect of QEP on SGLT1 mediated AMG uptake was observed (data not shown). Reasoning that QEP may not be effective because posttranslational down-regulation of mSGLT1 via the RS1 related mechanism may be maximally activated by endogenous mRS1 it was investigated whether QEP down-regulates SGLT1 in the presence of extracellular glucose leading to a high intracellular glucose concentration. When the jejunal segments were incubated for 30 min at 37° C. without and with 5 mM QEP in the presence of 5 mM D-glucose, SGLT1 mediated uptake of 10 μM [$^{14}$C]AMG was decreased 30% after incubation with QEP whereas incubation with 5 mM QSP had no significant effect (FIG. 13A). A similar result was obtained when the experiment was performed with RS1−/− mice (FIG. 13B). The data indicate that, in contrast to QSP, QEP is able to down-regulated SGLT1 in mouse small intestine after a glucose-rich meal. They suggest that endogenous mRS1 is not effective in the presence of high intracellular glucose concentrations.

EXAMPLE 7: QEP IS ABLE TO DOWNREGULATE hSGLT1 IN HUMAN SMALL INTESTINE IN THE PRESENCE OF HIGH INTRACELLULAR GLUCOSE

Next, it was investigated which of the QXP-type tripeptides are capable to downregulate hSGLT1 expression in human small intestine in the presence of high glucose. Jejunal samples that were obtained during bariatric surgery of obese patients (males and females with a mean age of 50 years with a mean body mass index of 50) were used. Similar tripeptide effects were observed with males and females. A part of the jejumum which is routinely removed during bariatric surgery, was carried to the laboratory using ice-cold culture medium containing 6 mM D-glucose. Part of the mucosa was dissected and identical areas of the mucosa were isolated using a punching instrument. The mucosal pieces were washed with glucose free buffer and incubated for 30 min at 37° C. in tissue culture medium (pH 6.4) containing 5 mM D-glucose and different QXP-type tripeptides. Thereafter the sample were washed two times with PBS buffer (pH 7.4, 37° C.) and incubated for 2 min at 37° C. in PBS (pH 7.4) containing 100 mM sodium and 10 μM [$^{14}$C]AMG. The incubation was performed in the absence and presence of 200 μM of the SGLT1 inhibitor phlorizin. Thereafter the samples were washed with ice-cold PBS, the tissue was dissolved, and radioactivity was determined by liquid scintillation counting. The phorizin inhibited AMG uptake was calculated. FIG. 14 shows that QEP was the only tripeptide which decreased phlorizin inhibited AMG uptake into the mucosa representing transport activity of hSGLT1.

To determine whether QEP down-regulates hSGLT1 in human small intestine at low concentrations of intracellular glucose human jejunum obtained from bariatric operations was washed with PBS and mucosal pieces were incubated for 30 min at 37° C. with PBS or with PBS containing 5 mM QEP. After washing phlorizin inhibited uptake of 10 μM [$^{14}$C]AMG was measured. Under these conditions QEP did not decrease SGLT1 mediated AMG uptake (data not shown) suggesting that endogenous RS1 mediates maximal down-regulation of hSGLT1 at low concentrations via the RS1 dependent pathway.

Like QSP and the other QXP type tripeptides QEP is taken up into enterocytes by the peptide transporter PEPT1 and acts at the Golgi apparatus. The effect is influenced by the velocity of uptake, the intracellular degradation and potential cellular release. To determine the concentration dependence of QEP for down-regulation of hSGLT1 and maximal effect of QEP under the employed experimental conditions human small intestinal pieces were Incubated in the presence of 5 mM D-glucose for 30 min at 37° C. with different concentrations QEP and measured hSGLT1 mediated uptake of AMG (FIG. 15). Small but not statistically significant effects were observed with 0.1 and 0.5 mM QEP. With 1 mM QEP significant downregulation of SGLT1 by 40%, with 5 mM QEP downregulation of hSGLT1 by 55% and with 15 mM QEP downregulation of SGLT1 by 75% was observed. The data indicate that QEP is capable to downregulate hSGLT1 in human small intestine after a glucose-rich meal by 75%.

EXAMPLE 8: QEP INCREASES THE INSULIN SENSITIVITY FOR DECREASING SERUM GLUCOSE

It has been reported that inhibition of SGLT1 in the small intestine or genetic removal of SGLT1 leads to an increase of GLP-1 secretion 30 min—2 h after gavage with glucose (Powell loc. cit). Since antidiabetic drugs increasing GLP-1 in the serum are employed for treatment of diabetes type 2, inhibition of SGLT1 mediated glucose absorption during a glucose rich meal by SGLT1 inhibitors or by down regulation of SGLT1 with QEP might be beneficial for the treatment of diabetes. Considering expression of SGLT1 in enterocytes of the proximal small intestine and in L-cells of distal small intestinal the mechanism how inhibition or down-regulation of SGLT1 increases GLP-1 secretion is explained as follows. Inhibition or down regulation of SGLT1 in the enterocytes decreases glucose absorption in small intestine and thereby increases die glucose concentration in distal small intestine. Since SGLT1 in the L-cells should be inhibited or down-regulated in parallel to SGLT1 in enterocytes, the increased secretion of GLP-1 is supposed to be due to an increased concentration of short chain fatty acids in distal small intestine which are formed by bacteria metabolizing the increased amount of glucose which enters distal small intestine.

Since it was observed that in mice where SGLT1 was genetically removed (SGLT−/− mice) the basal concentration of insulin in the serum was decreased and the insulin sensitivity was increased (data not shown) It was investigated whether a prolonged oral application of QEP influences basal serum insulin and insulin secretion during an oral glucose tolerance test (OGTT). 5 mM QEP was added to the drinking water of New Zealand obese (NZO) mice that have a genetic disposition for diabetic type 2 (Vogel, Horm Metab Res 45 (2013), 430-435). In contrast to a gavage with 100 mM QEP 2 h before removal of the small intestine or performing an OGTT (FIG. 12, FIG. 13, FIG. 16 A, B), SGLT1-mediated AMG transport into enterocytes and glucose absorption during an OGTT was not decreased when 5 mM QEP was added for 3 days to the drinking water of mice (FIG. 17A, B). Whereas 5 mM QEP In the drinking water exhibited no effect on the increase and decrease of serum glucose after gavage with glucose (FIG. 17A, B), it decreased the basal concentration of insulin in the serum by 50% and also decreased the increase of serum insulin observed after gavage with glucose (FIG. 17C). In spite of the poor increase of the insulin concentration in the blood after gavage with glucose observed in animals treated with QEP, the increased blood glucose after gavage with glucose decreased as rapid as in control animals. Because the decrease of blood glucose in the OGTT is due to effects of insulin in peripheral tissues that are mediated by the insulin receptor, the insulin sensitivity has been increased after treatment with QEP.

EXAMPLE 9:
GLUTAMINE-SERINETHIOPHOSPHATE-PROLINE ($QS_{thiophosphate}P$) DOWN-REGULATES hSGLT1 IN THE PRESENCE OF HIGH INTRACELLULAR GLUCOSE EMPLOYING THE OOCYTE EXPRESSION SYSTEM Since QEP in which phosporylation of serine in QSP is mimicked by replacement of serine with glutamate was active in the presence of high intracellular glucose the effect of glutamine-serinethiophosphate-proline (QS thiophoshate P) on the expression of hSGLT1 in oocytes without injection of AMG (intracellular AMG<10 µM) and with injection of AMG (intracellular AMG~0.25 mM) was tested. Without injection of AMG, hSGLT1 was down-regulated after injection of 500 pM QS thiophoshate P but not after injection of 5 pM QS thiophoshate P (FIG. 18) showing a similar affinity as QSP (see FIG. 11). When the Intracellular concentration of AMG was increased to ~0.25 mM by AMG Injection, the expression of hSGLT1 was down-regulated by both 500 pM and 5 pM QS thiophoshate P (FIG. 18). Noteworthy the degree of down-regulation obtained with 5 pM QS thiophoshate P (~75%) was higher compared to 5 pM QEP (~45%, see FIG. 11).

$QS_{thiophosphate}P$ is Able to Downregulate mSGLT1 in mRS1−/− Mice and Wildtype Mice in the Presence of High Intracellular Glucose:

To demonstrate activity of $QS_{thiophosphate}P$ in small intestine of mice in the presence of high intracellular glucose, inverted small intestinal segments of mRS1−/− mice and wild type mice were incubated for 30 min at 37° C. with PBS containing 5 mM D-glucose without or with 5 mM QEP (FIG. 10). After washing with PBS, uptake of 10 µM [$^{14}$C]AMG was measured in the absence and presence of 200 µM phlorizin. Phlorizin inhibited uptake mediated by SGLT1 was significantly inhibited in SGLT1−/− and wild type mice. The data indicate that $QS_{thiophosphate}P$ is able to down-regulate SGLT1 in mouse small intestine after glucose-rich meals.

$QS_{thiophosphate}P$ is Able to Down-Regulate hSGLT1 in Human Small Intestine in the Presence of High Intracellular Glucose.

To determine whether $QS_{thiophosphate}q$ is also active in humans, equally sized pieces of jejunum obtained from bariatric operations were incubated for 30 min at 37° C. with culture medium containing 5 mM D-glucose without $QS_{thiophosphate}P$ or with different concentrations of $QS_{thiophosphate}P$. After washing with PBS, phlorizin-inhibited uptake of 10 µM [$^4$C]AMG which is mediated by hSGLT1 was measured. hSGLT1-mediated AMG uptake was inhibited ~30% by 5 mM $QS_{thiophosphate}P$ and ~40% by 15 mM $QS_{thiophosphate}P$ (FIG. 20).

EXAMPLE 10: IT IS POSSIBLE TO DOWN-REGULATE SGLT1 AFTER INTRODUCING ORAL APPLIED RS1-REG INTO ENTEROCYTES BY COUPLING TO HYDROGEL NANOPARTICLES

Figure 21:
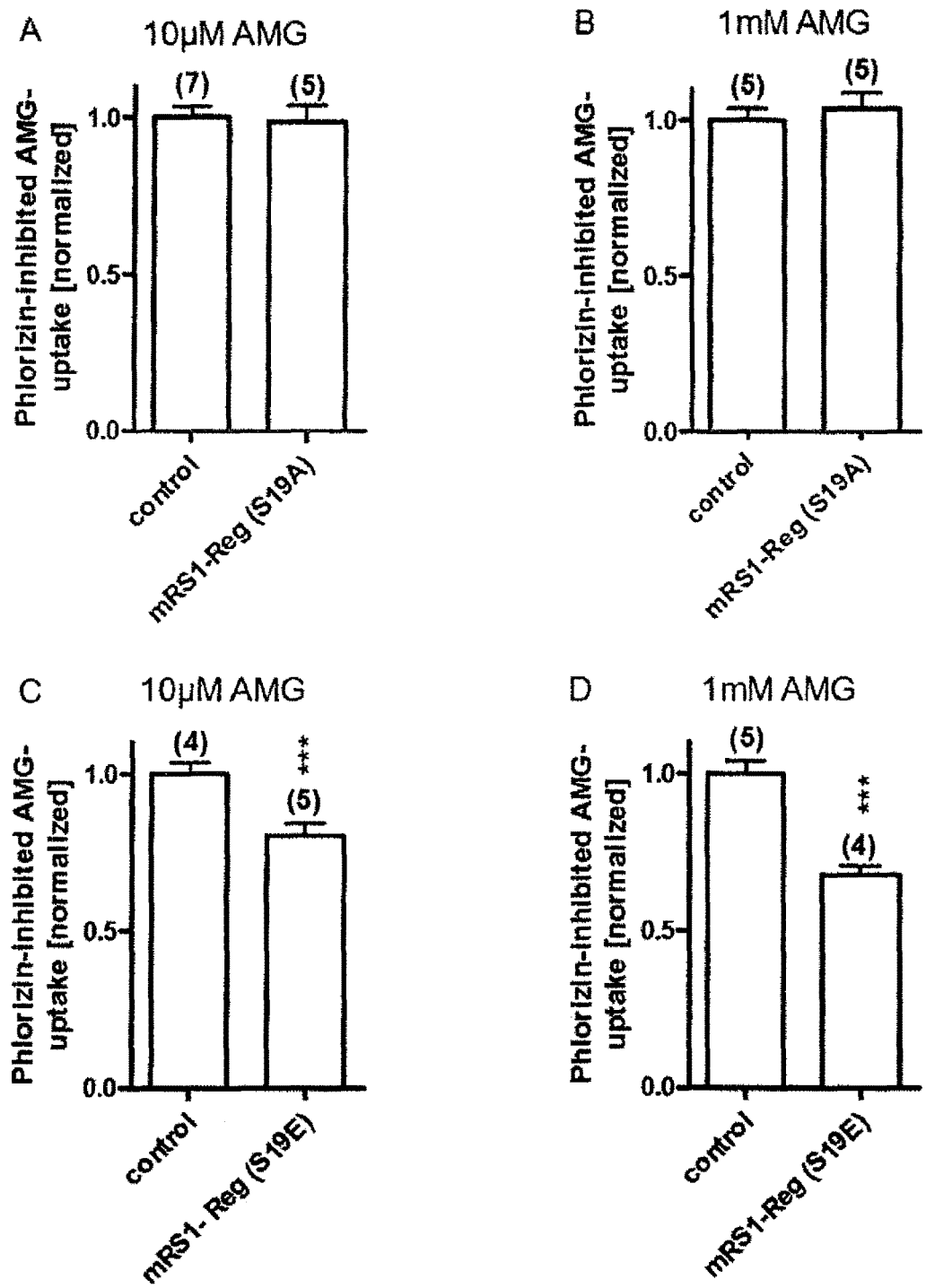

As mentioned above, hRS1-Reg derivatives that mimic specific phosphorylation patterns of hRS1-Reg provide an excellent possibility for selective addressing of hSGLT1 and for down-regulation of hSGLT1 after glucose-rich meals. In order to employ such hRS1-Reg mutants for oral application a method to introduce hRS1-Reg mutants efficiently into cells was found. For this purpose, mutants from RS1-Reg from mRS1 were coupled by disulfide linkage to biocompatible and degradable hydrogel nanoparticles (NPs) which are composed of thiol-functionalized polymers based on linear (poly)glycidols or star-shaped (poly)ethylene oxide-stat-propylene oxide (Groll, Journal of Polymer Science 47 (2009), 5543-5549). To validate the potential for down-regulation of SGLT1 in small intestine by RS1-Reg coupled to nanoparticles after oral application, mice in which endogenous RS1 was genetically removed (RS1−/− mice) were used as animal model. Using RS1−/− mice, the possibility that endogenous RS1 covers effects of introduced RS1-Reg was avoided. To avoid running into problems related to species differences, the experiments were performed with RS1-Reg from mouse (mRS1-Reg). In order to exclude unspecific effects due to unloaded nanoparticles (NPs), control experiments with unloaded NPs were performed. To exclude nonspecific effects of incorporated mRS1-Reg on SGLT1 expression that may result from effects on general cell functions, effects on SGLT1 expressions which are dependent on individual amino acids in mRS1-Reg were detected. Therefore, it was searched for effects correlated with mutants of serine 19 in mRS1-Reg which is located in the single QSP motif in mRS1-Reg (FIG. 21).

RS1−/− mice starved overnight were gavaged with 200 µl empty NPs (control) or 200 µl NPs loaded with 1 nmol mRS1-Reg(S19A) or 1 nmol mRS1-Reg(S19E). This represents 20000 times less mol of RS1-Reg mutants as compared to mol QEP used for gavage. 2 h after gavage with mRS1-Reg mutants coupled to NPs, phlorizin (200 µM) Inhibited uptake of 10 µM AMG labelled containing tracer [$^{14}$C]AMG after 2 min incubation at 37° C. (FIG. 21A, C) or uptake of 1 mM AMG labelled with tracer [$^{14}$C]AMG after 2 min incubation at 37° C. was measured (FIG. 21B, D). Since previous experiments showed that RS1-Reg down-regulates the concentration of SGLT1 in the plasma membrane and does not change the substrate affinity of SGLT1, the transport activities measurements with 10 µM and 1 mM AMG represent the amount of SGLT1 within the luminal membrane of the enterocytes. Since AMG is rapidly transported by mSGLT1 into the enterocytes the intracellular concentration increases within seconds to values higher than 0.25 mM when the cells were incubated with 1 mM AMG. Gavage with mRS1-Reg(S19A) coupled to NPs did not alter the expression of SGLT1 as indicated by the missing effect of phlorizin-inhibited uptake of 10 µM and 1 mM AMG. In contrast phlorizin-inhibited uptake of 10 µM AMG or 1 mM AMG was inhibited by 26 and 30% respectively. The data indicate that coupling of RS1-Reg to NPs provides a method to introduce RS1-Reg effectively into enterocytes after oral application. The data indicate that mimicking phosphorylation of serine 19 in mRS1-Reg after exchange with glutamate increases the capacity for down-regulation of mSGLT1 which is supposed to be due to an increase of the affinity for binding to the receptor ODC. The data further indicate that gavage of a mouse with 1 nmol mRS1-Reg (S19E) is sufficient to downregulate SGLT1 in the presence of low and high intracelluar glucose.

EXAMPLE 11: MIMICKING PHOSPHORYLATION IN THE N-TERMINAL QSP MOTIF OF RS1-REG LEADS TO THE CAPABILITY OF RS1-REG TO DOWN-REGULATE SGLT1 IN SMALL INTESTINE AFTER A GLUCOSE RICH-MEAL

It was investigated whether mimicking the phosphorylation of serine 19 in mRS1-Reg by exchange with glutamate enables mRS1-Reg to down-regulate mSGLT1 in mouse small intestine of wildtype mice in the presence of high intracellular glucose concentrations which are observed after glucose rich meals. Wild type mice contain endogenous mRS1 that down-regulates SGLT1 when the intracellular concentration of glucose is low as observed in the night or between meals. At low intracellular glucose endogenous mRS1-Reg in mRS1 is supposed to exhibit a phosphorylation pattern that allows high affinity binding to ODC that mediates the down-regulation of mSGLT1. Under these conditions an active motif of mRS1-Reg such as QEP or an active mRS1-Reg domain such as mRS1-Reg(S19E) may not be able to induce a further down-regulation of mSGLT1 on top of endogenous mRS1-Reg. In contrast endogenous RS1-Reg is not active when the intracellular glucose concentration is high as observed after glucose rich meals because the mRS1-Reg binding site of ODC has been modified by glucose binding to ODC (ODC-glucose) and/or intracellular glucose may have altered the phosphorylation pattern of mRS1-Reg. Under this condition QEP or modified mRS1-Reg domain that binds to ODC-glucose may induce down-regulation of mSGLT1.

It was observed that the glucose induced upregulation of SGLT1 in mouse small intestine which is due to glucose dependent blunting of the RS1-Reg induced inhibition of SGLT1 expression occurs within seconds (unpublished data). For this reason the effects observed after gavage with mRS1-Reg(S19E) mutant on transport activity mSGLT1 in the luminal membrane of the enterocytes at low or high intracellular concentrations of intracellular AMG by measuring uptake after 2 min incubation with 10 µM AMG (low intracellular AMG) or of 1 mM AMG (high intracellular AMG) was tested. During the uptake measurements the intracellular concentration of AMG increases to 5-10 times of the value in the incubation medium.

Wild type mice starved overnight were gavaged with 200 µl empty NPs (control) or 200 µl NPs loaded with 1 nmol mRS1-Reg(S19E) (FIG. 22A, B) or with 1 nmol wildtype mRS1-Reg (FIG. 22C). Two hours later phlorizin (200 µM) Inhibited uptake of 10 µM AMG (FIG. 22A) or of 1 mM AMG (FIG. 22B,C) was measured at 37° C. using an incubation time of 2 min. Whereas uptake of 10 µM AMG (representing uptake at low intracellular glucose) was not altered after gavage with NPs loaded with mRS1-Reg (S19E), uptake of 1 mM AMG (representing uptake at high intracellular glucose) was decreased by 40% (FIGS. 22A, B). In contrast to mRS1-Reg(S19E), uptake of 1 mM AMG was not altered after gavage with NPs loaded with wildtype mRS1-Reg (FIG. 22C). The data show that the amount of mSGLT protein in the brush-border membrane of mouse enterocytes can be down-regulated by mRS1-Reg(S19E) in the presence of high intracellular glucose.

EXAMPLE 12: ORNITHINE DECARBOXYLASE (ODC) IS THE RS1-REG RECEPTOR FOR DOWN-REGULATION OF SGLT1 AND THAT BINDING OF QEP TO ODC INHIBITS ODC ACTIVITY

Polyamines, including putrescine, are involved in various cellular regulations including transcription, cellular division and posttranscriptional regulations (Wallace, Biochem J 378 (2003), 1-14). The concentration of putrescine in various intracellular compartments is determined by the enzymatic activity of ODC in different intracellular locations which generates putrescence by decarboxylation of ornithine. Since putrescine degrades rapidly the subcellular locations of ODC determine the local concentrations of putrescine. The local putrescine concentrations trigger various different regulatory mechanisms which include the activity of plasma membrane proteins and intravesicular trafficking (Kanerva, Exper Cell Research 316 (2010), 1896-1906).

Employing two-hybrid screening and immunocoprecipitation experiments evidence was provided that hRS1-Reg binds to ODC (data not shown). It was shown that the release of SGLT1 containing vesicles from the Golgi apparatus was blocked by specific ODC Inhibitor difluoromethylornithine (DFMO) and that the DFMO effect was blunted when putrescine was added (FIG. 23A). Since hRS1-Reg and DFMO down-regulate hSGLT1 to a similar degree and the down-regulations were not additive, RS1-Reg and ODC employ the same pathway for down-regulation of hSGLT1. FIG. 23B shows that the down-regulation of hSGLT1 expression in oocytes via hRS1-Reg was blunted when putrescine was added suggesting that hRS1-Reg down-regulates hSGLT1 via blockage of ODC activity. Similar to hRS-Reg also the down-regulation of hSGLT1 by QEP was blunted when putrescine was added (FIG. 23C). FIG. 23D shows that ODC activity in human embryonic kidney cells which were stably transfected with ODC was decreased when hRS1-Reg was coexpressed. This suggests that hRS1-Reg inhibits ODC activity. In FIG. 23E unequivocal evidence is provided that QEP inhibits ODC activity. Purified ODC was incubated with QEP or the reverse tripeptide PEQ as control in a reaction tube and ODC activity was measured. It is shown that QEP but not PEQ inhibits ODC activity by about 40%.

The identification of ODC as receptor for hRS1-Reg and QEP dependent down-regulation of hSGLT1 provides the possibility to identify the hRS1-Reg and QEP binding site in ODC which allows to perform modelling in order to develop second generation drugs. In addition ODC mutants may be identified in patients which decrease the affinity and/or function of QEP and RS1-Reg variants predicting non-responders to QEP and/or RS1-Reg related drugs.

The present invention refers to the following nucleotide and amino acid sequences:

```
SEQ ID No. 1:
Nucleotide sequence encoding human RS1 (hRS1) (regulatory solute carrier protein,
family 1, member 1 (Homo sapiens)).
atgagcagcctgccgaccagcgatggcttaaccatccggcgcgcagcagcggccagagcccggatgtgggcaacccgat gagcctggcgcgcagcgtgagcgcgagcgtgtgcccgattaaaccgagcgatagcgatcgcattgaaccgaaagcggtga
```

-continued

```
aagcgctgaaagcgagcgcggaatttcagctgaacagcgaaaaaaagaacatctgagcctgcaggatctgagcgatcat gcgagcagcgcggatcatgcgccgaccgatcagagcccggcgatgccgatgcagaacagcagcgaagaaattaccgtggc gggcaacctggaaaaaagcgcggaacgcagcaccagggcctgaaatttcatctgcataccgccaggaagcgagcctga gcgtgaccagcacccgcatgcatgaaccgcagatgtttctgggcgaaaaagattggcatccggaaaaccagaacctgagc caggtgagcgatccgcagcagcatgaagaaccgggcaacgaacagtatgaagtggcgcagcagaaagcgagccatgatca ggaatatctgtgcaacattggcgatctggaactgccggaagaacgccagcagaaccagcataaaattgtggatctggaag cgaccatgaaaggcaacggcctgccgcagaacgtggatccgccgagcgcgaaaaaaagcattccgagcagcgaatgagc ggctgcagcaacagcgaaacctttatggaaattgataccgcgcagcagagcctggtgaccctgctgaacagcaccggccg ccagaacgcgaacgtgaaaaacattggcgcgctggatctgaccctggataacccgctgatggaagtggaaaccagcaaat gcaacacgagcagcgaaattctgaacgatagcattagcacccaggatctgcagccgccggaaaccaacgtggaaattccg ggcaccaacaaagaatatggccattataggaggccgagactgtgaggcagctgccagccgagcgtggaaagcgcggaaga aagctgaccgagcattaccgcggagctgaaagaactgcatgaactgctggtggtgagcagcaaaccggcgagcgaaaaca ccagcgaagaagtgatttgccagagcgaaaccattgaggaaggaaagaccagcattaaagatctgagcgaacgctggacc cagaaagaacatctgacacagaacgaacagtgaccgcaggtgagctttcatcaggagattagcgtgagcgtggaaaccga aaaactgaccggcaccagcagcgataccggccgcgaagcggtggaaaacgtgaactttcgcagcctgggcgatggcctga gcaccgataaagaaggcgtgccgaaaagccgcgaaagcattaacaaaaaccgcagcgtgaccgtgaccagcgcgaaaacc agcaacaagctgcattgcaccctgggcgtggaaattagaccgaaactgatggcgggcgaagaagatgcgctgaaccagac cagcgaaaagaccaaaagcatgagaagcaactttattctggtgaaagatctgggccagggcattcagaacagcgtgaccg atcgccaggaaacacgagaaaacgtgtgcccggatgcgagccgcccgctgatggaatatgaaccgccgaccagccatccg agcagcagccaggcgattctgccaccgctgatttttccggcgaccgatattgatcgcattctgcgcgcgggatttacact gaaggaagcgctgggagagctgcatcgcgtgggcggcaacgcggatctggcgctgctggtgctgctggcgaaaaaaattg tggtgccgacc
```

SEQ ID No. 2:
Amino acid sequence of human RS1 (hRS1) (regulatory solute carrier protein, family 1,
member 1 (*Homo sapiens*)). The regulator domain hRS1-Reg is bold and underlined.
MSSLPTSDGFNAPARSSGQSPDVGNPMSLARSVSASVCPIKPSDSDRIEPKAVKALKASAEFQLNSEKEEHLSLQDLSDH

ASSADHAPTDQSPAMPMQNSSEEITVAGNLEKSAERSTQGLKFHLHTRQEASLSVTSTRMHEPQMFLGEKDWHPENQNLS

QVSDPQQHEEPGNEQYEVAQQKASHDQEYLCNIGDLELPEERQQNQHKIVDLEATMKGNGLPQNVDPFSAKKSIPSSECS

GCSNSETFMEIDTAQQSLVTLLNSTGRQNANVKNIGALDLTLDNPLMEVETSKCNPSSEILNDSISTQDLQPPETNVEIP

GTNKEYGHYSSPSLCGSCQPSVESAEESCPSITAALKELHELLVVSSKPASENTSEEVICQSETIAEGQTSIKDLSERWT

QNEHLTQNEQCPQVSFHQATSVSVETEKLTGTSSDTGREAVENVNFRSLGDGLSTDKEGVPKSRESINKNRSVTVTSAKT

SNQLHCTLGVEISPKLLAGEEDALNQTSEQTKSLSSNFILVKDLGQGIQNSVTDRPETRENVCPDASRPLLEYEPPTSHP

SSSPAILPPLIFPATDIDRILRAGFTLQEALGALHRVGGNADLALLVLLAKNIVVFT

SEQ ID No. 3:
Nucleotide sequence encoding mouse RS1 (mRS1) (regulatory solute carrier protein,
family 1, member 1 (*Mus musculus*); Gene bank NM_023544.5).

```
     atg tcataattgc cgacttcaga tgggtttgac catccagctc cttcagggca gagtcctgag gttggtagcc cgacgagtct cgctcgctct gtttctgctt ccgtctgcgc catcaagccc ggtgacccca atagcattga atctctagct atggaggcta cgaaggcttc agctgaattc cagacaaaact ctaagaaaac agaccctcct cctctgcagg ttcttcctga cattgattcc tcaggagaga agagtctagc catgcctttc cataagtcat caaagaagc cgttgttgca ggtaatctgg agaaatctgt tgagaaagga acccagggcc tcagagtgta tctccacaca agacaggacg ctagtttaac tctcacaact actggaatgc gggagccaca
```

```
gatatttgcg gaggaaaaga gttggcatcc agaaaatcag accccaagtc ccgtgaacgg ccttcaggag cacagagaaa cagggagtgt acagcgagag ctggacagag agagtgttcc acaggaccag ggctgtcttt gtgacgcaga agaccttgag cttcatgaag aagttgtcag tttggaagct ctgaggaaag gtgagctaca agacacgct catcttccca gtgcagagaa gggtcttcca gcttcaggac tctgtagctg tccatgatca gaagacctga tggaagtaga tacagctgaa cagtctctgg ttgctatgtg cagctaaaca ggcaggcagg atgccgtcat caagagccct agtgtagcac atctcgcttc agataatccc actatggaag tggagacatt acagtctaac ccgtcatgtg agcatgtgga acattccatc ttgactcggg aattgcagct ccaagaagat aatgttgaca tgtctacaat ggataacaaa gatgacaatt cctattccct tctaagtggc cacggtcagc actctgtgga atcagcagaa gaattttgtt catctgtcac agtggccttg aaagaactcc atgagatttt ggtcattagc tgtaagccag cttcagaaga gtcacctgag catgttacct gtcagtcaga gataggagct gagagccaac caagtgtttc agacctttca ggaagaaggg tccaaagtgt gcatttgacc cctagtgacc agtactcaca aggctcctgt caccaggcca cctctgaatc aggaaagaca gaaatcgtag gaactgcccc ttgtgctgcg gtagaagatg aagcatccac tagctttgaa ggtatgggtg atggcttgtc acctgaccga gaagatgtcc gcagatcaac agagtcagcc aggaagagct gttctgtcgc cataacctcg gctaaactgt ctgagcagtt gccctgcacc tcaggggtag aaatagcacc tgaacttgca gcaagtgagg gtgcccacag tcagccttca gagcatgtgc ataatccagg cccagacagg ccggagacca gcagtgtctg ccctggagct gggttgcccc gtagtggatt ggaccaacct cccacacagt ccttgtccac ccctccgtt cttccaccgt tcatctttcc tgctgcagat gttgacagga ttattggtgc cggcttcact ctgcaggaag cgctcgggc tctgcatcga gttggtggga atgcagacct tgcccttatt gttttgttag caaagaacat tgtagtccca acataa
```

SEQ ID No. 4:
Amino acid sequence of mouse RS1 (mRS1) (regulatory solute carrier protein, family 1, member 1 (*Mus musculus*)). The regulator domain mRS1-Reg is bold and underlined.
MSSLPTSDGFDHPAPSGQSPEVGSPTSLARSVSASVCATKPGDPNSIESLAMEATKASAEFQTNSKKTDPPPLQVLPDLA

SSAEQSLAMPFHKSSKEAVVAGNLEKSVEKGTQGLRVYLHTRQDASLTLTTTGMREPQIFAEEKSWHPENQTPSPVNGLQ

HRETGSVQREAGQQSVPQDQGCLCDAEDLELHEEVVSLEALRKGELQRHAHLPSAEKGLPASGLCSCPCSEALMEVDTAE

QSLVAMCSSTGRQDAVIKSPSVAHLASDNPTMEVETLQSNPSCEPVEHSILTRELQLPEDNVDMSTMDNKDDNSSSLLSG

HGQPSVESAEEFCSSVTVALKELHELLVISCKPASEESPERVTCQSEIGAESQPSVSDLSGRRVQSVHLTPSDQYSQGSC

HQATSESGKTEIVGIAPCAAVEDEASTSEEGLGDGLSPDREDVRRSTESARKSCSVAITSAKLSEQLPCTSGVEIAPELA

ASFGAHSQPSEHVHNPGPDRPETSSVCPGAGLPRSGLDQPPTQSLSTPSVLPPFIFPAADVDRILGAGFTLQEALGALHR

VGGNA

SEQ ID No. 5:
Nucleotide sequence encoding hRS1-Reg.
tcttcaggacagagtcctgatgttggtaatcctatgagtcttgctcgctctgtctctgcttcagtctgccctatcaagcc cagtgactcagatcgcattgaacctaaagctgtgaaggctttgaaggcttcagctgaattccagctaaactctgaaagga aagaacatctttctttacaagatctttctgatcatgcttcctcagcagaccatgctccaacagaccagagtccagCtatg cctatgcag SEQ ID No. 6:
Amino acid sequence of hRS1-Reg.
SSGQSPDVGNPMSLARSVSASVCPIKPSDSDRIEPKAVKALKASAEFQLNSEKKEHLSLQDLSDHASSADHAPTDQSPAM

PMQ

-continued

SEQ ID No. 7:
Nucleotide sequence encoding mRS1-Reg.
ccttcagggcagagtcctgaggttggtagcccgacgagtctcgctcgctctgtttctgcttccgtctgcgccatc aagcccggtgacccccaatagcattgaatctctagctatggaggctacgaaggcttcagctgaattccagacaaac tctaagaaaacagaccctcctcctctgcaggttcttcctgaccttgcttcctcagcagagcagagtctagccatg cctttccat SEQ ID No. 8:
Amino acid sequence of mRS1-Reg.
PSGQSPEVGSPTSLARSVSASVCAIKPGDPNSIESLAMEATKASAEFQTNSKKTDPPPLQVLPCLASSAEQSLAMPFH SEQ ID No. 9:
Amino acid sequence of hRS1-Reg - the first/N-terminal QSP motive is replaced by QEP (hRS1-Reg(S20E)).
SSGQEPDVGNPMSLARSVSASVCPIKPSDSDRIEPKAVKALKASAEFQLNSEKKEHLSLQDLSDHASSADHAPTDQSPAM

PMQ

SEQ ID No. 10:
Amino acid sequence of mRS1-Reg - the first/N-terminal QSP motive is replaced by QEP (mRS1-Reg(S19E)).
PSGQEPEVGSPTSLARSVSASVCAIKPGDPNSIESLAMEATKASAEFQTNSKKTDPPPLQVLPDLASSAEQSLAMPFH SEQ ID No. 11:
Exemplary amino acid sequence of "$x_m$" of hRS1-Reg.
DVGNPMSLARSVSASVCPIKPSDSDRIEPKAVKALKASAEFQLNSEEKEELSLQDLSDHASSADHAPTDQSPAMPMQ SEQ ID No. 12:
Exemplary amino acid sequence of "$x_i$" of hRS1-Reg.
DVGNPMSLARSVSASVCPIKP SEQ ID No. 13:
Exemplary amino acid sequence of "$x_k$" of hRS1-Reg.
KAVKALKASAEFQLNSEKKERLSLQDLSDHASSADHAPTD SEQ ID No. 14:
Exemplary amino acid sequence of "$x_j$" of hRS1-Reg.
AMPMQ SEQ ID No. 15:
Exemplary amino acid sequence of "$x_m$" of mRS1-Reg.
EVGSPTSLARSVSASVCAIKPGDPNSIESLAMEATKASAEFQTNSKKTDPPPLQVLPDLASSAEQSLAMPFH

---

The invention claimed is:

1. A method of reducing or inhibiting sodium-glucose cotransporter 1 (SGLT1)-mediated glucose and/or galactose uptake in cells of a subject in need thereof, the method comprising administering to the subject a composition in an effective amount, wherein the composition comprises a polypeptide consisting of:
- (A) the amino acid sequence glutamine-glutamic acid-proline (QEP);
- (B) a derivative of the amino acid sequence QEP consisting of $QS_{thiophosphate}$-P;
- (C) a polypeptide selected from the group consisting of:
  - (a) a polypeptide which consists of the regulatory domain of RS1 (RS1-Reg) as depicted in SEQ ID NO: 9 or 10 or of RS1-Reg as depicted in SEQ ID NO: 6 or 8 having at least its first glutamine-serine-proline (QSP) motive from its N-terminus replaced by the amino acid sequence QEP or $QS_{thiophosphate}$-P;
  - (b) a polypeptide which consists of a polypeptide being at least 90% identical to RS1-Reg as depicted in SEQ ID NO: 9 or 10 and comprising at least the first QEP motive from the N-terminus of the RS1-Reg or $QS_{thiophosphate}$-P,
  - (c) a polypeptide which consists of a polypeptide of (a) or (b) having the S residue of one or more phosphorylation sites mutated to E, D, $S_{thiophosphate}$ or $T_{thiophosphate}$;
  - (d) a polypeptide which consists of a polypeptide of Formula I:

$$x_n\text{-Q-E-P-}x_m, \quad (I)$$

wherein x is any amino acid, n is an integer of 0-2 and m is an integer of 0-2;
  - (e) a polypeptide which consists of the polypeptide of Formula I as defined in (d) having the QEP motive replaced by $QS_{thiophosphate}$-P; and
  - (f) a polypeptide which consists of a fragment of the polypeptide of any one of (a) to (e), wherein said fragment comprises the amino acid sequence Q-E-P or $QS_{thiophosphate}$-P; or
- (D) a cysteine-terminated version of the amino acid sequence of (A), the derivative of (B) or the polypeptide of (C), wherein said subject has a D-glucose concentration that is from 100 μM to 100 mM in the subject's lumen of at least one part of the subject's gastrointestinal tract, or from 50 μM to 5 mM in the epithelial cells in at least one part of the subject's gastrointestinal tract, and wherein said composition is administered in combination with an energy-rich food which leads to said D-glucose concentration.

2. The method of claim 1, wherein said subject has a disease or disorder selected from the group consisting of obesity, diabetes mellitus and hyperglycemia.

3. The method of claim 2, wherein said disease or disorder is selected from the group consisting of type 2 diabetes and prediabetes.

4. The method of claim 1, wherein said energy-rich food has a sugar content of ≥1% by weight, a carbohydrate content of ≥10% by energy and/or a glycemic index of ≥70.

5. The method of claim 1, wherein the composition is administered orally, and with a carrier to release said polypeptide within at least one part of the patient's gastrointestinal tract.

6. The method of claim 5, wherein said carrier comprises a hydrogel.

7. The method of claim 1, wherein said composition:
- (i) is delivered by a hydrogel;
- (ii) is administered with a pharmaceutically acceptable excipient/carrier which is or comprises a hydrogel; and/or
- (iii) comprises the polypeptide being coupled to a hydrogel.

* * * * *

SEQUENCE LISTING

<160> NUMBER OF SEQ IDS: 35

<210> SEQ ID NO 1
<211> LENGTH: 1851
<212> TYPE: DNA
<213> ORGANISM: Homo sapiens

<400> SEQUENCE: 1

| | | | | | |
|---|---|---|---|---|---|
| atgagcagcc | tgccgaccag | cgatggcttt | aaccatccgg | cgcgcagcag | cggccagagc | 60 |
| ccggatgtgg | gcaacccgat | gagcctggcg | cgcagcgtga | gcgcgagcgt | gtgcccgatt | 120 |
| aaaccgagcg | atagcgatcg | cattgaaccg | aaagcggtga | aagcgctgaa | agcgagcgcg | 180 |
| gaatttcagc | tgaacagcga | aaaaaagaa | catctgagcc | tgcaggatct | gagcgatcat | 240 |
| gcgagcagcg | cggatcatgc | gccgaccgat | cagagcccgg | cgatgccgat | gcagaacagc | 300 |
| agcgaagaaa | ttaccgtggc | gggcaacctg | aaaaaagcg | cggaacgcag | cacccagggc | 360 |
| ctgaaatttc | atctgcatac | cgccaggaa | gcgagcctga | gcgtgaccag | cacccgcatg | 420 |
| catgaaccgc | agatgtttct | gggcgaaaaa | gattggcatc | cggaaaacca | gaacctgagc | 480 |
| caggtgagcg | atccgcagca | gcatgaagaa | ccgggcaacg | aacagtatga | agtggcgcag | 540 |
| cagaaagcga | gccatgatca | ggaatatctg | tgcaacattg | gcgatctgga | actgccggaa | 600 |

```
gaacgccagc agaaccagca taaaattgtg atctggaagc gaccatgaa aggcaacggc      660
ctgccgcaga acgtggatcc gccgagcgcg aaaaaaagca ttccgagcag cgaatgcagc      720
ggctgcagca acagcgaaac ctttatggaa attgataccg cgcagcagag cctggtgacc      780
ctgctgaaca gcaccggccg ccagaacgcg aacgtgaaaa acattggcgc gctggatctg      840
accctggata cccgctgat ggaagtggaa accagcaaat gcaacccgag cagcgaaatt      900
ctgaacgata gcattagcac ccaggatctg cagccgccgg aaaccaacgt ggaaattccg      960
ggcaccaaca agaatatgg ccattatagc agcccgagcc tgtgcggcag ctgccagccg     1020
agcgtggaaa gcgcggaaga agctgcccg agcattaccg cggcgctgaa agaactgcat     1080
gaactgctgg tggtgagcag caaaccggcg agcgaaaaca ccagcgaaga agtgatttgc     1140
cagagcgaaa ccattgcgga aggccagacc agcattaaag atctgagcga acgctggacc     1200
cagaacgaac atctgaccca gaacgaacag tgcccgcagg tgagctttca tcaggcgatt     1260
agcgtgagcg tggaaaccga aaaactgacc ggcaccagca gcgataccgg ccgcgaagcg     1320
gtggaaaacg tgaactttcg cagcctgggc gatggcctga gcaccgataa agaaggcgtg     1380
ccgaaaagcc gcgaaagcat taacaaaaac cgcagcgtga ccgtgaccag cgcgaaaacc     1440
agcaaccagc tgcattgcac cctgggcgtg gaaattagcc cgaaactgct ggcgggcgaa     1500
gaagatgcgc tgaaccagac cagcgaacag accaaaagcc tgagcagcaa ctttattctg     1560
gtgaaagatc tgggccaggg cattcagaac agcgtgaccg atcgcccgga aacccgcgaa     1620
aacgtgtgcc ggatgcgag ccgcccgctg ctggaatatg aaccgccgac cagccatccg     1680
agcagcagcc cggcgattct gccgccgctg attttccgg cgaccgatat tgatcgcatt     1740
ctgcgcgcgg gctttaccct gcaggaagcg ctgggcgcgc tgcatcgcgt gggcggcaac     1800
gcggatctgg cgctgctggt gctgctggcg aaaaacattg tggtgccgac c             1851
```

<210> SEQ ID NO 2
<211> LENGTH: 617
<212> TYPE: PRT
<213> ORGANISM: Homo sapiens

<400> SEQUENCE: 2

Met Ser Ser Leu Pro Thr Ser Asp Gly Phe Asn His Pro Ala Arg Ser
1               5                   10                  15

Ser Gly Gln Ser Pro Asp Val Gly Asn Pro Met Ser Leu Ala Arg Ser
            20                  25                  30

Val Ser Ala Ser Val Cys Pro Ile Lys Pro Ser Asp Ser Asp Arg Ile
        35                  40                  45

Glu Pro Lys Ala Val Lys Ala Leu Lys Ala Ser Ala Glu Phe Gln Leu
    50                  55                  60

Asn Ser Glu Lys Lys Glu His Leu Ser Leu Gln Asp Leu Ser Asp His
65                  70                  75                  80

Ala Ser Ser Ala Asp His Ala Pro Thr Asp Gln Ser Pro Ala Met Pro
                85                  90                  95

Met Gln Asn Ser Ser Glu Glu Ile Thr Val Ala Gly Asn Leu Glu Lys
            100                 105                 110

Ser Ala Glu Arg Ser Thr Gln Gly Leu Lys Phe His Leu His Thr Arg
        115                 120                 125

Gln Glu Ala Ser Leu Ser Val Thr Ser Thr Arg Met His Glu Pro Gln
    130                 135                 140

Met Phe Leu Gly Glu Lys Asp Trp His Pro Glu Asn Gln Asn Leu Ser
145                 150                 155                 160

-continued

```
Gln Val Ser Asp Pro Gln Gln His Glu Glu Pro Gly Asn Glu Gln Tyr
                165                 170                 175
Glu Val Ala Gln Gln Lys Ala Ser His Asp Gln Glu Tyr Leu Cys Asn
            180                 185                 190
Ile Gly Asp Leu Glu Leu Pro Glu Arg Gln Gln Asn Gln His Lys
        195                 200                 205
Ile Val Asp Leu Glu Ala Thr Met Lys Gly Asn Gly Leu Pro Gln Asn
    210                 215                 220
Val Asp Pro Pro Ser Ala Lys Lys Ser Ile Pro Ser Ser Glu Cys Ser
225                 230                 235                 240
Gly Cys Ser Asn Ser Glu Thr Phe Met Glu Ile Asp Thr Ala Gln Gln
                245                 250                 255
Ser Leu Val Thr Leu Leu Asn Ser Thr Gly Arg Gln Asn Ala Asn Val
            260                 265                 270
Lys Asn Ile Gly Ala Leu Asp Leu Thr Leu Asp Asn Pro Leu Met Glu
        275                 280                 285
Val Glu Thr Ser Lys Cys Asn Pro Ser Ser Glu Ile Leu Asn Asp Ser
    290                 295                 300
Ile Ser Thr Gln Asp Leu Gln Pro Pro Glu Thr Asn Val Glu Ile Pro
305                 310                 315                 320
Gly Thr Asn Lys Glu Tyr Gly His Tyr Ser Ser Pro Ser Leu Cys Gly
                325                 330                 335
Ser Cys Gln Pro Ser Val Glu Ser Ala Glu Glu Ser Cys Pro Ser Ile
            340                 345                 350
Thr Ala Ala Leu Lys Glu Leu His Glu Leu Leu Val Ser Ser Lys
        355                 360                 365
Pro Ala Ser Glu Asn Thr Ser Glu Glu Val Ile Cys Gln Ser Glu Thr
370                 375                 380
Ile Ala Glu Gly Gln Thr Ser Ile Lys Asp Leu Ser Glu Arg Trp Thr
385                 390                 395                 400
Gln Asn Glu His Leu Thr Gln Asn Glu Gln Cys Pro Gln Val Ser Phe
                405                 410                 415
His Gln Ala Ile Ser Val Ser Val Glu Thr Glu Lys Leu Thr Gly Thr
            420                 425                 430
Ser Ser Asp Thr Gly Arg Glu Ala Val Glu Asn Val Asn Phe Arg Ser
        435                 440                 445
Leu Gly Asp Gly Leu Ser Thr Asp Lys Glu Gly Val Pro Lys Ser Arg
    450                 455                 460
Glu Ser Ile Asn Lys Asn Arg Ser Val Thr Val Thr Ser Ala Lys Thr
465                 470                 475                 480
Ser Asn Gln Leu His Cys Thr Leu Gly Val Glu Ile Ser Pro Lys Leu
                485                 490                 495
Leu Ala Gly Glu Glu Asp Ala Leu Asn Gln Thr Ser Glu Gln Thr Lys
            500                 505                 510
Ser Leu Ser Ser Asn Phe Ile Leu Val Lys Asp Leu Gly Gln Gly Ile
        515                 520                 525
Gln Asn Ser Val Thr Asp Arg Pro Glu Thr Arg Glu Asn Val Cys Pro
    530                 535                 540
Asp Ala Ser Arg Pro Leu Leu Glu Tyr Glu Pro Thr Ser His Pro
545                 550                 555                 560
Ser Ser Ser Pro Ala Ile Leu Pro Pro Leu Ile Phe Pro Ala Thr Asp
                565                 570                 575
```

Ile Asp Arg Ile Leu Arg Ala Gly Phe Thr Leu Gln Glu Ala Leu Gly
            580                 585                 590

Ala Leu His Arg Val Gly Gly Asn Ala Asp Leu Ala Leu Leu Val Leu
        595                 600                 605

Leu Ala Lys Asn Ile Val Val Pro Thr
    610                 615

<210> SEQ ID NO 3
<211> LENGTH: 1749
<212> TYPE: DNA
<213> ORGANISM: Mus musculus

<400> SEQUENCE: 3

| | | | | | | |
|---|---|---|---|---|---|---|
| atgtcatcat | tgccgacttc | agatgggttt | gaccatccag | ctccttcagg | gcagagtcct | 60 |
| gaggttggta | gcccgacgag | tctcgctcgc | tctgtttctg | cttccgtctg | cgccatcaag | 120 |
| cccggtgacc | ccaatagcat | tgaatctcta | gctatggagg | ctacgaaggc | ttcagctgaa | 180 |
| ttccagacaa | actctaagaa | aacagaccct | cctcctctgc | aggttcttcc | tgaccttgct | 240 |
| tcctcagcag | agcagagtct | agccatgcct | ttccataagt | catcaaaaga | agccgttgtt | 300 |
| gcaggtaatc | tggagaaatc | tgttgagaaa | ggaacccagg | gcctcagagt | gtatctccac | 360 |
| acaagacagg | acgctagttt | aactctcaca | actactggga | tgcgggagcc | acagatattt | 420 |
| gcggaggaaa | agagttggca | tccagaaaat | cagaccccaa | gtcccgtgaa | cggccttcag | 480 |
| cagcacagag | aaacagggag | tgtacagcga | gaggctggac | agcagagtgt | tccacaggac | 540 |
| cagggctgtc | tttgtgacgc | agaagacctt | gagcttcatg | aagaagttgt | cagtttggaa | 600 |
| gctctgagga | aggtgagct | acaaagacac | gctcatcttc | ccagtgcaga | aagggtctt | 660 |
| ccagcttcag | gactctgtag | ctgtccatgc | tcagaagccc | tgatggaagt | agatacagct | 720 |
| gaacagtctc | tggttgctat | gtgcagctca | acaggcaggc | aggatgccgt | catcaagagc | 780 |
| cctagtgtag | cacatctcgc | ttcagataat | cccactatgg | aagtggagac | attacagtct | 840 |
| aacccgtcct | gtgagcctgt | ggaacattcc | atcttgactc | gggaattgca | gctcccagaa | 900 |
| gataatgttg | acatgtctac | aatggataac | aaagatgaca | attcctcttc | ccttctaagt | 960 |
| ggccacggtc | agccctctgt | ggaatcagca | gaagaatttt | gttcatctgt | cacagtggcc | 1020 |
| ttgaaagaac | tccatgagct | tttggtcatt | agctgtaagc | cagcttcaga | agagtcacct | 1080 |
| gagcatgtta | cctgtcagtc | agagatagga | gctgagagcc | aaccaagtgt | ttcagacctt | 1140 |
| tcaggaagaa | gggtccaaag | tgtgcatttg | accctagtg | accagtactc | acaaggctcc | 1200 |
| tgtcaccagg | ccacctctga | atcaggaaag | acagaaatcg | taggaactgc | ccttgtgct | 1260 |
| gcggtagaag | atgaagcatc | cactagcttt | gaaggtctgg | gtgatggctt | gtcacctgac | 1320 |
| cgagaagatg | tccgcagatc | aacagagtca | gccaggaaga | gctgttctgt | cgccataacc | 1380 |
| tcggctaaac | tgtctgagca | gttgccctgc | acctcagggg | tagaaatagc | acctgaactt | 1440 |
| gcagcaagtg | agggtgccca | cagtcagcct | tcagagcatg | tgcataatcc | aggcccagac | 1500 |
| aggccggaga | ccagcagtgt | ctgccctgga | gctgggttgc | cccgtagtgg | attggaccaa | 1560 |
| cctcccacac | agtccttgtc | caccccctcc | gttcttccac | cgttcatctt | tcctgctgca | 1620 |
| gatgttgaca | ggattcttgg | tgccggcttc | actctgcagg | aagcgctcgg | ggctctgcat | 1680 |
| cgagttggtg | ggaatgcaga | ccttgccctt | cttgttttgt | tagcaaagaa | cattgtagtc | 1740 |
| ccaacataa | | | | | | 1749 |

<210> SEQ ID NO 4

```
<211> LENGTH: 565
<212> TYPE: PRT
<213> ORGANISM: Mus musculus

<400> SEQUENCE: 4

Met Ser Ser Leu Pro Thr Ser Asp Gly Phe Asp His Pro Ala Pro Ser
1               5                   10                  15

Gly Gln Ser Pro Glu Val Gly Ser Pro Thr Ser Leu Ala Arg Ser Val
            20                  25                  30

Ser Ala Ser Val Cys Ala Ile Lys Pro Gly Asp Pro Asn Ser Ile Glu
        35                  40                  45

Ser Leu Ala Met Glu Ala Thr Lys Ala Ser Ala Glu Phe Gln Thr Asn
    50                  55                  60

Ser Lys Lys Thr Asp Pro Pro Leu Gln Val Leu Pro Asp Leu Ala
65                  70                  75                  80

Ser Ser Ala Glu Gln Ser Leu Ala Met Pro Phe His Lys Ser Ser Lys
                85                  90                  95

Glu Ala Val Val Ala Gly Asn Leu Glu Lys Ser Val Glu Lys Gly Thr
            100                 105                 110

Gln Gly Leu Arg Val Tyr Leu His Thr Arg Gln Asp Ala Ser Leu Thr
        115                 120                 125

Leu Thr Thr Thr Gly Met Arg Glu Pro Gln Ile Phe Ala Glu Glu Lys
    130                 135                 140

Ser Trp His Pro Glu Asn Gln Thr Pro Ser Pro Val Asn Gly Leu Gln
145                 150                 155                 160

His Arg Glu Thr Gly Ser Val Gln Arg Glu Ala Gly Gln Gln Ser Val
                165                 170                 175

Pro Gln Asp Gln Gly Cys Leu Cys Asp Ala Glu Asp Leu Glu Leu His
            180                 185                 190

Glu Glu Val Val Ser Leu Glu Ala Leu Arg Lys Gly Glu Leu Gln Arg
        195                 200                 205

His Ala His Leu Pro Ser Ala Glu Lys Gly Leu Pro Ala Ser Gly Leu
    210                 215                 220

Cys Ser Cys Pro Cys Ser Glu Ala Leu Met Glu Val Asp Thr Ala Glu
225                 230                 235                 240

Gln Ser Leu Val Ala Met Cys Ser Ser Thr Gly Arg Gln Asp Ala Val
                245                 250                 255

Ile Lys Ser Pro Ser Val Ala His Leu Ala Ser Asp Asn Pro Thr Met
            260                 265                 270

Glu Val Glu Thr Leu Gln Ser Asn Pro Ser Cys Glu Pro Val Glu His
        275                 280                 285

Ser Ile Leu Thr Arg Glu Leu Gln Leu Pro Glu Asp Asn Val Asp Met
    290                 295                 300

Ser Thr Met Asp Asn Lys Asp Asp Asn Ser Ser Ser Leu Leu Ser Gly
305                 310                 315                 320

His Gly Gln Pro Ser Val Glu Ser Ala Glu Phe Cys Ser Ser Val
                325                 330                 335

Thr Val Ala Leu Lys Glu Leu His Glu Leu Leu Val Ile Ser Cys Lys
            340                 345                 350

Pro Ala Ser Glu Glu Ser Pro Glu His Val Thr Cys Gln Ser Glu Ile
        355                 360                 365

Gly Ala Glu Ser Gln Pro Ser Val Ser Asp Leu Ser Gly Arg Arg Val
    370                 375                 380

Gln Ser Val His Leu Thr Pro Ser Asp Gln Tyr Ser Gln Gly Ser Cys
```

```
                385                 390                 395                 400
        His Gln Ala Thr Ser Glu Ser Gly Lys Thr Glu Ile Val Gly Thr Ala
                            405                 410                 415

Pro Cys Ala Ala Val Glu Asp Glu Ala Ser Thr Ser Phe Glu Gly Leu
                        420                 425                 430

Gly Asp Gly Leu Ser Pro Asp Arg Glu Asp Val Arg Arg Ser Thr Glu
                    435                 440                 445

Ser Ala Arg Lys Ser Cys Ser Val Ala Ile Thr Ser Ala Lys Leu Ser
                450                 455                 460

Glu Gln Leu Pro Cys Thr Ser Gly Val Glu Ile Ala Pro Glu Leu Ala
        465                 470                 475                 480

Ala Ser Glu Gly Ala His Ser Gln Pro Ser Glu His Val His Asn Pro
                            485                 490                 495

Gly Pro Asp Arg Pro Glu Thr Ser Ser Val Cys Pro Gly Ala Gly Leu
                        500                 505                 510

Pro Arg Ser Gly Leu Asp Gln Pro Pro Thr Gln Ser Leu Ser Thr Pro
                    515                 520                 525

Ser Val Leu Pro Pro Phe Ile Phe Pro Ala Ala Asp Val Asp Arg Ile
                530                 535                 540

Leu Gly Ala Gly Phe Thr Leu Gln Glu Ala Leu Gly Ala Leu His Arg
        545                 550                 555                 560

Val Gly Gly Asn Ala
                    565

<210> SEQ ID NO 5
<211> LENGTH: 249
<212> TYPE: DNA
<213> ORGANISM: Homo sapiens

<400> SEQUENCE: 5
tcttcaggac agagtcctga tgttggtaat cctatgagtc ttgctcgctc tgtctctgct      60
tcagtctgcc ctatcaagcc cagtgactca gatcgcattg aacctaaagc tgtgaaggct     120
ttgaaggctt cagctgaatt ccagctaaac tctgaaaaga agaacatctc ttctttacaa     180
gatctttctg atcatgcttc ctcagcagac catgctccaa cagaccagag tccagctatg     240
cctatgcag                                                             249

<210> SEQ ID NO 6
<211> LENGTH: 83
<212> TYPE: PRT
<213> ORGANISM: Homo sapiens

<400> SEQUENCE: 6

Ser Ser Gly Gln Ser Pro Asp Val Gly Asn Pro Met Ser Leu Ala Arg
1               5                   10                  15

Ser Val Ser Ala Ser Val Cys Pro Ile Lys Pro Ser Asp Ser Asp Arg
            20                  25                  30

Ile Glu Pro Lys Ala Val Lys Ala Leu Lys Ala Ser Ala Glu Phe Gln
        35                  40                  45

Leu Asn Ser Glu Lys Lys Glu His Leu Ser Leu Gln Asp Leu Ser Asp
    50                  55                  60

His Ala Ser Ser Ala Asp His Ala Pro Thr Asp Gln Ser Pro Ala Met
65                  70                  75                  80

Pro Met Gln
```

```
<210> SEQ ID NO 7
<211> LENGTH: 234
<212> TYPE: DNA
<213> ORGANISM: Mus musculus

<400> SEQUENCE: 7
ccttcagggc agagtcctga ggttggtagc ccgacgagtc tcgctcgctc tgtttctgct      60
tccgtctgcg ccatcaagcc cggtgacccc aatagcattg aatctctagc tatggaggct     120
acgaaggctt cagctgaatt ccagacaaac tctaagaaaa cagaccctcc tcctctgcag     180
gttcttcctg accttgcttc ctcagcagag cagagtctag ccatgccttt ccat           234

<210> SEQ ID NO 8
<211> LENGTH: 78
<212> TYPE: PRT
<213> ORGANISM: Mus musculus

<400> SEQUENCE: 8

Pro Ser Gly Gln Ser Pro Glu Val Gly Ser Pro Thr Ser Leu Ala Arg
1               5                   10                  15

Ser Val Ser Ala Ser Val Cys Ala Ile Lys Pro Gly Asp Pro Asn Ser
                20                  25                  30

Ile Glu Ser Leu Ala Met Glu Ala Thr Lys Ala Ser Ala Glu Phe Gln
            35                  40                  45

Thr Asn Ser Lys Lys Thr Asp Pro Pro Leu Gln Val Leu Pro Asp
        50                  55                  60

Leu Ala Ser Ser Ala Glu Gln Ser Leu Ala Met Pro Phe His
65                  70                  75

<210> SEQ ID NO 9
<211> LENGTH: 83
<212> TYPE: PRT
<213> ORGANISM: Artificial Sequence
<220> FEATURE:
<223> OTHER INFORMATION: hRS1-Reg(S20E)

<400> SEQUENCE: 9

Ser Ser Gly Gln Glu Pro Asp Val Gly Asn Pro Met Ser Leu Ala Arg
1               5                   10                  15

Ser Val Ser Ala Ser Val Cys Pro Ile Lys Pro Ser Asp Ser Asp Arg
                20                  25                  30

Ile Glu Pro Lys Ala Val Lys Ala Leu Lys Ala Ser Ala Glu Phe Gln
            35                  40                  45

Leu Asn Ser Glu Lys Lys Glu His Leu Ser Leu Gln Asp Leu Ser Asp
        50                  55                  60

His Ala Ser Ser Ala Asp His Ala Pro Thr Asp Gln Ser Pro Ala Met
65                  70                  75                  80

Pro Met Gln

<210> SEQ ID NO 10
<211> LENGTH: 78
<212> TYPE: PRT
<213> ORGANISM: Artificial Sequence
<220> FEATURE:
<223> OTHER INFORMATION: mRS1-Reg(S19E)

<400> SEQUENCE: 10

Pro Ser Gly Gln Glu Pro Glu Val Gly Ser Pro Thr Ser Leu Ala Arg
1               5                   10                  15

Ser Val Ser Ala Ser Val Cys Ala Ile Lys Pro Gly Asp Pro Asn Ser
```

```
                   20                  25                  30

Ile Glu Ser Leu Ala Met Glu Ala Thr Lys Ala Ser Ala Glu Phe Gln
            35                  40                  45

Thr Asn Ser Lys Lys Thr Asp Pro Pro Leu Gln Val Leu Pro Asp
        50                  55                  60

Leu Ala Ser Ser Ala Glu Gln Ser Leu Ala Met Pro Phe His
65                  70                  75

<210> SEQ ID NO 11
<211> LENGTH: 77
<212> TYPE: PRT
<213> ORGANISM: Homo sapiens

<400> SEQUENCE: 11

Asp Val Gly Asn Pro Met Ser Leu Ala Arg Ser Val Ser Ala Ser Val
1               5                   10                  15

Cys Pro Ile Lys Pro Ser Asp Ser Asp Arg Ile Glu Pro Lys Ala Val
            20                  25                  30

Lys Ala Leu Lys Ala Ser Ala Glu Phe Gln Leu Asn Ser Glu Lys Lys
        35                  40                  45

Glu His Leu Ser Leu Gln Asp Leu Ser Asp His Ala Ser Ser Ala Asp
    50                  55                  60

His Ala Pro Thr Asp Gln Ser Pro Ala Met Pro Met Gln
65                  70                  75

<210> SEQ ID NO 12
<211> LENGTH: 21
<212> TYPE: PRT
<213> ORGANISM: Homo sapiens

<400> SEQUENCE: 12

Asp Val Gly Asn Pro Met Ser Leu Ala Arg Ser Val Ser Ala Ser Val
1               5                   10                  15

Cys Pro Ile Lys Pro
            20

<210> SEQ ID NO 13
<211> LENGTH: 40
<212> TYPE: PRT
<213> ORGANISM: Homo sapiens

<400> SEQUENCE: 13

Lys Ala Val Lys Ala Leu Lys Ala Ser Ala Glu Phe Gln Leu Asn Ser
1               5                   10                  15

Glu Lys Lys Glu His Leu Ser Leu Gln Asp Leu Ser Asp His Ala Ser
            20                  25                  30

Ser Ala Asp His Ala Pro Thr Asp
        35                  40

<210> SEQ ID NO 14
<211> LENGTH: 5
<212> TYPE: PRT
<213> ORGANISM: Homo sapiens

<400> SEQUENCE: 14

Ala Met Pro Met Gln
1               5

<210> SEQ ID NO 15
<211> LENGTH: 72
```

```
<212> TYPE: PRT
<213> ORGANISM: Mus musculus

<400> SEQUENCE: 15

Glu Val Gly Ser Pro Thr Ser Leu Ala Arg Ser Val Ser Ala Ser Val
1               5                   10                  15

Cys Ala Ile Lys Pro Gly Asp Pro Asn Ser Ile Glu Ser Leu Ala Met
            20                  25                  30

Glu Ala Thr Lys Ala Ser Ala Glu Phe Gln Thr Asn Ser Lys Lys Thr
                35                  40                  45

Asp Pro Pro Pro Leu Gln Val Leu Pro Asp Leu Ala Ser Ser Ala Glu
        50                  55                  60

Gln Ser Leu Ala Met Pro Phe His
65                  70

<210> SEQ ID NO 16
<211> LENGTH: 18
<212> TYPE: PRT
<213> ORGANISM: Artificial Sequence
<220> FEATURE:
<223> OTHER INFORMATION: RS1-Reg-derived polypeptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 16

Xaa Gln Glu Pro Xaa Ser Asp Ser Asp Arg Ile Glu Pro Xaa Gln Ser
1               5                   10                  15

Pro Xaa

<210> SEQ ID NO 17
<211> LENGTH: 8
<212> TYPE: PRT
<213> ORGANISM: Homo sapiens

<400> SEQUENCE: 17

Ser Asp Ser Asp Arg Ile Glu Pro
1               5

<210> SEQ ID NO 18
<211> LENGTH: 77
<212> TYPE: PRT
<213> ORGANISM: Artificial Sequence
<220> FEATURE:
<223> OTHER INFORMATION: Part of a RS1-Reg-derived polypeptide (xm)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
```

```
<222> LOCATION: (6)..(6)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(26)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (48)..(52)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (76)..(77)
<223> OTHER INFORMATION: Xaa can be any naturally occurring amino acid

<400> SEQUENCE: 18

Xaa Val Gly Xaa Pro Xaa Ser Leu Ala Arg Ser Val Ser Ala Ser Xaa
1               5                   10                  15

Cys Xaa Ile Lys Pro Xaa Asp Xaa Xaa Xaa Ile Glu Xaa Xaa Ala Xaa
            20                  25                  30

Xaa Ala Xaa Lys Ala Ser Ala Glu Phe Gln Xaa Asn Ser Xaa Lys Xaa
        35                  40                  45

Xaa Xaa Xaa Xaa Leu Gln Xaa Leu Xaa Asp Xaa Ala Ser Ser Ala Xaa
```

His Ala Pro Thr Asp Gln Ser Xaa Ala Met Pro Xaa Xaa
65                  70                  75

<210> SEQ ID NO 19
<211> LENGTH: 72
<212> TYPE: PRT
<213> ORGANISM: Mus musculus

<400> SEQUENCE: 19

Glu Val Gly Ser Pro Thr Ser Leu Ala Arg Ser Val Ser Ala Ser Val
1               5                   10                  15

Cys Ala Ile Lys Pro Gly Asp Pro Asn Ser Ile Glu Ser Leu Ala Met
            20                  25                  30

Glu Ala Thr Lys Ala Ser Ala Glu Phe Gln Thr Asn Ser Lys Lys Thr
        35                  40                  45

Asp Pro Pro Pro Leu Gln Val Leu Pro Asp Leu Ala Ser Ser Ala Glu
    50                  55                  60

Gln Ser Leu Ala Met Pro Phe His
65                  70

<210> SEQ ID NO 20
<211> LENGTH: 77
<212> TYPE: PRT
<213> ORGANISM: Homo sapiens

<400> SEQUENCE: 20

Asp Val Gly Asn Pro Met Ser Leu Ala Arg Ser Val Ser Ala Ser Val
1               5                   10                  15

Cys Pro Ile Lys Pro Ser Asp Ser Asp Arg Ile Glu Pro Lys Ala Val
            20                  25                  30

Lys Ala Leu Lys Ala Ser Ala Glu Phe Gln Leu Asn Ser Glu Lys Lys
        35                  40                  45

Glu His Leu Ser Leu Gln Asp Leu Ser Asp His Ala Ser Ser Ala Asp
    50                  55                  60

His Ala Pro Thr Asp Gln Ser Pro Ala Met Pro Met Gln
65                  70                  75

<210> SEQ ID NO 21
<211> LENGTH: 21
<212> TYPE: PRT
<213> ORGANISM: Artificial Sequence
<220> FEATURE:
<223> OTHER INFORMATION: Part of a RS1-Reg-derived polypeptide (x1)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

```
<400> SEQUENCE: 21

Xaa Val Gly Xaa Pro Xaa Ser Leu Ala Arg Ser Val Ser Ala Ser Xaa
1               5                   10                  15

Cys Xaa Ile Lys Pro
            20

<210> SEQ ID NO 22
<211> LENGTH: 21
<212> TYPE: PRT
<213> ORGANISM: Mus musculus

<400> SEQUENCE: 22

Glu Val Gly Ser Pro Thr Ser Leu Ala Arg Ser Val Ser Ala Ser Val
1               5                   10                  15

Cys Ala Ile Lys Pro
            20

<210> SEQ ID NO 23
<211> LENGTH: 21
<212> TYPE: PRT
<213> ORGANISM: Homo sapiens

<400> SEQUENCE: 23

Asp Val Gly Asn Pro Met Ser Leu Ala Arg Ser Val Ser Ala Ser Val
1               5                   10                  15

Cys Pro Ile Lys Pro
            20

<210> SEQ ID NO 24
<211> LENGTH: 40
<212> TYPE: PRT
<213> ORGANISM: Artificial Sequence
<220> FEATURE:
<223> OTHER INFORMATION: Part of a RS1-Reg-derived polypeptide (xm)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (19)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
```

```
<220> FEATURE:
<221> NAME/KEY: misc_feature
<222> LOCATION: (35)..(35)
<223> OTHER INFORMATION: Xaa can be any naturally occurring amino acid

<400> SEQUENCE: 24

Xaa Ala Xaa Xaa Ala Xaa Lys Ala Ser Ala Glu Phe Gln Xaa Asn Ser
1               5                   10                  15

Xaa Lys Xaa Xaa Xaa Xaa Xaa Leu Gln Xaa Leu Xaa Asp Xaa Ala Ser
            20                  25                  30

Ser Ala Xaa His Ala Pro Thr Asp
        35                  40

<210> SEQ ID NO 25
<211> LENGTH: 35
<212> TYPE: PRT
<213> ORGANISM: Mus musculus

<400> SEQUENCE: 25

Leu Ala Met Glu Ala Thr Lys Ala Ser Ala Glu Phe Gln Thr Asn Ser
1               5                   10                  15

Lys Lys Thr Asp Pro Pro Pro Leu Gln Val Leu Pro Asp Leu Ala Ser
            20                  25                  30

Ser Ala Glu
        35

<210> SEQ ID NO 26
<211> LENGTH: 40
<212> TYPE: PRT
<213> ORGANISM: Homo sapiens

<400> SEQUENCE: 26

Lys Ala Val Lys Ala Leu Lys Ala Ser Ala Glu Phe Gln Leu Asn Ser
1               5                   10                  15

Glu Lys Lys Glu His Leu Ser Leu Gln Asp Leu Ser Asp His Ala Ser
            20                  25                  30

Ser Ala Asp His Ala Pro Thr Asp
        35                  40

<210> SEQ ID NO 27
<211> LENGTH: 5
<212> TYPE: PRT
<213> ORGANISM: Artificial Sequence
<220> FEATURE:
<223> OTHER INFORMATION: Part of a RS1-Reg-derived polypeptide (xj)
<220> FEATURE:
<221> NAME/KEY: misc_feature
<222> LOCATION: (4)..(5)
<223> OTHER INFORMATION: Xaa can be any naturally occurring amino acid

<400> SEQUENCE: 27

Ala Met Pro Xaa Xaa
1               5

<210> SEQ ID NO 28
<211> LENGTH: 5
<212> TYPE: PRT
<213> ORGANISM: Mus musculus

<400> SEQUENCE: 28

Ala Met Pro Phe His
1               5
```

```
<210> SEQ ID NO 29
<211> LENGTH: 5
<212> TYPE: PRT
<213> ORGANISM: Homo sapiens

<400> SEQUENCE: 29

Ala Met Pro Met Gln
1               5

<210> SEQ ID NO 30
<211> LENGTH: 6
<212> TYPE: PRT
<213> ORGANISM: Artificial Sequence
<220> FEATURE:
<223> OTHER INFORMATION: QEP multimer

<400> SEQUENCE: 30

Gln Glu Pro Gln Glu Pro
1               5

<210> SEQ ID NO 31
<211> LENGTH: 9
<212> TYPE: PRT
<213> ORGANISM: Artificial Sequence
<220> FEATURE:
<223> OTHER INFORMATION: QEP multimer

<400> SEQUENCE: 31

Gln Glu Pro Gln Glu Pro Gln Glu Pro
1               5

<210> SEQ ID NO 32
<211> LENGTH: 7
<212> TYPE: PRT
<213> ORGANISM: Artificial Sequence
<220> FEATURE:
<223> OTHER INFORMATION: QEP multimer with linker
<220> FEATURE:
<221> NAME/KEY: misc_feature
<222> LOCATION: (4)..(4)
<223> OTHER INFORMATION: Xaa can be any naturally occurring amino acid

<400> SEQUENCE: 32

Gln Glu Pro Xaa Gln Glu Pro
1               5

<210> SEQ ID NO 33
<211> LENGTH: 11
<212> TYPE: PRT
<213> ORGANISM: Artificial Sequence
<220> FEATURE:
<223> OTHER INFORMATION: QEP multimer with linker
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 33

Gln Glu Pro Xaa Gln Glu Pro Xaa Gln Glu Pro
1               5                   10

<210> SEQ ID NO 34
<211> LENGTH: 11
<212> TYPE: PRT
<213> ORGANISM: Artificial Sequence
```

```
<220> FEATURE:
<223> OTHER INFORMATION: TAT peptide

<400> SEQUENCE: 34

Cys Gly Arg Leu Leu Arg Arg Gln Arg Arg Arg
1               5                   10

<210> SEQ ID NO 35
<211> LENGTH: 8
<212> TYPE: PRT
<213> ORGANISM: Artificial Sequence
<220> FEATURE:
<223> OTHER INFORMATION: Formula Ia

<400> SEQUENCE: 35

Ser Asp Ser Asp Arg Ile Glu Pro
1               5
```